US006894156B2

(12) United States Patent
Ebersole et al.

(10) Patent No.: US 6,894,156 B2
(45) Date of Patent: May 17, 2005

(54) NUCLEIC ACID FRAGMENTS FOR THE IDENTIFICATION OF DECHLORINATING BACTERIA

(75) Inventors: Richard C. Ebersole, Wilmington, DE (US); Edwin R. Hendrickson, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 322 days.

(21) Appl. No.: 10/061,071

(22) Filed: Jan. 29, 2002

(65) Prior Publication Data

US 2003/0077601 A1 Apr. 24, 2003

Related U.S. Application Data

(63) Continuation-in-part of application No. 09/548,998, filed on Apr. 14, 2000, now Pat. No. 6,797,817.
(60) Provisional application No. 60/129,511, filed on Apr. 15, 1999.

(51) Int. Cl.[7] ............................. C07H 21/04; C12N 1/00
(52) U.S. Cl. ........................................ 536/24.1; 435/243
(58) Field of Search .......................... 536/24.1; 435/243, 435/262.5

(56) References Cited

U.S. PATENT DOCUMENTS

| | | | |
|---|---|---|---|
| 4,851,330 A | 7/1989 | Kohne | |
| 5,540,838 A | 7/1996 | Smullen et al. | |
| 5,574,145 A | 11/1996 | Barry et al. | |

FOREIGN PATENT DOCUMENTS

| | | | |
|---|---|---|---|
| EP | 0 864 542 A2 | 9/1998 | |
| WO | WO 89/06704 A1 | 7/1989 | |
| WO | WO 98 49106 A1 | 11/1998 | |
| WO | WO 0063443 A2 | 10/2000 | |

OTHER PUBLICATIONS

Loffler et al., 16S rRNA gene–based detection of tetrachloethene–dechlorinating Desulfuromonas and Dehalococcoides species, Applied and Environmental Microbiology, vol. 66, No. 4, Apr. 2000, pp. 1369–1374, XP002215287.

Eberson et al., Detection of dechlorinating bacteria in groundwater and soils from waste sites contaminated with PCE and TCE, Abstracts in Environmental and General Applied Microbiology, vol. 99, May 30, 1999, pp. 539, XP008008413.

Carrol et al., The molecular detection of Dehalococcoides ethenogenes in PCR and TCE–contaminated sites by PCR, Abstracts in Environmental and General Applied Microbiology, vol. 90, May 30, 1999, Jun. 3, 1999, XP008008415.

Ritalahti et al., Dehalococcoides–like population detected in 1,2–dichloropropane dechloronating enrichment cultures, Abstracts of the American Society for Microbiology, vol. 101m pp. 20, May 24, 2001, XP002216099.

Maymo–Gatell Xavier et al., Isolation of a bacterium that reductively dechlorinates tetrachloroethene to ethene., Science (Washington D.C.) vol. 276, No. 5318, 1997 pp. 1568–1571 XP002179678.

Primary Examiner—James Ketter
Assistant Examiner—Nancy T. Vogel

(57) ABSTRACT

A unique 16S rRNA profile derived from *Dehalococcoides ethenogenes* has been identified and isolated. The profile contains several nucleic acid fragments that are linked to dechlorinating activity. These sequences are set forth in SEQ ID NO:1, SEQ ID NO:8, SEQ ID NO:30, and SEQ ID NO:34.

1 Claim, 12 Drawing Sheets

OTHER PUBLICATIONS

Holoman Tracy R. Pulliam et al., "Characterization of a defined 1,3,5,6-tetrachlorobiphenyl-ortho-dechl orinating microbial community by comparative sequence analysis of genes coding for 16S rRNA." Applied and Environmental Microbiology, vol. 64, No. 9, 1998, pp. 3359–3367, XP002179677.

Von Wintzingerode Friedrich et al., "Phylogenetic analysis of an anaerobic, trichlorobenzene-transforming microbial consortium.", Applied and Environmental Microbiology, vol., 65, No. 1, Jan. 1999, pp. 283–286, XP002179679.

Lamontagne M. G. et al., "Identification and analysis of PCB dechlorinating anaerobic enrichments by amplification: Accuracy of community structure based on restriction analysis and partial sequencing of 16S rRNA genes.", Journal of Applied Microbiology, vol. 84, No. 6, Jun. 1998, pp. 1156–1162, XP001024984.

Biswas, N. et al., Water Environ. Res. 64, 170, 10, 1(1992).

Hutter, G. M. et al., Water Environ. Res. 54, 59, (1992).

Vogel, T. M. Environ. Sci. Technol., 21, 722, (1987).

Kochian et al., Plant Mol. Biol., 46, 237, 1995.

Delhaize et al., Plant Physiol. 107:315, 1995.

Freedman et al., Appl. Environ. Microbiol. 55:2144, 1999.

Maymo–Gatell et al., Science, 176:1568, 1977.

Woese, Scientific American 244, 6, 1981.

Molecular Analysis of Dehalococcides 16S Ribosomal DNA from Chloroethene–Contaminated Sites throughout North America and Europe, Hendrickson et al., Applied and Environ. Micro., Feb. 2002.

FIGURE 1 The *Dehalococcoides sp.* alignment

```
DHE seq alignments1.msf  MSF: 1223
Name: DHE.(cornell)         Len: 1443
Name: DHE (stf).seq         Len: 1386
Name: DHE.(pl ).seq         Len: 1385
Name: DHE.(dll).seq         Len: 1385
Name: DHE.(dab).seq         Len: 1385
Name: DHE.(pin).seq         Len: 1385
//
//
                    1                                                           60
    DHE.(cornell)   GATGAACGCTAGCGGCGTGCCTTATGCATGCAAGTCGAACGGTCTTAAGCAATTAAGATA
    DHE(stf).seq    GATGAACGCTAGCGGCGTGCCTTATGCATGCAAGTCGAACGGTCTTAAGCAATTAAGATA
    DHE.(pl ).seq   GATGAACGCTAGCGGCGTGCCTTATGCATGCAAGTCGAACGGTCTTAAGCAATTAAGATA
    DHE.(dll).seq   GATGAACGCTAGCGGCGTGCCTTATGCATGCAAGTCGAACGGTCTTAAGCAATTAAGATA
    DHE.(dab).seq   GATGAACGCTAGCGGCGTGCCTTATGCATGCAAGTCGAACGGTCTTAAGCAATTAAGATA
    DHE.(pin).seq   GATGAACGCTAGCGGCGTGCCTTATGCATGCAAGTCGAACGGTCTTAAGCAATTAAGATA 61                                                          120
    DHE.(cornell)   GTGGCAAACGGGTGAGTAACGCGTAAGTAACCTACCTCTAAGTGGGGGATAGCTTCGGGA
    DHE (stf).seq   GTGGCAAACGGGTGAGTAACGCGTAAGTAACCTACCTCTAAGTGGGGGATAGCTTCGGGA
    DHE.(pl ).seq   GTGGCAAACGGGTGAGTAACGCGTAAGTAACCTACCTCTAAGTGGGGGATAGCTTCGGGA
    DHE.(dll).seq   GTGGCAAACGGGTGAGTAACGCGTAAGTAACCTACCTCTAAGTGGGGGATAGCTTCGGGA
    DHE.(dab).seq   GTGGCGAACGGGTGAGTAACGCGTAAGTAACCTACCTCTAAGTGGGGGATAGCTTCGGGA
    DHE.(pin).seq   GTGGCGAACGGGTGAGTAACGCGTAAGTAACCTACCTCTAAGTGGGGGATAGCTTCGGGA 121
180
    DHE.(cornell)   AACTGAAGGTAATACCGCATGTGATGGGCTGACATAAGTCGGTTCATTAAAGCCGCAAGG
    DHE (stf).seq   AACTGAAGGTAATACCGCATGTGGTGGGCCGACATAAGTTGGTTCACTAAAGCCGTAAGG
    DHE.(pl ).seq   AACTGAAGGTAATACCGCATGTGATGGGCTGACATAAGTCGGTTCATTAAAGCCGCAAGG
    DHE.(dll).seq   AACTGAAGGTAATACCGCATGTGGTGGGCCGACATAAGTTGGTTCACTAAAGCCGTAAGG
    DHE.(dab).seq   AACTGAAGGTAATACCGCATGTGGTGGGCCGACATATGTTGGTTCACTAAAGCCGTAAGG
    DHE.(pin).seq   AACTGAAGGTAATACCGCATGTGGTGGGCCGACATATGTTGGTTCACTAAAGCCGTAAGG 181                                                         240
    DHE.(cornell)   TGCTTGGTGAGGGGCTTGCGTCCGATTAGCTAGTTGGTGGGGTAATGGTCTACCAAGGCT
    DHE (stf).seq   TGCTTGGTGAGGGGCTTGCGTCCGATTAGCTAGTTGGTGGGGTAACGGCCTACCAAGGCT
    DHE.(pl ).seq   TGCTTGGTGAGGGGCTTGCGTCCGATTAGCTAGTTGGTGGGGTAATGGCCTACCAAGGCT
    DHE.(dll).seq   TGCTTGGTGAGGGGCTTGCGTCCGATTAGCTAGTTGGTGGGGTAACGGCCTACCAAGGCT
    DHE.(dab).seq   CGCTTGGTGAGGGGCTTGCGTCCGATTAGCTAGTTGGTGGGGTAATGGCCTACCAAGGCT
    DHE.(pin).seq   CGCTTGGTGAGGGGCTTGCGTCCGATTAGCTAGTTGGTGGGGTAATGGCCTACCAAGGCT 241                                                         300
    DHE.(cornell)   TCGATCGGTAGCT.GGTCTGAGAGGATGATCAGCCACACTGGGACTGAGACACGGGCCAG
    DHE (stf).seq   TCGATCGGTAGCTTGGTCTGAGAGGATGATCAGCCACACTGGGACTGAGACACGGCCCAG
    DHE.(pl ).seq   TCGATCGGTAGCT.GGTCTGAGAGGATGATCAGCCACACTGGGACTGAGACACGGCCCAG
    DHE.(dll).seq   TCGATCGGTAGCT.GGTCTGAGAGGATGATCAGCCACACTGGGACTGAGACACGGCCCAG
    DHE.(dab).seq   TCGATCGGTAGCT.GGTCTGAGAGGATGATCAGCCACACTGGGACTGAGACACGGCCCAG
    DHE.(pin).seq   TCGATCGGTAGCT.GGTCTGAGAGGATGATCAGCCACACTGGGACTGAGACACGGCCCAG
```

```
              301                                                      360
DHE.(cornell) ACTCCTACGGGAGGCAGCAGCAAGGAATCTTGGGCAATGGGCGAAAGCCTGACCCAGCAA
DHE (stf).seq ACTCCTACGGGAGGCAGCAGCAAGGAATCTTGGGCAATGGGCGAAAGCCTGACCCAGCAA
DHE.(pl ).seq ACTCCTACGGGAGGCAGCAGCAAGGAATCTTGGGCAATGGGCGAAAGCCTGACCCAGCAA
DHE.(dll).seq ACTCCTACGGGAGGCAGCAGCAAGGAATCTTGGGCAATGGGCGAAAGCCTGACCCAGCAA
DHE.(dab).seq ACTCCTACGGGAGGCAGCAGCAAGGAATCTTGGGCAATGGGCGAAAGCCTGACCCAGCAA
DHE.(pin).seq ACTCCTACGGGAGGCAGCAGCAAGGAATCTTGGGCAATGGGCGAAAGCCTGACCCAGCAA 361                                                      420
DHE.(cornell) CGCCGCGTGAGGGATGAAGGCTTTCGGGTTGTAAACCTCTTTTCACAGGGAAGAATAATG
DHE (stf).seq CGCCGCGTGAGGGATGAAGGCTCTCGGGTTGTAAACCTCTTTTCACAGGGAAGAATAATG
DHE.(pl ).seq CGCCGCGTGAGGGATGAAGGCTTTCGGGTTGTAAACCTCTTTTCACAGGGAAGAATAATG
DHE.(dll).seq CGCCGCGTGAGGGATGAAGGCTCTCGGGTTGTAAACCTCTTTTCACAGGGAAGAATAATG
DHE.(dab).seq CGCCGCGTGAGGGATGAAGGCTTTCGGGTTGTAAACCTCTTTTCATAGGGAAGAATAATG
DHE.(pin).seq CGCCGCGTGAGGGATGAAGGCTTTCGGGTTGTAAACCTCTTTTCATAGGGAAGAATAATG 421                                                      480
DHE.(cornell) ACGGTACCTGTGGAATAAGCTTCGGCTAACTACGTGCCAGCAGCCGCGGTAATACGTAGG
DHE (stf).seq ACGGTACCTGTGGAATAAGCTTCGGCTAACTACGTGCCAGCAGCCGCGGTAATACGTAGG
DHE.(pl ).seq ACGGTACCTGTGGAATAAGCTTCGGCTAACTACGTGCCAGCAGCCGCGGTAATACGTAGG
DHE.(dll).seq ACGGTACCTGTGGAATAAGCTTCGGCTAACTACGTGCCAGCAGCCGCGGTAATACGTAGG
DHE.(dab).seq ACGGTACCTGTGGAATAAGCTTCGGCTAACTACGTGCCAGCAGCCGCGGTAATACGTAGG
DHE.(pin).seq ACGGTACCTGTGGAATAAGCTTCGGCTAACTACGTGCCAGCAGCCGCGGTAATACGTAGG 481                                                      540
DHE.(cornell) GAAGCAAGCGTTATCCGGATTTATTGGGCGTAAAGTGAGCGTAGGTGGTCTTTCAAGTTG
DHE (stf).seq .AAGCAAGCGTTATCCGGATTTATTGGGCGTAAAGTGAGCGTAGGTGGTCTTTCAAGTTG
DHE.(pl ).seq .AAGCAAGCGTTATCCGGATTTATTGGGCGTAAAGTGAGCGTAGGTGGTCTTTCAAGTTG
DHE.(dll).seq .AAGCAAGCGTTATCCGGATTTATTGGGCGTAAAGTGAGCGTAGGTGGTCTTTCAAGTTG
DHE.(dab).seq .AAGCAAGCGTTATCCGGATTTATTGGGCGTAAAGTGAGCGTAGGTGGTCTTTCAAGTTG
DHE.(pin).seq .AAGCAAGCGTTATCCGGATTTATTGGGCGTAAAGTGAGCGTAGGTGGTCTTTCAAGTTG 541                                                      600
DHE.(cornell) GATGTGAAATTTCCCGGCTTAACCGGGACGTGTCATTCAATACTGTTGGACTAGAGTACA
DHE (stf).seq GATGTGAAATTTCCCGGCTTAACCGGGACGTGTCATTCAATACTGTTGGACTAGAGTACA
DHE.(pl ).seq GATGTGAAATTTCCCGGCTTAACCGGGACGTGTCATTCAATACTGTTGGACTAGAGTACA
DHE.(dll).seq GATGTGAAATTTCCCGGCTTAACCGGGACGTGTCATTCAATACTGTTGGACTAGAGTACA
DHE.(dab).seq GATGTGAAATTTCCCGGCTTAACCGGGACGAGTCATTCAATACTGTTGGACTAGAGTACA
DHE.(pin).seq GATGTGAAATTTCCCGGCTTAACCGGGACGAGTCATTCAATACTGTTGGACTAGAGTACA 601                                                      660
DHE.(cornell) GCAGGAGAAAACGGAATTCCCGGTGTAGTGGTAAAATGCGTAGATATCGGGAGGAACACC
DHE (stf).seq GCAGGAGAAAACGGAATTCCCGGTGTAGTGGTAAAATGCGTAGATATCGGGAGGAACACC
DHE.(pl ).seq GCAGGAGAAAACGGAATTCCCGGTGTAGTGGTAAAATGCGTAGATATCGGGAGGAACACC
DHE.(dll).seq GCAGGAGAAAACGGAATTCCCGGTGTAGTGGTAAAATGCGTAGATATCGGGAGGAACACC
DHE.(dab).seq GCAGGAGAAAACGGAATTCCCGGTGTAGTGGTAAAATGCGTAGATATCGGGAGGAACACC
DHE.(pin).seq GCAGGAGAAAACGGAATTCCCGGTGTAGTGGTAAAATGCGTAGATATCGGGAGGAACACC 661                                                      720
DHE.(cornell) AGAGGCGAAGGCGGTTTTCTAGGTTGTCACTGACACTGAGGCTCGAAAGCGTGGGGAGCG
DHE (stf).seq AGAGGCGAAGGCGGTTTTCTAGGTTGTCACTGACACTGAGGCTCGAAAGCGTGGGGAGCG
DHE.(pl ).seq AGAGGCGAAGGCGGTTTTCTAGGTTGTCACTGACACTGAGGCTCGAAAGCGTGGGGAGCG
DHE.(dll).seq AGAGGCGAAGGCGGTTTTCTAGGTTGTCACTGACACTGAGGCTCGAAAGCGTGGGGAGCG
DHE.(dab).seq AGAGGCGAAGGCGGTTTTCTAGGTTGTCACTGACACTGAGGCTCGAAAGCGTGGGGAGCG
DHE.(pin).seq AGAGGCGAAGGCGGTTTTCTAGGTTGTCACTGACACTGAGGCTCGAAAGCGTGGGGAGCG 721                                                      780
DHE.(cornell) AACAGAATTAGATACTCTGGTAGTCCACGCCTTAAACTATGGACACTAGGTATAGGGAGT
DHE (stf).seq AACAGAATTAGATACTCTGGTAGTCCACGCCTTAAACTATGGACACTAAGTATAGGGAGT
```

```
               DHE.(pl ).seq   AACAGAATTAGATACTCTGGTAGTCCACGCCTTAAACTATGGACACTAGGTATAGGGAGT
               DHE.(dll).seq   AACAGAATTAGATACTCTGGTAGTCCACGCCTTAAACTATGGACACTAGGTATAGGGAGT
               DHE.(dab).seq   AACAGAATTAGATACTCTGGTAGTCCACGCCTTAAACTATGGACACTAGGTATAGGGAGT
               DHE.(pin).seq   AACAGAATTAGATACTCTGGTAGTCCACGCCTTAAACTATGGACACTAGGTATAGGGAGT 781                                                          840
               DHE.(cornell)   ATCGACCCTCTCTGTGCCGAAGCTAACGCTTTAAGTGTCCCGCCTGGGGAGTACGGTCGC
               DHE (stf).seq   ATCGACCCTCTCTGTGCCGAAGCTAACGCTTTAAGTGTCCCGCCTGGGGAGTACGGTCGC
               DHE.(pl ).scq   ATCGACCCTCTCTGTGCCGAAGCTAACGCTYTAAGTGTCCCGCCTGGGGAGTACGGTCGC
               DHE.(dll).seq   ATCGACCCTCTCTGTGCCGAAGCTAACGCTTTAAGTGTCCCGCCTGGGGAGTACGGTCGC
               DHE.(dab).seq   ATCGACCCTCTCTGTGCCGAAGCTAACGCTTTAAGTGTCCCGCCTGGGGAGTACGGTCGC
               DHE.(pin).seq   ATCGACCCTCTCTGTGCCGAAGCTAACGCTTTAAGTGTCCCGCCTGGGGAGTACGGTCGC 841                                                          900
               DHE.(cornell)   AAGGCTAAAACTCAAAGGAATTGACGGGGGCCCGCACAAGCAGCGGAGCGTGTGGTTTAA
               DHE (stf).seq   AAGGCTAAAACTCAAAGGAATTGACGGGGGCCCGCACAAGCAGCGGAGCGTGTGGTTTAA
               DHE.(pl ).seq   AAGGCTAAAACTCAAAGGAATTGACGGGGGCCCTTACAAGCAGCGGAGCGTGTGGTTTAA
               DHE.(dll).seq   AAGGCTAAAACTCAAAGGAATTGACGGGGGCCCGCACAAGCAGCGGAGCGTGTGGTTTAA
               DHE.(dab).seq   AAGGCTAAAACTCAAAGGAATTGACGGGGGCCCGCACAAGCAGCGGAGCGTGTGGTTTAA
               DHE.(pin).seq   AAGGCTAAAACTCAAAGGAATTGACGGGGGCCCGCACAAGCAGCGGAGCGTGTGGTTTAA 901                                                          960
               DHE.(cornell)   TTCGATGCTACACGAAGAAC.TTACCAAGATTTGACATGCATGAAGTAGTGAACCGAAAG
               DHE (stf).seq   TTCGATGCTACACGAAGAACCTTACCAAGATTTGACATGCATGAAGTAGTGAACCGAAAG
               DHE.(pl ).seq   TTCGATGCTACACGAAGAACCTTACCAAGATTTGACATGCATGAAGTAGTGAACCGAAAG
               DHE.(dll).seq   TTCGATGCTACACGAAGAACCTTACCAAGATTTGACATGCATGAAGTAGTGAACCGAAAG
               DHE.(dab).seq   TTCGATGCTACACGAAGAACCTTACCAAGATTTGACATGCATGTAGTAGTGAACTGAAAG
               DHE.(pin).seq   TTCGATGCTACACGAAGAACCTTACCAAGATTTGACATGCATGTAGTAGTGAACTGAAAG 961                                                         1020
               DHE.(cornell)   GGAAACGACCTGTTAAGTCAGGAGTTTGCACAGGTGCTGCATGGCTGTCGTCAGCTCGTG
               DHE (stf).seq   GGAAACGACCTGTTAAGTCAGGAGTTTGCACAGGTGCTGCATGGCTGTCGTCAGCTCGTG
               DHE.(pl ).seq   GGAAACGACCTGTTAAGTCAGGAGTTTGCACAGGTGCTGCATGGCTGTCGTCAGCTCGTG
               DHE.(dll).seq   GGAAACGACCTGTTAAGTCAGGAGTTTGCACAGGTGCTGCATGGCTGTCGTCAGCTCGTG
               DHE.(dab).seq   GGGAACGACCTGTTAAGTCAGGAACTTGCACAGGTGCTGCATGGCTGTCGTCAGCTCGTG
               DHE.(pin).seq   GGGAACGACCTGTTAAGTCAGGAACTTGCACAGGTGCTGCATGGCTGTCGTCAGCTCGTG 1021                                                        1080
               DHE.(cornell)   CCGTGAGGTGTTGGGTTAAGTCCTGCAACGAGCGCAACC.TTGTTGCTAGTTAAATTTTC
               DHE (stf).seq   CCGTGAGGTGTTTGGTTAAGTCCTGCAACGAGCGCAACCCTTGTTGCTAGTTAAATTTTC
               DHE.(pl ).seq   CCGTGAGGTGTTTGGTTAAGTCCTGCAACGAGCGCAACCCTTGTTGCTAGTTAAATTTTC
               DHE.(dll).seq   CCGTGAGGTGTTTGGTTAAGTCCTGCAACGAGCGCAACCCTTGTTGCTAGTTAAATTTTC
               DHE.(dab).seq   CCGTGAGGTGTTTGGTTAAGTCCTGCAACGAGCGCAACCCTTGTTGCTAGTTAAATTTTC
               DHE.(pin).seq   CCGTGAGGTGTTTGGTTAAGTCCTGCAACGAGCGCAACCCTTGTTGCTAGTTAAATTTTC 1081                                                        1140
               DHE.(cornell)   TAGCGAGACTAGCGAGACTGCCCCGCGAAACGGGGAGGAAGGTGGGGATGACGTCAAGTC
               DHE (stf).seq   TAGCGAG.........ACTGCCCCGCGAAACGGGGAGGAAGGTGGGGATGACGTCAAGTC
               DHE.(pl ).seq   TAGCGAG.........ACTGCCCCGCGAAACGGGGAGGAAGGTGGGGATGACGTCAAGTC
               DHE.(dll).seq   TAGCGAG.........ACTGCCCCGCGAAACGGGGAGGAAGGTGGGGATGACGTCAAGTC
               DHE.(dab).seq   TAGCGAG.........ACTGCCCCGCGAAACGGGGAGGAAGGTGGGGATGACGTCAAGTC
               DHE.(pin).seq   TAGCGAG.........ACTGCCCCGCGAAACGGGGAGGAAGGTGGGGATGACGTCAAGTC
```

```
              1141                                                        1200
DHE.(cornell) AGCATGGCCTTTATATCTTGGGCTACACACACGCTACAATGGACAGAACAATAGGTTGCA
DHE (stf).seq AGCATGGCCTTTATATCTTGGGCTACACACACGCTACAATGGACAGAACAATAGGTTGCA
DHE.(pl ).seq AGCATGGCCTTTATATCTTGGGCTACACACACGCTACAATGGACAGAACAATAGGTTGCA
DHE.(dll).seq AGCATGGCCTTTATATCTTGGGCTACACACACGCTACAATGGACAGAACAATAGGTTGCA
DHE.(dab).seq AGCATGGCCTTTATATCTTGGGCTACACACACGCTACAATGGACAGAACAATAGGTTGCA
DHE.(pin).seq AGCATGGCCTTTATATCTTGGGCTACACACACGCTACAATGGACAGAACAATAGGTTGCA 1201                                                        1260
DHE.(cornell) ACAGTGTGAACTGGAGCTAATCCCCAAAGCTGTCCTCAGTTCGGATTGCAGGCTGAAACC
DHE (stf).seq ACAGTGTGAACTGGAGCTAATCCTCAAAGCTGTCCTCAGTTCGGATTGCAGGCTGAAACC
DHE.(pl ).seq ACAGTGTGAACTGGAGCTAATCCCCAAAGCTGTCCTCAGTTCGGATTGCAGGCTGAAACC
DHE.(dll).seq ACAGTGTGAACTGGAGCTAATCCTCAAAGCTGTCCTCAGTTCGGATTGCAGGCTGAAACC
DHE.(dab).seq ACAGTGTGAACTGGAGCTAATCCCCAAAGCTGTCCTCAGTTCGGATTGCAGGCTGAAACC
DHE.(pin).seq ACAGTGTGAACTGGAGCTAATCCCCAAAGCTGTCCTCAGTTCGGATTGCAGGCTGAAACC 1261                                                        1320
DHE.(cornell) CGCCTGCATGAAGTTGGAGTTGCTAGTAACCGCATATCAGCAAGGTGCGGTGAATACGTT
DHE (stf).seq CGCCTGCATGAAGTTGGAGTTGCTAGTAACCGCATATCAGCAAGGTGCGGTGAATACGTT
DHE.(pl ).seq CGCCTGCATGAAGTTGGAGTTGCTAGTAACCGCATATCAGCAAGGTGCGGTGAATACGTT
DHE.(dll).seq CGCCTGCATGAAGTTGGAGTTGCTAGTAACCGCATATCAGCAAGGTGCGGTGAATACGTT
DHE.(dab).seq CGCCTGCATGAAGTTGGAGTTGCTAGTAACCGCATATCAGCATGGTGCGGTGAATACGTT
DHE.(pin).seq CGCCTGCATGAAGTTGGAGTTGCTAGTAACCGCATATCAGCATGGTGCGGTGAATACGTT 1321                                                        1380
DHE.(cornell) CTCGGGCCTTGTACACACCGCCCGTCACGTCATGANAGCCGGTAACACTTGAAGTCGATG
DHE (stf).seq CTCGGGCCTTGTACACACCGCCCGTCACGTCATGAAAGCCGGTAACACTTGAAGTCGATG
DHE.(pl ).seq CTCGGGCCTTGTACACACCGCCCGTCACGTCATGAAAGCCGGTAACACTTGAAGTCGATG
DHE.(dll).seq CTCGGGCCTTGTACACACCGCCCGTCACGTCATGAAAGCCGGTAACACTTGAAGTCGATG
DHE.(dab).seq CTCGGGCCTTGTACACACCGCCCGTCACGTCATGAAAGCCGGTAACACTTGAAGTCGATG
DHE.(pin).seq CTCGGGCCTTGTACACACCGCCCGTCACGTCATGAAAGCCGGTAACACTTGAAGTCGATG 1381                                                        1440
DHE.(cornell) TGCCAACCGCAAGGAGGCAGTCGCCGAGGGTGGGACTGGTAATTGGGACGAAGTCGTAAC
DHE (stf).seq TGCCAACC....................................................
DHE.(pl ).seq TGCCAACC....................................................
DHE.(dll).seq TGCCAACC....................................................
DHE.(dab).seq TGCCAACC....................................................
DHE.(pin).seq TGCCAACC....................................................

1441   1446
DHE.(cornell) AAGGTA (SEQ ID NO:7)
DHE (stf).seq ...... (SEQ ID NO:3)
DHE.(pl ).seq ...... (SEQ ID NO:2)
DHE.(dll).seq ...... (SEQ ID NO:6)
DHE.(dab).seq ...... (SEQ ID NO:4)
DHE.(pin).seq ...... (SEQ ID NO:5)
```

FIGURE 2 The *Dehalococcoides sp.* alignment with *E. coli*

```
12/10/98BEcAlignmentG.msf  MSF: 1576   Type: D Tuesday, December 15, 1998 Check: 3955
..
Name: E.coli.16S              Len: 1542
Name: DHE.(cornell)           Len: 1443
Name: DHE (Stf).seq           Len: 1386
Name: DHE.(pl ).seq           Len: 1385
Name: DHE.(dab).seq           Len: 1385
Name: DHE.(pin).seq           Len: 1385
Name: DHE.(dll).seq           Len: 1385
//
                         1                                                          60
         E.coli.16S seq  AAATTGAAGAGTTTGATCATGGCTCAGATTGAACGCTGGCGGCAGGCCTAACACATGCAA
         DHE.(cornell)   ........................GATGAACGCTAGCGGCGTGCCTTATGCATGCAA
         DHE.(Stf).seq   ........................GATGAACGCTAGCGGCGTGCCTTATGCATGCAA
         DHE.(pl ).seq   ........................GATGAACGCTAGCGGCGTGCCTTATGCATGCAA
         DHE.(dab).seq   ........................GATGAACGCTAGCGGCGTGCCTTATGCATGCAA
         DHE.(pin).seq   ........................GATGAACGCTAGCGGCGTGCCTTATGCATGCAA
         DHE.(dll).seq   ........................GATGAACGCTAGCGGCGTGCCTTATGCATGCAA 61                                                         120
         E.coli.16S seq  GTCGAACGGTAACAGGAAGAAGCTTGCTTCTTTGCTGACGAGTGGCGGACGGGTGAGTAA
         DHE.(cornell)   GTCGAACGGTCTTAAGCAA....TTAA.........GAT.AGTGGCAAACGGGTGAGTAA
         DHE.(Stf).seq   GTCGAACGGTCTTAAGCAA....TTAA.........GAT.AGTGGCAAACGGGTGAGTAA
         DHE.(pl ).seq   GTCGAACGGTCTTAAGCAA....TTAA.........GAT.AGTGGCAAACGGGTGAGTAA
         DHE.(dab).seq   GTCGAACGGTCTTAAGCAA....TTAA.........GAT.AGTGGCGAACGGGTGAGTAA
         DHE.(pin).seq   GTCGAACGGTCTTAAGCAA....TTAA.........GAT.AGTGGCGAACGGGTGAGTAA
         DHE.(dll).seq   GTCGAACGGTCTTAAGCAA....TTAA.........GAT AGTGGCAAACGGGTGAGTAA 121                                                        179
         E.coli.16S seq  TGTCTGGGAAAC.TGCCTGATGGAGGGGGATAACTACTGGAAACGGTAGCTAATACCGCA
         DHE.(cornell)   CGCGTAAGTAACCTACCTCTAAGTGGGGGATAGCTTCGGGAAACTGAAGGTAATACCGCA
         DHE.(Stf).seq   CGCGTAAGTAACCTACCTCTAAGTGGGGGATAGCTTCGGGAAACTGAAGGTAATACCGCA
         DHE.(pl ).seq   CGCGTAAGTAACCTACCTCTAAGTGGGGGATAGCTTCGGGAAACTGAAGGTAATACCGCA
         DHE.(dab).seq   CGCGTAAGTAACCTACCTCTAAGTGGGGGATAGCTTCGGGAAACTGAAGGTAATACCGCA
         DHE.(pin).seq   CGCGTAAGTAACCTACCTCTAAGTGGGGGATAGCTTCGGGAAACTGAAGGTAATACCGCA
         DHE.(dll).seq   CGCGTAAGTAACCTACCTCTAAGTGGGGGATAGCTTCGGGAAACTGAAGGTAATACCGCA 180                                                        236
         E.coli.16S seq  TAACGTCGCAAGACCAAAGAGGGGGACCTTCGGGCCTCTTGCCATCGGATGTG...CCCA
         DHE.(cornell)   TGTGATGGGCTGAC.ATAAGTCGGTTCATTAAAGCCGCAAGGTGCTTGGTGAGGGGCTTG
         DHE.(Stf).seq   TGTGGTGGGCCGAC.ATAAGTTGGTTCACTAAAGCCGTAAGGTGCTTGGTGAGGGGCTTG
         DHE.(pl ).seq   TGTGATGGGCTGAC.ATAAGTCGGTTCATTAAAGCCGCAAGGTGCTTGGTGAGGGGCTTG
         DHE.(dab).seq   TGTGGTGGGCCGAC.ATATGTTGGTTCACTAAAGCCGTAAGGCGCTTGGTGAGGGGCTTG
         DHE.(pin).seq   TGTGGTGGGCCGAC.ATATGTTGGTTCACTAAAGCCGTAAGGCGCTTGGTGAGGGGCTTG
         DHE.(dll).seq   TGTGGTGGGCCGAC.ATAAGTTGGTTCACTAAAGCCGTAAGGTGCTTGGTGAGCGGCTTG 237                                                        295
         E.coli.16S seq  GATGGGATTAGCTAGTAGGTGGGGTAACGGCTCACCTAGGCGACGATCCCTAGCT.GGTC
         DHE.(cornell)   CGTCCGATTAGCTAGTTGGTGGGGTAATGGTCTACCAAGGCTTCGATCGGTAGCT.GGTC
         DHE.(Stf).seq   CGTCCGATTAGCTAGTTGGTGGGGTAACGGCCTACCAAGGCTTCGATCGGTAGCTTGGTC
         DHE.(pl ).seq   CGTCCGATTAGCTAGTTGGTGGGGTAATGGCCTACCAAGGCTTCGATCGGTAGCT.GGTC
         DHE.(dab).seq   CGTCCGATTAGCTAGTTGGTGGGGTAATGGCCTACCAAGGCTTCGATCGGTAGCT.GGTC
         DHE.(pin).seq   CGTCCGATTAGCTAGTTGGTGGGGTAATGGCCTACCAAGGCTTCGATCGGTAGCT.GGTC
         DHE.(dll).seq   CGTCCGATTAGCTAGTTGGTGGGGTAACGGCCTACCAAGGCTTCGATCGGTAGCT.GGTC
```

```
                        296                                                              355
E.coli.16S seq      TGAGAGGATGACCAGCCACACTGGAACTGAGACACGGTCCAGACTCCTACGGGAGGCAGC
DHE.(cornell)       TGAGAGGATGATCAGCCACACTGGGACTGAGACACGGGCCAGACTCCTACGGGAGGCAGC
DHE.(Stf).seq       TGAGAGGATGATCAGCCACACTGGGACTGAGACACGGCCCAGACTCCTACGGGAGGCAGC
DHE.(pl ).seq       TGAGAGGATGATCAGCCACACTGGGACTGAGACACGGCCCAGACTCCTACGGGAGGCAGC
DHE.(dab).seq       TGAGAGGATGATCAGCCACACTGGGACTGAGACACGGCCCAGACTCCTACGGGAGGCAGC
DHE.(pin).seq       TGAGAGGATGATCAGCCACACTGGGACTGAGACACGGCCCAGACTCCTACGGGAGGCAGC
DHE.(dll).seq       TGAGAGGATGATCAGCCACACTGGGACTGAGACACGGCCCAGACTCCTACGGGAGGCAGC 356                                                              415
E.coli.16S seq      AGTGGGGAATATTGCACAATGGGCGCAAGCCTGATGCAGCCATGCCGCGTGTATGAAGAA
DHE.(cornell)       AGCAAGGAATCTTGGGCAATGGGCGAAAGCCTGACCCAGCAACGCCGCGTGAGGGATGAA
DHE.(Stf).seq       AGCAAGGAATCTTGGGCAATGGGCGAAAGCCTGACCCAGCAACGCCGCGTGAGGGATGAA
DHE.(pl ).seq       AGCAAGGAATCTTGGGCAATGGGCGAAAGCCTGACCCAGCAACGCCGCGTGAGGGATGAA
DHE.(dab).seq       AGCAAGGAATCTTGGGCAATGGGCGAAAGCCTGACCCAGCAACGCCGCGTGAGGGATGAA
DHE.(pin).seq       AGCAAGGAATCTTGGGCAATGGGCGAAAGCCTGACCCAGCAACGCCGCGTGAGGGATGAA
DHE.(dll).seq       AGCAAGGAATCTTGGGCAATGGGCGAAAGCCTGACCCAGCAACGCCGCGTGAGGGATGAA 416                                                              475
E.coli.16S seq      GGCCTTCGGGTTGTAAAGTACTTTCAGCGGGGAGGAAGGGAGTAAAGTTAATACCTTTGC
DHE.(cornell)       GGCTTTCGGGTTGTAAACCTCTTTTCACAGGGAAGAA..........TAAT........
DHE.(Stf).seq       GGCTCTCGGGTTGTAAACCTCTTTTCACAGGGAAGAA..........TAAT........
DHE.(pl ).seq       GGCTTTCGGGTTGTAAACCTCTTTTCACAGGGAAGAA..........TAAT........
DHE.(dab).seq       GGCTTTCGGGTTGTAAACCTCTTTTCATAGGGAAGAA..........TAAT........
DHE.(pin).seq       GGCTTTCGGGTTGTAAACCTCTTTTCATAGGGAAGAA..........TAAT........
DHE.(dll).seq       GGCTCTCGGGTTGTAAACCTCTTTTCACAGGGAAGAA..........TAAT........

476                                                              535
E.coli.16S seq      TCATTGACGTTACCCGCAGAAGAAGCACCGGCTAACTCCGTGCCAGCAGCCGCGGTAATA
DHE.(cornell)       .....GACGGTACCTGTGGAATAAGCTTCGGCTAACTACGTGCCAGCAGCCGCGGTAATA
DHE.(Stf).seq       .....GACGGTACCTGTGGAATAAGCTTCGGCTAACTACGTGCCAGCAGCCGCGGTAATA
DHE.(pl ).seq       .....GACGGTACCTGTGGAATAAGCTTCGGCTAACTACGTGCCAGCAGCCGCGGTAATA
DHE.(dab).seq       .....GACGGTACCTGTGGAATAAGCTTCGGCTAACTACGTGCCAGCAGCCGCGGTAATA
DHE.(pin).seq       .....GACGGTACCTGTGGAATAAGCTTCGGCTAACTACGTGCCAGCAGCCGCGGTAATA
DHE.(dll).seq       .....GACGGTACCTGTGGAATAAGCTTCGGCTAACTACGTGCCAGCAGCCGCGGTAATA 536                                                              594
E.coli.16S seq      CGGAGGGT.GCAAGCGTTAATCGGAATTACTGGGCGTAAAGCGCACGCAGGCGGTTTGTT
DHE.(cornell)       CGTAGGGAAGCAAGCGTTATCCGGATTTATTGGGCGTAAAGTGAGCGTAGGTGGTCTTTC
DHE.(Stf).seq       CGTAGG.AAGCAAGCGTTATCCGGATTTATTGGGCGTAAAGTGAGCGTAGGTGGTCTTTC
DHE.(pl ).seq       CGTAGG.AAGCAAGCGTTATCCGGATTTATTGGGCGTAAAGTGAGCGTAGGTGGTCTTTC
DHE.(dab).seq       CGTAGG.AAGCAAGCGTTATCCGGATTTATTGGGCGTAAAGTGAGCGTAGGTGGTCTTTC
DHE.(pin).seq       CGTAGG.AAGCAAGCGTTATCCGGATTTATTGGGCGTAAAGTGAGCGTAGGTGGTCTTTC
DHE.(dll).seq       CGTAGG.AAGCAAGCGTTATCCGGATTTATTGGGCGTAAAGTGAGCGTAGGTGGTCTTTC 595                                                              654
E.coli.16S seq      AAGTCAGATGTGAAATCCCCGGGCTCAACCTGGGAACTGCATCTGATACTGGCAAGCTTG
DHE.(cornell)       AAGTTGGATGTGAAATTTCCCGGCTTAACCGGACGTGTCATTCAATACTGTTGGACTAG
DHE.(Stf).seq       AAGTTGGATGTGAAATTTCCCGGCTTAACCGGACGTGTCATTCAATACTGTTGGACTAG
DHE.(pl ).seq       AAGTTGGATGTGAAATTTCCCGGCTTAACCGGACGTGTCATTCAATACTGTTGGACTAG
DHE.(dab).seq       AAGTTGGATGTGAAATTTCCCGGCTTAACCGGACGAGTCATTCAATACTGTTGGACTAG
DHE.(pin).seq       AAGTTGGATGTGAAATTTCCCGGCTTAACCGGACGAGTCATTCAATACTGTTGGACTAG
DHE.(dll).seq       AAGTTGGATGTGAAATTTCCCGGCTTAACCGGACGTGTCATTCAATACTGTTGGACTAG 655                                                              714
E.coli.16S seq      AGTCTCGTAGAGGGGGGTAGAATTCCAGGTGTAGCGGTGAAATGCGTAGAGATCTGGAGG
DHE.(cornell)       AGTACAGCAGGAGAAAACGGAATTCCCGGTGTAGTGGTAAAATGCGTAGATATCGGGAGG
DHE.(Stf).seq       AGTACAGCAGGAGAAAACGGAATTCCCGGTGTAGTGGTAAAATGCGTAGATATCGGGAGG
DHE.(pl ).seq       AGTACAGCAGGAGAAAACGGAATTCCCGGTGTAGTGGTAAAATGCGTAGATATCGGGAGG
```

```
DHE.(dab).seq   AGTACAGCAGGAGAAAACGGAATTCCCGGTGTAGTGGTAAAATGCGTAGATATCGGGAGG
DHE.(pin).seq   AGTACAGCAGGAGAAAACGGAATTCCCGGTGTAGTGGTAAAATGCGTAGATATCGGGAGG
DHE.(dll).seq   AGTACAGCAGGAGAAAACGGAATTCCCGGTGTAGTGGTAAAATGCGTAGATATCGGGAGG 715                                                        774
E.coli.16S seq  AATACCGGTGGCGAAGGCGGCCCCCTGGACGAAGACTGACGCTCAGGTGCGAAAGCGTGG
DHE.(cornell)   AACACCAGAGGCGAAGGCGGTTTTCTAGGTTGTCACTGACACTGAGGCTCGAAAGCGTGG
DHE.(Stf).seq   AACACCAGAGGCGAAGGCGGTTTTCTAGGTTGTCACTGACACTGAGGCTCGAAAGCGTGG
DHE.(pl ).seq   AACACCAGAGGCGAAGGCGGTTTTCTAGGTTGTCACTGACACTGAGGCTCGAAAGCGTGG
DHE.(dab).seq   AACACCAGAGGCGAAGGCGGTTTTCTAGGTTGTCACTGACACTGAGGCTCGAAAGCGTGG
DHE.(pin).seq   AACACCAGAGGCGAAGGCGGTTTTCTAGGTTGTCACTGACACTGAGGCTCGAAAGCGTGG
DHE.(dll).seq   AACACCAGAGGCGAAGGCGGTTTTCTAGGTTGTCACTGACACTGAGGCTCGAAAGCGTGG 755                                                        834
E.coli.16S seq  GGAGCAAACAGGATTAGATACCCTGGTAGTCCACGCCGTAAACGATGTCGACTTGGAGGT
DHE.(cornell)   GGAGCGAACAGAATTAGATACTCTGGTAGTCCACGCCTTAAACTATGGACACTAGGTATA
DHE.(Stf).seq   GGAGCGAACAGAATTAGATACTCTGGTAGTCCACGCCTTAAACTATGGACACTAAGTATA
DHE.(pl ).seq   GGAGCGAACAGAATTAGATACTCTGGTAGTCCACGCCTTAAACTATGGACACTAGGTATA
DHE.(dab).seq   GGAGCGAACAGAATTAGATACTCTGGTAGTCCACGCCTTAAACTATGGACACTAGGTATA
DHE.(pin).seq   GGAGCGAACAGAATTAGATACTCTGGTAGTCCACGCCTTAAACTATGGACACTAGGTATA
DHE.(dll).seq   GGAGCGAACAGAATTAGATACTCTGGTAGTCCACGCCTTAAACTATGGACACTAGGTATA 835                                                        893
E.coli.16S seq  TGTGCCCTTGAGGCGTGGCTT.CCGGAGCTAACGCGTTAAGTCGACCGCCTGGGGAGTAC
DHE.(cornell)   GGGAGTATCGACCCTCTCTGTGCCGAAGCTAACGCTTTAAGTGTCCCGCCTGGGGAGTAC
DHE.(Stf).seq   GGGAGTATCGACCCTCTCTGTGCCGAAGCTAACGCTTTAAGTGTCCCGCCTGGGGAGTAC
DHE.(pl ).seq   GGGAGTATCGACCCTCTCTGTGCCGAAGCTAACGCTTTAAGTGTCCCGCCTGGGGAGTAC
DHE.(dab).seq   GGGAGTATCGACCCTCTCTGTGCCGAAGCTAACGCTTTAAGTGTCCCGCCTGGGGAGTAC
DHE.(pin).seq   GGGAGTATCGACCCTCTCTGTGCCGAAGCTAACGCTTTAAGTGTCCCGCCTGGGGAGTAC
DHE.(dll).seq   GGGAGTATCGACCCTCTCTGTGCCGAAGCTAACGCTTTAAGTGTCCCGCCTGGGGAGTAC 901                                                        953
E.coli.16S seq  GGCCGCAAGGTTAAAACTCAAATGAATTGACGGGGGCCCGCACAAGCGGTGGAGCATGTG
DHE.(cornell)   GGTCGCAAGGCTAAAACTCAAAGGAATTGACGGGGGCCCGCACAAGCAGCGGAGCGTGTG
DHE.(Stf).seq   GGTCGCAAGGCTAAAACTCAAAGGAATTGACGGGGGCCCGCACAAGCAGCGGAGCGTGTG
DHE.(pl ).seq   GGTCGCAAGGCTAAAACTCAAAGGAATTGACGGGGGCCCTTACAAGCAGCGGAGCGTGTG
DHE.(dab).seq   GGTCGCAAGGCTAAAACTCAAAGGAATTGACGGGGGCCCGCACAAGCAGCGGAGCGTGTG
DHE.(pin).seq   GGTCGCAAGGCTAAAACTCAAAGGAATTGACGGGGGCCCGCACAAGCAGCGGAGCGTGTG
DHE.(dll).seq   GGTCGCAAGGCTAAAACTCAAAGGAATTGACGGGGGCCCGCACAAGCAGCGGAGCGTGTG 954                                                       1011
E.coli.16S seq  GTTTAATTCGATGCAACGCGAAGAACCTTACCTGGTCTTGACATCCACGGA..AGTTTTC
DHE.(Stf).seq   GTTTAATTCGATGCTACACGAAGAACCTTACCAAGATTTGACATGCATGAAGTAGTGAAC
DHE.(pl ).seq   GTTTAATTCGATGCTACACGAAGAACCTTACCAAGATTTGACATGCATGAAGTAGTGAAC
DHE.(dab).seq   GTTTAATTCGATGCTACACGAAGAACCTTACCAAGATTTGACATGCATGTAGTAGTGAAC
DHE.(pin).seq   GTTTAATTCGATGCTACACGAAGAACCTTACCAAGATTTGACATGCATGTAGTAGTGAAC
DHE.(dll).seq   GTTTAATTCGATGCTACACGAAGAACCTTACCAAGATTTGACATGCATGAAGTAGTGAAC 1012                                                      1068
E.coli.16S seq  AGAGATGAGAATGTGCCTTCGGG...AACCGTGAG.ACAGGTGCTGCATGGCTGTCGTCAG
DHE.(cornell)   CGAAAGGGAAACGACCTGTTAAGTCAGGAGTTTGCACAGGTGCTGCATGGCTGTCGTCAG
DHE.(Stf).seq   CGAAAGGGAAACGACCTGTTAAGTCAGGAGTTTGCACAGGTGCTGCATGGCTGTCGTCAG
DHE.(pl ).seq   CGAAAGGGAAACGACCTGTTAAGTCAGGAGTTTGCACAGGTGCTGCATGGCTGTCGTCAG
DHE.(dab).seq   TGAAAGGGGAACGACCTGTTAAGTCAGGAACTTGCACAGGTGCTGCATGGCTGTCGTCAG
DHE.(pin).seq   TGAAAGGGGAACGACCTGTTAAGTCAGGAACTTGCACAGGTGCTGCATGGCTGTCGTCAG
DHE.(dll).seq   CGAAAGGGAAACGACCTGTTAAGTCAGGAGTTTGCACAGGTGCTGCATGGCTGTCGTCAG 1069                                                      1128
E.coli.16S seq  CTCGTGTTGTGAAATGTTGGGTTAAGTCCCGCAACGAGCGCAACCCTTATCCTTTGTTGC
```

```
DHE.(cornell)  CTCGTGCCGTGAGGTGTTGGGTTAAGTCCTGCAACGAGCGCAACC.TTGTTGCTAGTTA.
DHE.(Stf).seq  CTCGTGCCGTGAGGTGTTTGGTTAAGTCCTGCAACGAGCGCAACCCTTGTTGCTAGTTA.
DHE.(pl ).seq  CTCGTGCCGTGAGGTGTTTGGTTAAGTCCTGCAACGAGCGCAACCCTTGTTGCTAGTTA.
DHE.(dab).seq  CTCGTGCCGTGAGGTGTTTGGTTAAGTCCTGCAACGAGCGCAACCCTTGTTGCTAGTTA.
DHE.(pin).seq  CTCGTGCCGTGAGGTGTTTGGTTAAGTCCTGCAACGAGCGCAACCCTTGTTGCTAGTTA.
DHE.(dll).seq  CTCGTGCCGTGAGGTGTTTGGTTAAGTCCTGCAACGAGCGCAACCCTTGTTGCTAGTTA.

1129                                                      1187
E.coli.16S seq CAGCGGTCCGGCCGGGAACTCAAAGGAGACTGCCAGTGATAAACTGG.AGGAAGGTGGGG
DHE.(cornell)  .AATTTTCTAGC.GAG.ACT..AGCGAGACTGCCC.CGCGAAACGGGAGGAAGGTGGGG
DHE.(Stf).seq  .AATTTTCTAGC.GAG............ACTGCCC.CGCGAAACGGGAGGAAGGTGGGG
DHE.(pl ).seq  .AATTTTCTAGC.GAG............ACTGCCC.CGCGAAACGGGAGGAAGGTGGGG
DHE.(dab).seq  .AATTTTCTAGC.GAG............ACTGCCC.CGCGAAACGGGAGGAAGGTGGGG
DHE.(pin).seq  .AATTTTCTAGC.GAG............ACTGCCC.CGCGAAACGGGAGGAAGGTGGGG
DHE.(dll).seq  .AATTTTCTAGC.GAG............ACTGCCC.CGCGAAACGGGAGGAAGGTGGGG 1188                                                      1247
E.coli.16S seq ATGACGTCAAGTCATCATGGCCCTTACGACCAGGGCTACACACGTGCTACAATGGCGCAT
DHE.(cornell)  ATGACGTCAAGTCAGCATGGCCTTTATATCTTGGGCTACACACACGCTACAATGGACAGA
DHE.(Stf).seq  ATGACGTCAAGTCAGCATGGCCTTTATATCTTGGGCTACACACACGCTACAATGGACAGA
DHE.(pl ).seq  ATGACGTCAAGTCAGCATGGCCTTTATATCTTGGGCTACACACACGCTACAATGGACAGA
DHE.(dab).seq  ATGACGTCAAGTCAGCATGGCCTTTATATCTTGGGCTACACACACGCTACAATGGACAGA
DHE.(pin).seq  ATGACGTCAAGTCAGCATGGCCTTTATATCTTGGGCTACACACACGCTACAATGGACAGA
DHE.(dll).seq  ATGACGTCAAGTCAGCATGGCCTTTATATCTTGGGCTACACACACGCTACAATGGACAGA 1248                                                      1307
E.coli.16S seq ACAAAGAGAAGCGACCTCGCGAGAGCAAGCGGACCTCATAAAGTGCGTCGTAGTCCGGAT
DHE.(cornell)  ACAATAGGTTGCAACAGTGTGAACTGGAGCTAATCCC.CAAAGCTGTCCTCAGTTCGGAT
DHE.(Stf).seq  ACAATAGGTTGCAACAGTGTGAACTGGAGCTAATCCT.CAAAGCTGTCCTCAGTTCGGAT
DHE.(pl ).seq  ACAATAGGTTGCAACAGTGTGAACTGGAGCTAATCCC.CAAAGCTGTCCTCAGTTCGGAT
DHE.(dab).seq  ACAATAGGTTGCAACAGTGTGAACTGGAGCTAATCCC.CAAAGCTGTCCTCAGTTCGGAT
DHE.(pin).seq  ACAATAGGTTGCAACAGTGTGAACTGGAGCTAATCCC.CAAAGCTGTCCTCAGTTCGGAT
DHE.(dll).seq  ACAATAGGTTGCAACAGTGTGAACTGGAGCTAATCCT.CAAAGCTGTCCTCAGTTCGGAT 1308                                                      1367
E.coli.16S seq TGGAGTCTGCAACTCGACTCCATGAAGTCGGAATCGCTAGTAATCGTGGATCAGAATGCC
DHE.(cornell)  TGCAGGCTGAAACCCGCCTGCATGAAGTTGGAGTTGCTAGTAACCGCATATCAGCAAGGT
DHE.(Stf).seq  TGCAGGCTGAAACCCGCCTGCATGAAGTTGGAGTTGCTAGTAACCGCATATCAGCAAGGT
DHE.(pl ).seq  TGCAGGCTGAAACCCGCCTGCATGAAGTTGGAGTTGCTAGTAACCGCATATCAGCAAGGT
DHE.(dab).seq  TGCAGGCTGAAACCCGCCTGCATGAAGTTGGAGTTGCTAGTAACCGCATATCAGCATGGT
DHE.(pin).seq  TGCAGGCTGAAACCCGCCTGCATGAAGTTGGAGTTGCTAGTAACCGCATATCAGCATGGT
DHE.(dll).seq  TGCAGGCTGAAACCCGCCTGCATGAAGTTGGAGTTGCTAGTAACCGCATATCAGCAAGGT 1368                                                      1437
E.coli.16S seq ACGGTGAATACGTTCCCGGGCCTTGTACACACCGCCCGTCACACCATGGGAGTGGGTTGC
DHE.(cornell)  GCGGTGAATACGTTCTCGGGCCTTGTACACACCGCCCGTCACGTCATGANAGCCGGTAAC
DHE.(Stf).seq  GCGGTGAATACGTTCTCGGGCCTTGTACACACCGCCCGTCACGTCATGAAAGCCGGTAAC
DHE.(pl ).seq  GCGGTGAATACGTTCTCGGGCCTTGTACACACCGCCCGTCACGTCATGAAAGCCGGTAAC
DHE.(dab).seq  GCGGTGAATACGTTCTCGGGCCTTGTACACACCGCCCGTCACGTCATGAAAGCCGGTAAC
DHE.(pin).seq  GCGGTGAATACGTTCTCGGGCCTTGTACACACCGCCCGTCACGTCATGAAAGCCGGTAAC
DHE.(dll).seq  GCGGTGAATACGTTCTCGGGCCTTGTACACACCGCCCGTCACGTCATGAAAGCCGGTAAC 1438                                                      1487
E.coli.16S seq AAAAGAAGTAGGTAGCTTAACCTTCGGGAGGGCGCTTACCACTTTGTGATTCATGACTGG
DHE.(cornell)  ACTTGAAGTCGATGTGCCAACCGCAAGGAGGCAGTCGCCGAGGGTGGGACTGGTAATTGG
DHE.(Stf).seq  ACTTGAAGTCGATGTGCCAACC......................................
DHE.(pl ).seq  ACTTGAAGTCGATGTGCCAACC......................................
DHE.(dab).seq  ACTTGAAGTCGATGTGCCAACC......................................
```

```
DHE.(pin).seq   ACTTGAAGTCGATGTGCCAACC.............................
DHE.(dll).seq   ACTTGAAGTCGATGTGCCAACC.............................

1488                                              1542
E.coli.16S seq  GGTGAAGTCGTAACAAGGTAACCGTAGGGGAACCTGCGGTTGGATCACCTCCTTA  (SEQ ID NO:3)
DHE.(cornell)   GACGAAGTCGTAACAAGGTA...................................  (SEQ ID NO:7)
DHE.(Stf).seq   .......................................................  (SEQ ID NO:3)
DHE.(pl ).seq   .......................................................  (SEQ ID NO:2)
DHE.(dab).seq   .......................................................  (SEQ ID NO:4)
DHE.(pin).seq   .......................................................  (SEQ ID NO:5)
DHE.(dll).seq   .......................................................  (SEQ ID NO:6)
```

Figure 5

A. 16S rDNA Variable Sequence Region 2

```
Consensus              140  TGTGRTGGGCYGACATAWGTYGGTTCAYTAAAGCCGYAAGGYGCTTGGTGA  190  (SEQ ID NO:96)
Strain 195/DHC-plk/DCEH2  140  TGTGATGGGCTGACATAAGTCGGTTCATTAAAGCCGCAAGGTGCTTGGTGA  190  (SEQ ID NO:97)
                            |||||=|||||||||||=|||||||||=|||||||||=||||||||||||
DHC-vic/DHC-dII        140  TGTGGTGGGCCGACATAAGTTGGTTCACTAAAGCCGTAAGGTGCTTGGTGA  190  (SEQ ID NO:98)
                            ||||||||||||||||||||||||||||||||||||=|||||||||||||
DHC pin/CBDB1/FL2      140  TGTGGTGGGCCGACATATGTTGGTTCACTAAAGCCGTAAGGGCTTGGTGA   190  (SEQ ID NO:99)
```

B. 16S rDNA Variable Sequence Region 6

```
Consensus              940  TGWAGTAGTGAACYGAAACGACCGACCTGTTAAGTCAGGARYTTGCACA   990  (SEQ ID NO:100)
Strain 195/DHC-plk/DCEH2  940  TGAAGTAGTGAACCGAAACGAAAGGAAACGACCTGTTAAGTCAGGAGTTTGCACA  990  (SEQ ID NO:101)
                             ||||||||||||||||||=||||||||||||||||||||||||||||||
DHC-vic/DHC-dII        941  TGAAGTAGTGAACCGAAACGAAAGGGAAACGACCTGTTAAGTCAGGAGTTTGCACA  991  (SEQ ID NO:102)
                             |=|||||||||||||||||||||||||||||||||||||||||||==|||||
DHC pin/CBDB1/FL2      940  TGTAGTAGTGAACTGAAACGAAAGGGGAACGACCTGTTAAGTCAGGAACTTGCACA  990  (SEQ ID NO:103)
```

US 6,894,156 B2

NUCLEIC ACID FRAGMENTS FOR THE IDENTIFICATION OF DECHLORINATING BACTERIA

FIELD OF THE INVENTION

The invention relates to the field of molecular biology and microbiology. More specifically, 16S rRNA regions have been identified and isolated from *Dehalococcoides ethenogenes* and other bacteria that are capable of reductive dechlorination that enable the identification of dechlorinating bacterial organisms. Probes and primers corresponding to the unique regions have been constructed to enable the rapid identification of the dechlorinators.

BACKGROUND

Groundwater pollution by halogenated, and particularly chlorinated, solvents is a worldwide problem associated primarily with industrial sites where mishandling or improper disposal has brought these solvents in contact with the soil. The most common and problematic compounds are the chlorinated ethylenes (ethenes) such as tetra- tri- or dichloroethylene. Carbon tetrachloride, chloroform and methylene chloride are also pervasive pollutants. The reasons for concern are basically threefold. First, most of these solvents are sparingly soluble in water and have the tendency to stick to soil particles. This results in tenacious underground plumes of solvent that cannot readily be removed by standard pump and treat technology (Biswas, N., et al., *Water Environ. Res.* 64, 170, 10, 1 (1992); Hutter, G. M., et al., *Water Environ. Res.* 64, 69, (1992)). Second, the toxicology of many chlorinated solvents suggests that these compounds may be carcinogenic and damaging to specific organs such as the liver and kidneys (Price, P. S., Memo of the U.S. Environmental Protection Agency, Office of Water, Washington, D.C. (1985); Vogel, T. M., *Environ. Sci. Technol.*, 21, 722, (1987)). Finally, under conditions found in many aquifers and subsurface environments, chlorinated ethylenes and methanes are very slow to be degraded biologically. The result of these factors is that chlorinated solvents are long-lived and potentially hazardous groundwater pollutants.

Currently, there are two approaches to in situ removal of organohalogen pollutants. The first approach is the standard "pump and treat" method where groundwater is pumped to the surface for physical stripping of the contaminant from the water. For chlorinated solvents this is more of a containment method than a remediation technology, although given sufficient time (typically decades to centuries) this method may capture most of the pollutant. The other approach is biological in nature and utilizes microorganisms for the enzymatic transformation of the halogenated organics. The biological approach may utilize microorganisms indigenous to a particular site, such that the remediation process consists primarily of making additions to the contaminated site that enhance the growth of the desired microorganism. Alternatively, nonindigenous microorganisms may be introduced to a contaminated site with the necessary amendments needed for growth.

A number of organisms are known to dechlorinate persistent chlorinated pollutants. For example, *Dehalobacter restrictus, Dehalospirillum multivorans, Desulfitobacterium dehalogens,* and *Desulfuromonas chloroethenica* have been shown to partially dechlorinate chlorinated ethenes (Kochian et al., *Plant Mol. Biol.* 46:237 (1995); Delhaize et al., *Plant Physiol.* 107:315 (1995); Gerritse et al. *Arch. Microbiol.* 165:132 (1996); Damborsky, *Folia Microbiol. (Praha)* 44:247 (1999)). Similarly, *Dehalococcoides ethenogenes* has been shown to effect the complete dechlorination of tetrachloroethene and trichloroethene to ethene (Freedman et al., *Appl. Environ. Microbiol.* 55:2144 (1989)) and Maymó-Gatell et al. (*Science,* 176:1568 (1997)) have isolated a *D. ethenogenes* organism that is capable of respiratory reductive dechlorination of tetrachloroethene directly to ethene with hydrogen as an electron donor. Analysis of the 16S rRNA of the Maymó-Gatell organism revealed a unique profile that may be used to identify organisms of similar reductive capabilities.

The first step in utilizing the dechlorinating properties of the above identified organism is rapid and accurate identification. One method of identification involves the use of DNA probes (see for example in WO 89/06704, U.S. Pat. Nos. 4,851,330, and 5,574,145). Many such probes can be derived, based on the observation (see Woese, *Scientific American* 244(6): 98–122 (1981) for review) that parts of the 16S and 23s ribosomal RNA (rRNA) sequences vary in different species. This information was used initially for phylogenetic analyses but it has more recently been used for DNA probe-based methods for the identification of organisms. The utility of such a method is based on the conservation of nucleic acid sequence within the rRNA sequences.

Each of the cells of all life forms, except viruses, contains ribosomes and therefore ribosomal RNA. A ribosome contains three separate single strand RNA molecules, namely, a large molecule, a medium sized molecule, and a small molecule. The two larger rRNA molecules vary in size in different organisms. Ribosomal RNA is a direct gene product and is coded for by the rRNA gene. This DNA sequence is used as a template to synthesize rRNA molecules. A separate gene exists for each of the ribosomal RNA subunits. Multiple rRNA genes exist in most organisms, many higher organisms containing both nuclear and mitochondrial rRNA genes. Numerous ribosomes are present in all cells of all life forms. About 85–90 percent of the total RNA in a typical cell is rRNA. A bacterium such as *E. coli* contains about $10^4$ ribosomes per cell. Much of the sequences in rRNA are highly conserved across broad evolutionary boundaries, however, certain regions are highly variable and may be used to make fine distinctions between species, sub-species and strains (U.S. Pat. No. 5,567,587).

The problem to be overcome therefore is to identify a unique 16S rDNA sequence in a bacteria capable of dechlorination of persistent chlorinated compounds for the identification and ultimate enhancement of that bacteria to remediate a contaminated site. Applicants have solved the stated problem by providing a set of nucleic acid sequences that are unique to various species of *Dehalococcoides ethenogenes* and other species of dehalogenating bacteria.

SUMMARY OF THE INVENTION

The present invention provides an isolated 16S rDNA sequence indicative of a dechlorinating bacterial organism selected from the group consisting of: (a) SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 30 SEQ ID NO: 34, SEQ ID NO 94 and SEQ ID NO:95; (b) an isolated nucleic acid molecule that hybridizes with (a) under the following hybridization conditions: 0.1×SSC, 0.1% SDS at 65° C.; and (c) an isolated nucleic acid molecule that is completely complementary to (a) or (b).

The invention further provides primers and probes useful for the identification of new dechlorinating bacteria selected from the group consisting of: SEQ ID NOs: 9–29, SEQ ID NOs: 35–75, and SEQ ID NOs: 77–93, and any sequences that hybridize under conditions of 0.1×SSC, 0.1% SDS at 65° C. to those primers and probes.

The invention additionally provides an isolated bacterial organism comprising any one of the sequences of the instant invention as set forth in SEQ ID NO: 1, SEQ ID NO: 2, SEQ ID NO: 3, SEQ ID NO: 4, SEQ ID NO: 5, SEQ ID NO: 6 SEQ ID NO: 8, SEQ ID NOs: 9–29, SEQ ID NO: 30, SEQ ID NO: 34, SEQ ID NOs: 35–75, and SEQ ID NOs: 77–93 wherein said organism has the ability to dechlorinate chlorinated compounds.

The invention further provides a method for identifying a dechlorinating bacterial organism comprising: (i) extracting genomic DNA from a cell suspected of being able to dechlorinate chlorinated compounds; (ii) probing the extracted genomic DNA with a probe derived from any one of the sequences instant invention as set forth in SEQ ID NO: 1, SEQ ID NO: 2, SEQ ID NO: 3, SEQ ID NO: 4, SEQ ID NO: 5, SEQ ID NO: 6 SEQ ID NO: 8, SEQ ID NOs: 9–29, SEQ ID NO: 30, SEQ ID NO: 34, SEQ ID NOs: 35–75, and SEQ ID NOs: 77–93 under suitable hybridization conditions, wherein the identification of a hybridizable nucleic acid fragment confirms the presence of a bacteria capable of dechlorinating chlorinated compounds.

Similarly the invention provides a method for identifying a dechlorinating bacterial organism comprising (i) extracting genomic DNA from a cell suspected of being able to dechlorinate chlorinated compounds; and (ii) amplifying the extracted genomic DNA with an oligonucleotide primer corresponding to a portion of any one of the sequences instant invention as set forth in SEQ ID NO: 1, SEQ ID NO: 2, SEQ ID NO: 3, SEQ ID NO: 4, SEQ ID NO: 5, SEQ ID NO: 6 SEQ ID NO: 8, SEQ ID NOs: 9–29, SEQ ID NO: 30, SEQ ID NO: 34, SEQ ID NOs:35–75, and SEQ ID NOs: 77–93 such that amplification products are generated wherein the presence of amplification products confirms the presence of a dechlorinating bacterial organism.

The invention additionally provides a method for identifying a dechlorinating bacterial organism comprising:
(i) extracting total cellular RNA from a cell suspected of being able to dechlorinate chlorinated compounds;
(ii) synthesizing complementary DNA strands to the extracted rRNA using a reverse transcriptase and at least one oligonucleotide primer corresponding to a portion of the isolated 16S rDNA sequences of the present invention;
(iii) amplifying the newly generated complementary DNA strands to the extracted rRNA using at least one oligonucleotide primer corresponding to a portion of the isolated 16S rDNA sequences of the present invention such that amplification products are generated;
wherein the presence of amplification products confirms the identification of a dechlorinating bacterial organism.

The invention additionally provides a method for the dechlorination of chlorinated compounds comprising contacting a chlorinated compound with an isolated bacterial organism comprising any one of the DNA fragments as set forth in SEQ ID NO: 1, SEQ ID NO: 2, SEQ ID NO: 3, SEQ ID NO: 4, SEQ ID NO: 5, SEQ ID NO: 6 SEQ ID NO: 8, SEQ ID NOs: 9–29, SEQ ID NO: 30, SEQ ID NO: 34, SEQ ID NO:94, SEQ ID NO:95, SEQ ID NOs: 35–75, and SEQ ID NOs: 77–93 under conditions suitable for dechlorination to occur.

In a preferred embodiment the invention provides a method for the identification of a dechlorinating bacteria selected from the group consisting of *Dehalobacter restrictus, Dehalospirillus multivorans, Desulfitobacterium dehalogenans, Desulfuromonas chloroethnica,* and *Dehalococcoides* Family A Group based on the use of signature sequences selected from the group consisting of SEQ NO:'s 79–93.

Additionally the invention provides a diagnostic nucleic acid gene fusion useful in Denaturing Gradient Gel Electrophoresis having the general structure: DS-GC, wherein:
(i) SS is a signature sequence selected from the group consisting of SEQ ID NOs: 9–29, SEQ ID NO: 30, SEQ ID NO: 34, SEQ ID NO:94, SEQ ID NO:95, SEQ ID NOs: 35–75, and SEQ ID NOs: 77–93; and
(ii) GC is a GC clamp sequence having the sequence as set forth in SEQ ID NO:76.

In another embodiment the invention provides a method for separating sub-families of dechlorinating bacterial organisms comprising:
(i) extracting total cellular rRNA from a cell suspected of being able to dechlorinate chlorinated compounds;
(ii) synthesizing complementary DNA strands to the extracted rRNA using a reverse transcriptase and at least one oligonucleotide primer corresponding to a portion of the diagnostic gene fusion of the invention such that amplification products are generated;
(iii) amplifying the newly generated complementary DNA strands to the extracted rRNA of step (ii) using at least one oligonucleotide primer corresponding to a portion of the diagnostic gene fusion of the invention such that amplification products are generated; and
(iv) separating the amplification products by Denaturing Gradient Gel Electrophoresis.

BRIEF DESCRIPTION OF THE DRAWINGS AND SEQUENCE LISTING

FIG. 1 is an alignment of the 16S rDNA sequence profile from *Dehalococcoides ethenogenes* DHE-195 as disclosed in Maymó-Gatell et al., *Science,* 176:1568 (1997), as compared with profiles generated for organisms isolated from a number of wastewater treatment sites.

FIG. 2 is a comparison of the instant dechlorinating 16S rDNA profiles with a 16S rDNA profile from *E. coli.*

Figure 3:
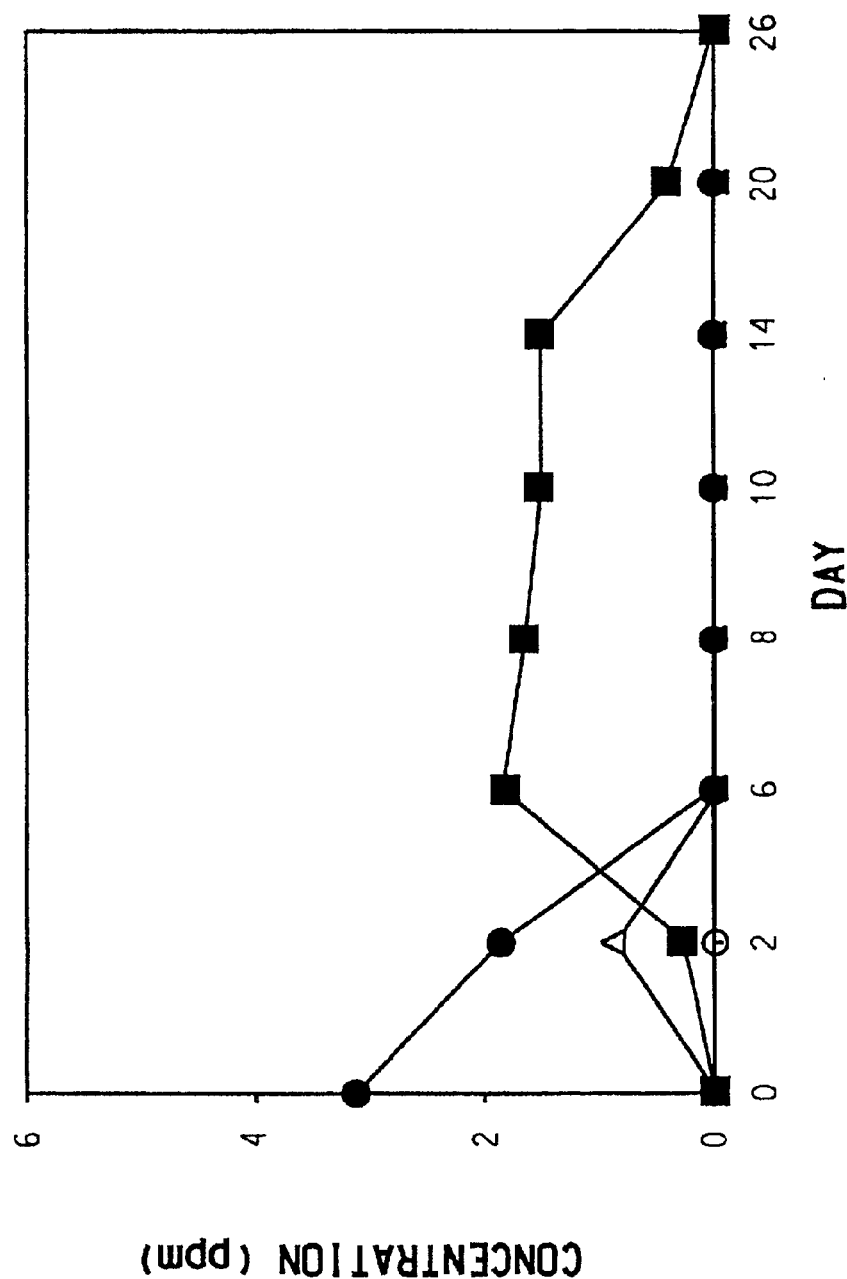
FIG. 3 is a graph illustrating the ability of a soil microcosm or culture developed from certain soils taken from a chloroethene-contaminated site to dechlorinate trichloroethylene or perchloroethylene.

FIGS. 5A and B are alignments of sequences illustrating 16s rDNA variable sequence regions 2 and 6, respectively.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO: 1 is a unique region of the *Dehalococcoides ethenogenes* 16S rDNA profile that is linked to dechlorinating activity.

SEQ ID NO:2 is the 16S-rDNA profile of Dehalococcoides ethenogenes DHE-PL, isolated from soil surrounding in industrial site.

SEQ ID NO:3 is the 16S rDNA profile of Dehalococcoides ethenogenes DHE-V/SFD, isolated from soil surrounding in industrial site.

SEQ ID NO:4 is the 16S-rDNA profile of Dehalococcoides ethenogenes DHE-DAB, isolated from soil surrounding in industrial site.

SEQ ID NO:5 is the 16S-rDNA profile of Dehalococcoides ethenogenes DHE-PIN, isolated from soil surrounding in industrial site.

SEQ ID NO:6 is the 16S-rDNA profile of Dehalococcoides ethenogenes DHE-DLL, isolated from soil surrounding in industrial site.

SEQ ID NO:7 is the 16S rDNA profile of Dehalococcoides ethenogenes DHE-195 as reported in Maymó-Gatell et al. (*Science,* 176:1568 (1997)), GenBank AF004928.

SEQ ID NO:8 is the consensus sequence derived from DHE-PL, DHE-V/SFD, DHE-DAB, DHE-PIN, and DHE-DLL at bases E180–E226.

SEQ ID NOs: 9–29 are primers derived from the 16S-rDNA profile, useful in the identification of dechlorinating bacteria.

SEQ ID NO:30 is the consensus sequence derived from DHE-PL, DHE-V/SFD, DHE-DAB, DHE-PIN, and DHE-DLL at bases E1001–E1047.

SEQ ID NO:31 is the base sequence in the region of the consensus 16S-rDNA profile from where the diagnostic sequence is derived.

SEQ ID NO:32 is the base sequence in the region of the DHE-195 16S-rDNA profile from where the diagnostic sequence is derived.

SEQ ID NO:33 is the *E. coli* reference 16S-rDNA sequence.

SEQ ID NO:34 is a unique region of the *Dehalococcoides ethenogenes* 16S rDNA profile that is linked to dechlorinating activity.

SEQ ID NOs: 35–60 are probes designed from unique regions of the *Dehalococcoides ethenogenes* 16S rDNA profile that are linked to dechlorinating activity.

SEQ ID NOs: 61–75 are primers derived from a 16S-rDNA profile, useful in the identification of dechlorinating bacteria.

SEQ ID NO: 76 is a GC clamp sequence, useful in DGGE.

SEQ ID NOs: 77 and 78 are primers containing a GC clamp sequence, for separation of DHE sequence sub-families by DGGE.

SEQ ID NOs: 79–93 are primers derived from the 16S-rDNA profile, useful in the identification of dechlororespirating bacteria.

SEQ ID NO: 94 describes the *Dehalococcoides* related Family A 16S DHFA sequence.

SEQ ID NO: 95 describes the *Dehalococcoides* related Family A 16S FAOK sequence.

SEQ ID NO:96 is the consensus sequence derived from DHE-195, DHE-V/SFD, and DHE-PIN at bases E180–E231 (DHE 140–DHE190), representing variable sequence region 2.

SEQ ID NO:97 is the 16S-rDNA profile of DHE-195 at bases E180–E231 (DHE 140–DHE190), representing variable sequence region 2.

SEQ ID NO:98 is the 16S-rDNA profile of DHE-V/SFD at E180–E231 (DHE 140–DHE190), representing variable sequence region 2.

SEQ ID NO:99 is the 16S-rDNA profile of DHE-PIN at bases E180–E231 (DHE 140–DHE190), representing variable sequence region 2.

SEQ ID NO:100 is the consensus sequence derived from DHE-195, DHE-V/SFD, and DHE-PIN at bases E1001–E1046 (DHE940–DHE990), representing variable sequence region 6.

SEQ ID NO:101 is the 16S-rDNA profile of DHE-195 at bases E1001–E1046 (DHE940–DHE990), representing variable sequence region 6.

SEQ ID NO:102 is the 16S-rDNA profile of DHE-V/SFD at bases E1001–E1046 (DHE940–DHE990), representing variable sequence region 6.

SEQ ID NO:103 is the 16S-rDNA profile of DHE-PIN at bases E1001–E1046 (DHE940–DHE990), representing variable sequence region 6.

DETAILED DESCRIPTION OF THE INVENTION

The present invention provides unique 16S rDNA sequence profiles derived from *Dehalococcoides ethenogenes* (DHE). *D. ethenogenes* is known for its ability to degrade persistent chlorinated pollutants. The instant sequence profiles may be used to identify and sub-type bacteria with similar metabolic pathways. One sequence (SEQ ID NO:1), beginning at base E1146, has been identified in all DHE sequences isolated from contaminated soils and is strongly linked to the ability of these organisms to degrade chlorinated organics. Similarly, a longer sequence has been identified (SEQ ID NO:34), beginning at base E1112 and extending to base E1175, which contains SEQ ID NO:1, but is itself unique and is diagnostic for the ability of these organisms to degrade chlorinated organics. Additionally, a stretch of nucleic acids ranging between E180 and E226, corresponding to SEQ ID NO:8 may be used to identify dechlorinators as well as for genetic sub-typing of species.

Additionally, the present invention provides unique probe and primer sequences that may be used to identify other dechlorinating bacteria, e.g., *Dehalobacter restrictus, Dehalospirillum multivorans, Desulfitobacterium dehalogenans* and *Desulfuromonas chloroethnica.* These organisms are responsible for a partial dechlorination reaction, whereby TCE is transformed to 1,2 cis-dichloroethene (cDCE). In addition, unique diagnostic probe and primer seqeuences are provided that are useful for identification of another group of organisms, the *Dehalococcoides* Family A Group. Preliminary evidence links this group of organisms to the dechlorination of cDCE to ethene.

In this disclosure, a number of terms and abbreviations are used. The following definitions are provided.

Trichloroethylene will be abbreviated "TCE".

Perchloroethylene will be abbreviated "PCE".

1,2 cis-dichloroethene will be abbreviated "cDCE".

Vinyl chloride will be abbreviated "VC".

The terms "ethylene" and "ethene" are the same compound and will be used interchangeably.

"Polymerase chain reaction" is abbreviated PCR.

"Reverse transcription followed by polymerase chain reaction" is abbreviated RT-PCR.

The term *"Dehalococcoides ethenogenes"* will be abbreviated "DHE".

"Dehalorespiration" is a process whereby an organism uses a halo-organic compound as an electron acceptor for energy and growth. More specifically, hydrogen is used as the electron donor, the halo-organic compound is the electron acceptor, and hydrogen halide (i.e., HBr, HCl or HF) is produced. Several anaerobic bacteria are able to reductively dechlorinate chlorinated hydrocarbons and to gain energy from this dehalorespiration process.

A subset of dehalorespiration is known as reductive dechlorination. "Reductive dechlorination" is a term that refers to the process in which a chloro-organic compound as terminal electron acceptor and a chloride atom is removed from a chloro-organic compound.

The term "dechlorinating bacteria" refers to any bacterial species or organism that has the ability to remove at least one chloride atom from a chlorinated organic compound. Dechlorinating bacteria may have the ability to grow on chlorinated organics as a sole electron acceptor, or may prefer degradation using an alternate energy source. Examples of dechlorinating bacteria described in the present application are: *Dehalococcoides ethenogenes, Dehalococcoides ethenogenes*-like organisms, *Dehalobacter restrictus, Dehalospirillum multivorans, Desulfitobacterium dehalogenans, Desulfuromonas chloroethnica,* and *Dehalococcoides* Family A Group.

The term "*Dehalococcoides ethenogenes*-like organisms" are those bacteria that have unique 16S rDNA sequences that have sequence identity to *Dehalococcoides ethenogenes* and are associated with the dechlorination of chlorinated-organic compounds, such as chloroethenes, chlorobenzenes dichlorethane, and 1,2 dichloropropane.

The term "chlorinated compounds" will mean any straight chain or ring containing organic compound that contains at least one chlorine atom.

The term "DHE-195" will refer to the strain of *Dehalococcoides ethenogenes* isolated and characterized by Maymó-Gatell et al. (*Science,* 176:1568 (1997)).

The term "16S rDNA" will refer to the DNA encoding ribosomal RNA. This is the nucleic acid component of the small (30S) ribosomal subunit found within bacterial cells.

The term "16S rDNA profile" will refer to the specific DNA sequence of the rDNA gene in any particular organism. For the purposes of the present invention, the 16S rDNA profiles for DHE-195, DHE-PL, DHE-V/SFD, DHE-DAB, DHE-DLL and DHE-PIN are illustrated in FIGS. 1 and 2.

The terms "DHE-PL", "DHE-V/SFD", "DHE-DAB", "DHE-DLL", and "DHE-PIN" will refer to strains of *Dehalococcoides* sp. containing the instant dechlorinating 16S rDNA profile.

The terms "DHE-DHFA", and "DHE-FAOK" will refer to *Dehalococcoides* related Family A Group organisms.

The term "signature sequence" or "signature sequence region" will refer to those short sequences in the 16S gene or rRNA molecule which are unique to a certain group or groups of organisms. These sequences can be used to define domains, group, subdivisions, genera or species of an organism.

The term "consensus sequence" as used herein, as it relates to the alignment of a given set of sequences, will be defined as the sequence of the set of bases where a designated base is the one that occurs most often at each position in the 16S sequence.

The term "reference sequence" as used herein, as it relates to the alignment of a given set of sequences, will be defined as the particular 16S sequence to which the bases at each position of an alignment of 16S sequences are compared. The reference sequence used herein was an *E. coli* 16S rDNA sequence. Bases identified in the reference sequence that correlate to corresponding bases in a 16S rDNA profiled are assigned an "E number". Thus, the base labeled E-27 on the reference sequence corresponds to base 1 of the 16S rDNA profile of DHE-195 and E-107 corresponds to base 66 of DHE-195. The complete correlation is given in Table 2.

The term "dechlorinating 16S rDNA profile" will refer to a 16S-rDNA profile containing the diagnostic sequence as set forth in SEQ ID NO:1.

The term "diagnostic sequence" will refer to the sequences as set forth in SEQ ID NO:1 or SEQ ID NO:34 which are indicative of dechlorinating activity.

The letters "A", "G", "T", "C" when referred to in the context of nucleic acids will mean the purine bases adenine ($C_5H_5N_5$) and guanine ($C_5H_5N_5O$) and the pyrimidine bases thymine ($C_5H_6N_2O_2$) and cytosine ($C_4H_5N_3O$), respectively.

"Gene" refers to a nucleic acid fragment that expresses a specific protein or RNA (e.g., rRNA), and also includes regulatory sequences preceding (5' non-coding sequences) and following (3' non-coding sequences) the coding sequence.

The term "nucleic acid fragment" will refer to a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

The term "oligonucleotide" refers to primers, probes, oligomer fragments to be detected, labeled-replication blocking probes, and oligomer controls, and shall be generic to polydeoxyribonucleotides (containing 2-deoxy-D-ribose), to polyribonucleotides (containing D-ribose) and to any polynucleotide which is an N-glycoside of a purine or pyrimidine base (nucleotide), or modified purine or pyrimidine base. Also included in the definition of "oligonucleotide" are nucleic acid analogs (e.g., peptide nucleic acids) and those that have been structurally modified (e.g., phosphorothioate linkages). There is no intended distinction between the length of a "nucleic acid", "polynucleotide" or an "oligonucleotide".

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase.

The term "probe" refers to an oligonucleotide (synthetic or occurring naturally), that is significantly complementary to a "fragment" and forms a duplexed structure by hybridization with at least one strand of the fragment.

The term "replication inhibitor moiety" refers to any atom, molecule or chemical group that is attached to the 3' terminal hydroxyl group of an oligonucleotide that will block the initiation of chain extension for replication of a nucleic acid strand. Examples are (but not limited to) 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units.

The term "non-participatory" will refer to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

The term "complementary" is used to describe the relationship between nucleotide bases that are hybridizable to one another. For example, with respect to DNA, adenosine is complementary to thymine and cytosine is complementary to guanine.

A nucleic acid molecule is "hybridizable" to another nucleic acid molecule, such as a cDNA, genomic DNA, or RNA, when a single-stranded form of the nucleic acid molecule can anneal to another single-stranded nucleic acid molecule under the appropriate conditions of temperature and solution ionic strength to form a double-stranded nucleic acid. Hybridization and washing conditions are well known and exemplified in Sambrook, J., Fritsch, E. F. and Maniatis, T. *Molecular Cloning: A Laboratory Manual,* Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51, hereby incorporated by reference). For hybridizations with shorter nucleic acids, i.e., oligonucleotides, the position of mismatches becomes more important, and the length of the oligonucleotide determines its specificity (see Sambrook et al., supra, 11.7–11.8, hereby incorporated by reference). In one embodiment the length for a hybridizable nucleic acid is at least about 10 nucleotides. Preferable a minimum length for a hybridizable nucleic acid is at least about 15 contiguous nucleotides; more preferably at least about 20 contiguous nucleotides; and most preferably the length is at least 30 contiguous nucleotides. Thus, where a "probe" or "primer" is "derived from" or corresponds to a "portion" of a nucleic acid fragment, the probe or primer or portion will preferably be at least about 15 contiguous nucleotides; more preferably at least about 20 contiguous nucleotides; and most preferably the length is at least 30 contiguous nucleotides of the fragment from which it is derived. Furthermore, the skilled artisan will recognize that the temperature and wash solution salt concentration may be adjusted as necessary according to factors such as length of the probe.

The term "amplification product" refers to portions of nucleic acid fragments that are produced during a primer directed amplification reaction. Typical methods of primer directed amplification include polymerase chain reaction (PCR), ligase chain reaction (LCR) or Strand displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. See, for example, Tabor et al., *Proc. Acad. Sci. U.S.A.,* 82, 1074–1078 (1985)). Additional methods of RNA replication such as replicative RNA system (Qβ-replicase) and DNA dependent RNA-polymerase promoter systems (T7 RNA polymerase) are contemplated to be within the scope of the present invention.

The term "reverse transcription followed by polymerase chain reaction", or "RT-PCR", refers to a sensitive technique for quantitative analysis of gene expression, cloning, cDNA library construction, probe synthesis, and signal amplification in in situ hybridizations. The technique consists of two parts: synthesis of cDNA from RNA by reverse transcription (RT), and amplification of a specific cDNA by polymerase chain reaction (PCR). Reverse Transcriptase is an RNA dependent DNA polymerase that catalyses the polymerization of nucleotides using template DNA, RNA or RNA:DNA hybrids. It is important to utilize a total RNA isolation technique that yields RNA lacking significant amounts of genomic DNA contamination, since the subsequent PCR cannot discriminate between cDNA targets synthesized by reverse transcription and genomic DNA contamination.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc., 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

The present invention relates to unique 16S rDNA sequences that have been isolated from bacteria very similar if not related to *Dehalococcoides ethenogenes,* which are associated with the ability of this bacterium to dechlorinate chlorinated-organic compounds. The sequences were isolated from bacteria found in soil and groundwater samples of various industrial sites that have been shown to contain bacteria that have the ability to dechlorinate chlorinated compounds. The sequences are useful for the identification of new dechlorinating bacteria, as well as for sub-typing strains of *Dehalococcoides ethenogenes*.

Dechlorinating bacteria were isolated from the aquifer soil taken from around industrial sites by means well known in the art. Samples were maintained under anaerobic conditions and cultured in a suitable medium for the growth of anaerobic soil bacteria. Such culture procedures and media are common and well known in the art and are described in *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

In order to enrich the cultured soil samples for dechlorinating bacteria, the samples were contacted with a low level of chlorinated organic compound. A number of chlorinated compounds are suitable for this purpose including, but not limited to: carbontetrachloride, tetrachloroethene, chloroform, dichloromethane, trichloroethene, dichloroethylene, vinyl chloride, and chloroaromatics, dichloropropane, and chlorinated ethane where chlorinated ethenes are preferred and TCE, PCE, cDCE and VC are most preferred. Incubation proceeded for about six months, and cultures were analyzed periodically for the disappearance of the chlorinated organic and the appearance of degradation products. Cultures demonstrating the ability to degrade chlorinated organics were selected for further analysis.

Bacteria from dechlorinating cultures were removed by standard methods and total chromosomal DNA was isolated from the microorganisms through a bead mill homogenization procedure. A fragment of the 16S rRNA gene was amplified from the genomic DNA extract by PCR using 16S rDNA primers specific for dechlorinating microbes. The 16S rRNA gene is particularly well suited for studying environmental microbial communities because: 1) there is a large database of these sequences publicly available; 2) it is ubiquitously present throughout the macrocosm of life; 3) it is species specific; and 4) its function is conserved. Thus, the 16S rRNA gene is used in this study and throughout the literature as a phylogenetic aid in identifying and relating different organisms.

The 16S rDNA PCR product was cloned and sequenced to confirm its identity (M. I. More et al. 1994. *Appl. Environ. Microbiol.*, 60: 1572–1580). Each raw 16S sequence obtained was assembled into a contig, and a consensus was manually constructed using Seqman II in DNAstar (DNAstar, Inc., Madison, Wis.). For each test sequence, a Pearson and Lipman similarity search was performed using the FASTA program in GCG (Wisconsin Package Version 9.0, Genetics Computer Group, Madison, Wis.). The nearest organism in similarity in 16S rRNA sequence to the test sequence was used as the nearest match for identification. Those 16S DNA gene sequences that were identified to be similar to the dechlorinating bacteria *Dehalococcoides ethenogenes* DHE-195 (GenBank Accession No. AF004928) were aligned with selected 16s rRNA sequences. extracted from the Ribosomal Database Project (Michigan State University). These selected 16s rRNA sequences were a representation of the major microorganism domains, Bacteria and Archeae, in the Universal Phylogenetic Tree of Life. The sequences were aligned using MegAlign in DNAstar, using the default software parameters. From this alignment probable regions for signature sequences were mapped. Then sequences from each region were tested against the Ribosomal Database (RDB) for unique sequences that could be signature sequences and utilized as PCR primers or detection probes.

Within the 16S rDNA profile defined by the comparison of the isolated dechlorinators (see FIGS. 1 and 2), four signature regions showed considerable variation from the known sequences. Those regions were defined as extending from E1146 to E1156 (SEQ ID NO:1), from E180 to E227 (SEQ ID NO:8), and from E1001 to E1047 (SEQ ID NO:30). A fourth sequence, SEQ ID NO:34, which contains SEQ ID NO:1 is also unique and may be used to definitely identify these organisms. All of the dechlorinating isolates of the present invention contained the sequence as set forth in SEQ ID NO:1 or SEQ ID NO:34 which are conspicuously absent from the sequence known in the art (Maymó-Gatell et al. (*Science*, 176:1568 (1997)). SEQ ID NO:34 extends from E1112 to E1175 and contains SEQ ID NO:1 as shown by the double unlined portion below.

```
                                              (SEQ ID NO:34)
    E1114E1118                          E1168
       |   |                              |
AACCCTTGTTGCTAGTTAAATTTTCTAGCGAGACTGCCCCGCGAAACGG
```

Although a region similar to that defined by SEQ ID NO:8 is found in the literature sequence, there are significant variations at positions E184, E190, E198, E201, E208, E217, and E222 as shown below.

```
                                              (SEQ ID NO:8)
  E184    E190     E198 E201    E208
    |      |         |   |       |
  TGTGRTGGGCY GACATAWGTY GGTTCAYTAA
                                  E217 E222
                                    |   |
                            AGCCGYAAGGYGC TTG
```

Within the context of the present invention Applicants have discovered that within the signature region defined by SEQ ID NO:8 above, the R at position E184 may be A/G, the Y at position E190 may be C/T, the W at position E198 may be A/T, and the Y's at position E201, E208, E217, and E222 may be T/C.

Similarly the region defined by SEQ ID NO:30 is also found in the literature but contains significant variations at positions E1003, E1012, E1020, E1039, and E1040 as shown below.

```
                                              (SEQ ID NO:30)
  E1003       E1012   E1020
    |           |       |
  TGWAGTAGTGAACMGAAAGGGRAACGA
                                       E1039
                                         |
                        CCTGTTAAGTCAGGARMTTGCACA
                                              |
                                           E1040
```

As with SEQ ID NO:8, Applicants have discovered that within the signature region defined by SEQ ID NO:30 above, the W at position E1003 may be A/T, at position E1012 the M may be A/C, at position E1020 the R may be A/G, at position E1039 the R may be A/G, and at position E1040 the M may be A/C.

Likewise, if the entire 16S rDNA profile is examined, it is seen that there are significant single base differences throughout the entire profile (FIGS. 1 and 2). These differences are illustrated in tabular form in Table 2. Accordingly, a 16S rDNA profile sequence having the following bases substitutions taken independently or together will be diagnostic for dechlorinating bacteria: E107=G, base E184=G, base E190=C, E 198=T, E201=T, E208=C, E217=T, E222=C, E264=C, E267=C, E291=T, E333=C, E420=C, E444=T, E631=A, E829=A, E933=T, E934=T, E980=C, E1003=T, E1012=T, E1020=G, E1039=A, E1040=C, E1087=T, E1114=C, E1284=T, E1364=T and E1427=A.

Assay Methods

The instant sequences may be used in a variety of formats for the detection of dechlorinating bacteria. The two most convenient formats will rely on methods of nucleic acid hybridization or primer directed amplification methods such as PCR.

Nucleic Acid Hybridization Methods

The basic components of a nucleic acid hybridization test include a probe, a sample suspected of containing a dechlorinating bacteria, and a specific hybridization method. As noted above, probes of the present invention are single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base. A probe may be composed of either RNA or DNA. The form of the nucleic acid probe may be a marked single stranded molecule of just one polarity or a marked single stranded molecule having both polarities present. The form of the probe, like its length, will be determined by the type of hybridization test to be done.

The sample may or may not contain the organism of interest. The sample may take a variety of forms, including liquid such as water, or solid such as dust or soil. The sample nucleic acid must be made available to contact the probe before any hybridization of probe and target molecule can occur. Thus the organism's RNA must be free from the cell and placed under the proper conditions before hybridization can occur. Methods of in solution hybridization necessitate the purification of the RNA in order to be able to obtain hybridization of the sample rRNA with the probe. This has meant that utilization of the in solution method for detection of target sequences in a sample requires that the nucleic acids of the sample must first be purified to eliminate protein, lipids, and other cell components, and then contacted with the probe under hybridization conditions. Methods for the purification of the sample nucleic acid are common and well known in the art (Maniatis, supra).

Similarly, hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

In one embodiment, hybridization assays may be conducted directly on bacterial lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to RNA at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Alternatively, one can purify the rRNA prior to probe hybridization. A variety of methods are known to one of skill in the art (e.g., phenol-chloroform extraction, IsoQuick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al. (1991) in *PCR Methods and Applications,* Cold Spring Harbor Laboratory Press, pp. 25–33) or reverse transcriptase PCR (Kawasaki (1990) in *PCR Protocols: A Guide to Methods and Applications,* M. A. Innis et al., eds., pp. 21–27). One can obtain amplified rRNA by using in vitro RNA amplification techniques as described in Fahy et al., supra; Kawasaki, supra. The exact procedure used is not crucial, provided that it does not amplify significant amounts of DNA, which would tend to obscure results.

Once the pre-rRNA is released from the cells, it can be detected by any of a variety of methods. The method of rRNA detection is not crucial to the invention. However, the most useful embodiments have at least some characteristics of speed, convenience, sensitivity, and specificity. Direct DNA probe analysis is suitable, as is an in vitro RNA amplification method, such as 3SR, that employs labeled primers.

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt/vol glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the rRNA sequence. Preferred are those probes that hybridize to regions of the rRNA that have minimal secondary and tertiary interactions. The advantage of such probes is that the hybridization can be carried out without the additional step of heat denaturing the sample nucleic acid. For example, the hybridization can be carried out at room temperature. Probes particularly useful in the present invention are those listed in Table 1 (SEQ ID NOs:35–60), Table 3 (SEQ ID NOs: 61–75) and Table 4 (SEQ ID NOs: 79–93), and SEQ ID NOs: 77, 78, 94–103.

The sandwich assay may be encompassed in an assay kit. This kit would include a first component for the collection of samples from soil or groundwater such as vials for containment, and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed or to which is conjugated unlabeled nucleic acid probe(s) that is (are) complementary to a part of the precursor rRNA of the species of bacteria being tested. In the case of multiple target analysis more than one capture probe, each specific for its own rRNA, will be applied to different discrete regions of the dipstick. A fourth component would contain labeled probe that is complementary to a second and different region of the same rRNA strand to which the immobilized, unlabeled nucleic acid probe of the third component is hybridized.

In another embodiment, the instant 16S rDNA sequence may be used as a 3' blocked detection probe in either a homogeneous or heterogeneous assay format. For example a probe generated from the instant sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from the test organism is amplified by standard primer-directed amplification protocols in the presence of an excess of the 16S rDNA 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

The probe may be several hundred bases in length where 25–65 bases are preferred. The instant probe is versatile and may be designed in several alternate forms. The 3' end of the probe is blocked from participating in a primer extension reaction by the attachment of a replication inhibiting moiety. Typical replication inhibitor moieties will include but are not limited to, dideoxynuleotides, 3-deoxynucleotide, a sequence of mismatched nucleosides or nucleotides, 3' phosphate groups and chemical agents. Within the context of the present invention cordycepin (3' deoxyadenosine) is preferred.

The replication inhibitor is covalently attached to the 3' hydroxy group of the 3' terminal nucleotide of the non-participatory probe during chemical synthesis, using standard cyanoethyl phosphoramidite chemistry. This process uses solid phase synthesis chemistry in which the 3' end is covalently attached to an insoluble support (controlled pore glass—CPG) while the newly synthesized chain grows on the 5' terminus. Within the context of the present invention, 3-deoxyribonucleotides are the preferred replication inhibitors. Cordycepin (3-deoxyadenosine) is most preferred. Since the cordycepin will be attached to the 3' terminal end of the probe, the synthesis is initiated from a cordycepin covalently attached to CPG, 5-dimethoxytrityl-N-benzoyl-3-deoxyadenosine (cordycepin), 2-succinoyl-long chain alkylamino-CPG (Glen Research, Sterling, Va.). The dimethoxytrityl group is removed and the initiation of the chain synthesis starts at the deprotected 5' hydroxyl group of the solid phase cordycepin. After the synthesis is complete, the oligonucleotide probe is cleaved off the solid support leaving a free 2' hydroxyl group on the 3'-terminally attached cordycepin. Other reagents can also be attached to the 3' terminus during the synthesis of the non-participatory probe to serve as replication inhibitors. These include, but are not limited to, other 3-deoxyribonucleotides, biotin, dinitrophenol, fluorescein, and digoxigenin, which are also derivatized on CPG supports (Glen Research, Sterling, Va.; Clonetech Laboratories, Palo Alto, Calif.).

It is understood that the probe may be RNA or DNA or a synthetic nucleic acid, however, it will contain some sequence sufficiently complementary to the nucleic acid from the *Dehalococcoides ethenogenes*-like organisms to be detected that will permit hybridization between the detection probe and the subject DNA.

PCR Assay Methods

In an alternate embodiment the present sequences may be used as primers or to generate primers that may be used in primer directed nucleic acid amplification to detect the presence of dechlorinating bacteria. A variety of primer directed nucleic acid amplification methods are known in the art including thermal cycling methods such as polymerase chain reaction (PCR) and ligase chain reaction (LCR) as well as isothermal methods and strand displacement amplification (SDA). The preferred method is PCR. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33–50; IRL Press, Herndon, Va.; and Rychlik, W. (1993) In White, B. A. (ed.), *Methods in Molecular Biology*, Vol. 15, pp 31–39, PCR Protocols: Current Methods and Applications. Humania Press, Inc., Totowa, N.J.).

If a nucleic acid target is to be exponentially amplified, then two primers are used each having regions complementary to only one of the stands in the target. After heat denaturation, the single-stranded target fragments bind to the respective primers which are present in excess. Both primers contain asymmetric restriction enzyme recognition sequences located 5' to the target binding sequences. Each primer-target complex cycles through nicking and polymerization/displacement steps in the presence of a restriction enzyme, a DNA polymerase and the three dNTP's and one dNTP[aS] as discussed above. An in depth discussion of SDA methodology is given by Walker et al., *Proc. Natl. Acad. Sci. U.S.A.*, 89, 392, (1992).

Alternatively, asymmetric amplification can be used to generate the strand complementary to the detection probe. Asymmetric PCR conditions for producing single-stranded DNA would include similar conditions for PCR as described however, the primer concentrations are changed with 50 pmol of the excess primer and 1 pmol of the limiting primer. It is contemplated that this procedure would increase the sensitivity of the method. This improvement in sensitivity would occur by increasing the number of available single strands for binding with the detection probe.

Within the context of the present invention, primers will be designed to conserved regions of the 16S rDNA profile which are associated with dechlorination. The most significant of those regions are the sequences set forth in SEQ ID NO:1, SEQ ID NO:8, SEQ ID NO:30, and SEQ ID NO:34, giving rise to primers including SEQ ID NOs: 9–29, SEQ ID NOs: 35–75, and SEQ ID NOs: 77–93.

Following amplification and prior to sequencing, the amplified nucleotide sequence may be ligated to a suitable vector followed by transformation of a suitable host organism with said vector. One thereby ensures a more readily available supply of the amplified sequence. Alternatively, following amplification, the amplified sequence or a portion thereof may be chemically synthesized for use as a nucleotide probe. In either situation the DNA sequence of the variable region is established using methods such as the dideoxy method (Sanger, F. et al. *Proc. Natl. Acad. Sci* (1977) 74, 5463–5467). The sequence obtained is used to guide the choice of the probe for the organism and the most appropriate sequence(s) is/are selected.

A variety of PCR detection methods are known in the art including standard non-denaturing gel electrophoresis (e.g., acrylamide or agarose), denaturing gradient gel electrophoresis, and temperature gradient gel electrophoresis. Standard non-denaturing gel electrophoresis is the simplest and quickest method of PCR detection, but may not be suitable for all applications.

Denaturing Gradient Gel Electrophoresis (DGGE) is a separation method that detects differences in the denaturing behavior of small DNA fragments (200–700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the ds DNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel.

As used in the present invention the diagnostic nucleic acid gene fusions were made comprising a signature sequence and a GC clamp sequence designed to alter the mobility of the fusion in the gel media. Preferred in the present invention are signature sequences having the SEQ ID NOs: as set forth in SEQ ID NOs:61–75 and SEQ ID NOs:79–95. Preferred GC clamp sequences are those having sequence similarity to the sequence as set forth in SEQ ID NO:76. Preferred diagnostic nucleic acid gene fusions of the present invention include, but are not limited to those having the sequences as set forth in SEQ ID NO:77 and SEQ ID NO:78. The skilled artisan will appreciate that placement of the GC clamp on the sequence is a matter of discretion for the investigator and that the GC clamp sequence may be attached at either 5' end of the signature sequence. A suitable method for separating sub-families of dechlorinating bacterial organisms according to the present invention may comprise steps including: (i) extracting total cellular RNA from a cell suspected of being able to dechlorinate chlorinated compounds; (ii) synthesizing complementary DNA strands to the extracted rRNA using a reverse transcriptase and at least one oligonucleotide primer corresponding to a portion of a suitable diagnostic gene fusion of the invention such that amplification products are generated; (iii) amplifying the newly generated complementary DNA strands to the extracted rRNA of step (ii) using at least one oligonucleotide primer corresponding to a portion of a suitable diagnostic gene fusion of the invention such that amplification products are generated; and (iv) separating the amplification products by Denaturing Gradient Gel Electrophoresis.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular techniques used in the Examples are well known in the art. Techniques suitable for use in the following examples may be found in Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis").

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.), DNASTAR (DNASTAR, Inc. 1228 S. Park St. Madison, Wis. 53715 USA), or the "on-line" Probe Match Program from the Ribosomal Database Project II (Michigan State University, East Lansing, Mich.). Where any sequence analysis software was used in the following examples, default values were used unless otherwise specified.

The meaning of abbreviations is as follows: "h" means hour(s), "min" means minute(s), "sec" means second(s), "d" means day(s), "mL" means milliliters, "L" means liters.

Example 1

Isolation and Characterization of Dechlorinating Soil Organisms

Aquifer core samples were obtained by split spoon sampling at depths ranging from 10 to 80 ft, depending on the depth of the particular aquifer to be tested. The cores were taken in sterile stainless steel cylinders or placed in sterile glass vials. The core samples were immediately shipped to the laboratory at ambient temperatures and under anaerobic conditions. Upon arrival the samples were stored in an anaerobic glove bag (chamber) (Coy Laboratory Products Inc., Ann Arbor, Mich.), whose atmosphere was 10% $H_2$, 5% $CO_2$ and 85% $N_2$.

The laboratory microcosms were prepared in 250 mL Wheaton bottles (Wheaton Co., Miliville, N.J.) within the anaerobic chamber. Duplicate microcosms were prepared for the following conditions: Killed Control (live soil autoclaved for 1 hr on 2 consecutive days), Live soil, and Live soil+0.05% yeast extract. Each microcosm contains 20% soil and 80% BTZ-3 media ($NH_4Cl$, 4.3 g/L; $KH_2PO_4$, 50 g/L; $MgCl$-$6H_2O$, 20 g/L; $CaCl_2$-$2H_2O$, 1 g/L; HEPES, 50 mM/L; mineral solution (6.4 g of Nitrilotriacetic acid, 0.05 g of $MnCl_2$-$4H_2O$, 0.15 g of $FeCl_2$-$4H_2O$, 0.16 g of $CoCl_2$-$6H_2O$, 0.05 g of ZnCl, 0.03 g of $CuCl_2$-$2H_2O$, 0.09 g of $NiCl_2$-$6H_2O$, 0.005 g of $NaMoO_4$-$2H_2O$, and 0.005 g of $H_3BO$ into 450 mL of deionized water, and adjust pH to 7.0 with 1N NaOH), 10 mL/L; resazurin 0.2%, 5 mL/L). The microcosm were filled to top such there was little or no headspace, and then stoppered with Teflon™ lined disks and crimp-sealed with aluminum seals (Wheaton Co.). The resazurin addition permitted the visualization of low potential anaerobic conditions by a color change from pink to colorless. Each microcosm was spiked with 5 ppm from a PCE or TCE solution saturated in water. The microcosms were incubated on their sides in the anaerobic chamber, in the dark, at ambient room temperature (22° C.) for up to 180 days.

Samples were analyzed the next day as time zero ($t_0$) and then twice a week for the dechlorination of PCE or TCE and the formation of cDCE, vinyl chloride or methane. All samples were taken in the anaerobic chamber by using a syringe mounted with a 23 gauge needle to puncture the Teflon™ septa and to obtain a 5 mL liquid sample that was injected into a 10 mL headspace vial. Samples were tested for the presence of chloroethenes and ethene using a Hewlett-Packard 5890 Series II Gas Chromatograph (GC) fitted with a ChromPack CP-PoraPLOT Q-HT fused silica WCOT 25 m×0.53 mm I.D×0.2 μm column (Varian, #CP 7559, Walnut Creek, Calif.) and a flame ionization detector (FID). The injector temperature was set at 200° C., and the detector temperature was set at 250° C. The oven temperature was programmed as follows: 45° C. ramped up to 180° C. at 30° C./min, held for 8 min, increased to 195° C. at 25° C./min, held for 4 min, increased to 250° C. at 25° C./min and held for 10 minutes. The carrier gas was helium at a flow rate of 10 mL/min. Aqueous samples (5 mL) were dispensed into 10-mL headspace vials (HP#5182-0838) and sealed with Teflon-coated/butyl septa with aluminum crimp caps (HP#5183-4480). Headspace vials were placed in the vial tray of a Hewlett-Packard headspace autosampler (HP 7694) for subsequent automated injection of the headspace (gas phase) samples onto the GC. The headspace sampler was programmed to heat each sample to 80° C. for 13 minutes prior to injection. Calibration was performed using custom made external standards purchased from Ultra Scientific. These concentrated stock solutions were diluted in water to make standard solutions for calibration. This method, which is a modification of ChromPack Application Note #1268-GC Rev. 3 (ChromPack, Varian USA, Walnut Creek, Calif.; personal communication, Robert J. West, Dow Chemical), detected the chloroethenes and ethene.

FIG. 3 plots the concentration (parts per million; ppm) of chloroethenes in the microcosm medium as a function of time (days) and illustrates the dechlorination of chloroethenes. Dechlorination of PCE to TCE could be detected by GC/FID. Within two days with the formation of cDCE from the dechlorination of TCE was detected. These results are found in the microcosms that were amended with 0.05% yeast extract plus minimal salts media (BTZ-3 media). These results can also be seen in the microcosms that were amended with the minimal salts media alone. The difference is the dechlorination is slightly delayed. It takes four days before cDCE is detected. Degradation of cDCE would occur over the next two weeks. Vinyl chloride and ethene in FIG. 3 could only be detected at trace levels. The "Killed" control did not show degradation of PCE or TCE during the duration of the experiment. Cell growth was shown by increase in the turbidity of the microcosm medium and by microscopic analysis.

Example 2

Generation of PCR Primers and Probes for the Amplification and Detection of the *Dehalococcoides ethenogenes* 16S rRNA Profiled The detection and sequencing of the *Dehalococcoides ethenogenes*-like organisms required a set of PCR primers as shown in Table 1 (SEQ ID NOs:9–29). The PCR primers were designed using signature seq determine the location of these signature sequences, the *Dehalococcoides ethenogenes* sequence (GenBank No. AF004928; SEQ ID NO:7) and two putative *Dehalococcoides* 16S rRNA sequences, each from one of two microcosm cultures known to dechlorinate chloroethenes (DHE-Pin, which was isolated within the present invention from the Pinellas culture that is described in Harkness et al. *Environ. Sci. Technol.* 33: 1100 (1999); and DHE V/SFD, as described in Yang et al. *Sci. Technol.* 32:3591(1998)) were aligned using MEGALIGN (DNAstar, Madison, Wis.) or Pileup (Genetics Computer Group, Madison, Wis.) with 16S rRNA sequences from 100 organisms that represent most major domains, families and genera in the major kingdoms of Bacteria and Archaea. The conserved, variable, and highly variable regions could be delineated by boxing off the consensus sequences. Primer candidate sequences were manually picked from the variable and highly variable regions and then their uniqueness was determined by determining their potential as probes to ribosomal sequence database sequences using the "on-line" Probe Match Program from the Ribosomal Database Project II, RDPII, Michigan State University, East Lansing, Mich.). This analysis returned an overview of the matches between a probe and its potential target sequence, as a listing and as a phylogenetic overview. The program results showed the sequences that match the query sequence (if there are such sequences) and also showed sequences that had mismatches, deletions and insertions, citing the number and positions of the aberrations.

The sequences that were unique and passed this test as signature sequences were then designed as either a forward or reverse primer, usually dependent on their position in the sequence. The most unique sequence of the signature sequence (specificity) was designed into the 3' end in either type of primer. The selected primers are shown in Table 1.

The primers were synthesized using standard β-cyanoethyl phosphoramidite coupling chemistry on controlled pore glass (CPG) supports on an automated DNA oligonucleotide synthesizer (Applied Biosystems Model 392, Perkin-Elmer, Foster City, Calif.).

TABLE 1

Primers for *Dehalococcoides ethenogenes*-like organisms

| | | |
|---|---|---|
| FP DHE 32 | 5' AAG TCGAACGGTCTTAAGCA 3' | (SEQ ID NO:9) |
| RP DHE422 | 5' CGTCATTATTCTTCCCTGTG 3' | (SEQ ID NO:10) |
| FP DHE 958 | 5' GGGAAACGACCTGTTAAGTCA 3' | (SEQ ID NO:11) |
| RP DHE 1212 | 5' GGATTAGCTCCAGTTCACACTG 3' | (SEQ ID NO:12) |
| RP DHE 1076 | 5' AAATTTAACTAGCAACAAGG 3' | (SEQ ID NO:13) |
| FP DHE 775 | 5' GGAGTATCGACCCTCTCTG 3' | (SEQ ID NO:14) |
| FP DHE 774 | 5' GGGAGTATCGACCCTCTC 3' | (SEQ ID NO:15) |
| FP DHE 946 | 5' AGTGAACCGAAAGGGAAA 3' | (SEQ ID NO:16) |
| FP DHE 385 | 5' GGGTTGTAAACCTCTTTTCAC 3' | (SEQ ID NO:17) |
| RP DHE 806 | 5' GTTAGCTTCGGCACAGAGAG 3' | (SEQ ID NO:18) |
| RP DHE 692 | 5' TCAGTGACAACCTAGAAAAC 3' | (SEQ ID NO:19) |
| FP DHE1 | 5' GATGAACGCTAGCGGCG 3' | (SEQ ID NO:20) |
| FP DHE 30 | 5' GTGCCTTATGCATGCAAG 3' | (SEQ ID NO:21) |
| FP DHE 1187 | 5' AATAGGTTGCAACAGTGTGAA 3' | (SEQ ID NO:22) |
| FP DHE 1175 | 5' AATGGACAGAACAATAGGTTGC 3' | (SEQ ID NO:23) |
| RP DHE 1381 | 5' GGCACATCGACTTCAAGTGTT 3' | (SEQ ID NO:24) |
| FP DHE 385A | 5' GGGTTGTAAACCTCTTTTCA 3' | (SEQ ID NO:25) |
| FP DHE 558 | 5' TAACCGGGACG(AT)GTCATTCA 3' | (SEQ ID NO:26) |
| FP DHE 593 | 5' GAGTACAGCAGGAGAAAAC 3' | (SEQ ID NO:27) |
| RP DHE 1387 | 5' CCTCCTTGCGGTTGGCACATC 3' | (SEQ ID NO:28) |
| RP DHE 1090 | 5' GGCAGTCTCGCTAGAAAAT 3' | (SEQ ID NO:29) |
| dAB pDHE A (141–173) | 5' TGTGATGGGCTGACATAAGTCGGTTCATTAAAGCCGCAAGGTG 3' | (SEQ ID NO:35) |
| | 5' CACCTTGCGGCTTTAATGAACCGACTTATGTCAGCCCATCACA 3' | (SEQ ID NO:36) |
| pDHE B (141–173) | 5' TGTGGTGGGCCGACATAAGTTGGTTCACTAAAGCCGTAAGGTG 3' | (SEQ ID NO:37) |
| | 5' CACCTTACGGCTTTAGTGAACCAACTTATGTCGGCCCACCACA 3' | (SEQ ID NO:38) |

TABLE 1-continued

Primers for Dehalococcoides ethenogenes-like organisms

| | | | |
|---|---|---|---|
| pDHE C (141–173) | 5' | TGTGGTGGGCCGACATATGTTGGTTCACTAAAGCCGTAAGGCG 3' | (SEQ ID NO:39) |
| | 5' | CGCCTTACGGCTTTAGTGAACCAACATATGTCGGCCCACCACA 3' | (SEQ ID NO:40) |
| pDHE (1068–1105) | 5' | AGTTAAATTTTCTAGCGAGACTGCCCCGCGAAACGG 3' | (SEQ ID NO:41) |
| | 5' | CCGTTTCGCGGGGCAGTCTCGCTAGAAAATTTAACT 3' | (SEQ ID NO:42) |
| pDHE (1068–1096) | 5' | AGTTAAATTTTCTAGCGAGACTGCCCCGC 3' | (SEQ ID NO:43) |
| | 5' | GCGGGGCAGTCTCGCTAGAAAATTTAACT 3' | (SEQ ID NO:44) |
| pDEH (1057–1086) | 5' | CCTTGTTGCTAGTTAAATTTTCTAGCGAGA 3' | (SEQ ID NO:45) |
| | 5' | TCTCGCTAGAAAATTTAACTAGCAACAAGG 3' | (SEQ ID NO:46) |
| pDHE (932–963) | 5' | GACATGCATGAAGTAGTGAACCGAAAGGGAAA 3' | (SEQ ID NO:47) |
| | 5' | TTTCCCTTTCGGTTCACTACTTCATGCATGTC 3' | (SEQ ID NO:48) |
| pDHE (565–594) | 5' | GGACGTGTCATTCAATACTGTTGGACTAGA 3' | (SEQ ID NO:49) |
| | 5' | TCTAGTCCAACAGTATTGAATGACACGTCC 3' | (SEQ ID NO:50) |
| pDHE (582–613) | 5' | TGTTGGACTAGAGTACAGCAGGAGAAAACGGA 3' | (SEQ ID NO:51) |
| | 5' | TCCGTTTTCTCCTGCTGTACTCTAGTCCAACA 3' | (SEQ ID NO:52) |
| pDHE (555–582) | 5' | GGCTTAACCGGGACGTGTCATTCAATACT 3' | (SEQ ID NO:53) |
| | 5' | AGTATTGAATGACACGTCCCGGTTAAGCC 3' | (SEQ ID NO:54) |
| pDHE (547–582) | 5' | AATTTCCCGGCTTAACCGGGACGTGTCATTCAATACT 3' | (SEQ ID NO:55) |
| | 5' | AGTATTGAATGACACGTCCCGGTTAAGCCGGGAAATT 3' | (SEQ ID NO:56) |
| pDHE (969–999) | 5' | TGTTAAGTCAGGAGTTTGCACAGGTGCTGCA 3' | (SEQ ID NO:57) |
| | 5' | TGCAGCACCTGTGCAAACTCCTGACTTAACA 3' | (SEQ ID NO:58) |
| pDHE (80–110) | 5' | CGCGTAAGTAACCTACCTCTAAGTGGGGGAT 3' | (SEQ ID NO:59) |
| | 5' | ATCCCCCACTTAGAGGTAGGTTACTTACGCG 3' | (SEQ ID NO:60) |

Example 3

Using the Dehalococcoides ethenocienes-like Specific Primers to Detect These Organisms in Microcosms Nucleic acids were extracted from the microcosm cultures of Example 1 by a bead mill homogenization procedure, FastDNA Spin Kit for Soil (Bio 101, Vista, Calif.), that was designed to isolate genomic DNA from all cell types. Approximately 10 mL of the microcosm culture was pelleted and resuspended in 500 ul of the culture media. The resuspended pellet was added to a 2.2 mL conical screw-cap tube containing 1.5 g of three differently sized glass and zirconia/silica beads (106 microns, 710–1180 microns). To the sample tubes, 978 ul of sodium phosphate buffer and 122 ul of MT buffer were added. The tubes were homogenized for 30 sec at speed 5.5 on a Fast Prep bead mill homogenizer. A clear supernatant was obtained by centrifuging the samples at 14,000×g for 30 sec. The supernatant was transferred to a clean microcentrifuge tube and 250 ul of PPS reagent was added and mixed. The resulting precipitate was pelleted through centrifugation at 14,000×g for 5 min. The supernatant was transferred to a new microcentrifuge tube and 1 mL of binding matrix was added. The samples were placed on a rotator for 2 min and then sat on the bench-top for 3 min to allow the settling of the silica matrix. Between 500–700 ul of the supernatant was removed and discarded. The remaining supernatant was used to resuspend the silica matrix and transferred to a spin filter. The spin filter was centrifuged for 1 min at 14,000×g and the flow-through decanted. The silica matrix was washed with 500 ul of SEWS-M buffer and centrifuged for 1 min at 16,000×g. The flow through was discarded and any residual buffer in the matrix was removed by a 2 min centrifugation at 14,000×g. The spin filter was placed in a catch tube and air-dried for 5 min in a biological hood. The genomic DNA was eluted by adding 60 ul of sterile, deionized water, mixing the matrix and the water together with a pipet tip, and centrifuging for 1 min at 14,000×g.

The 16S rRNA gene for Dehalococcoides ethenogenes-like organisms was detected by PCR amplification and gel electrophoresis. The 16S sequences were amplified using Dehalococcoides ethenogenes specific 16S rDNA primers shown in Table 1 (from Example 2). All PCR amplifications were performed using the GeneAmp PCR kit with Taq DNA polymerase (PE Applied Biosystems, Branchburg, N.J.) in a Perkin Elmer 9600 thermal cycler. Amplification reactions contained 10 mM Tris-HCl (pH 8.3), 50 mM KCl, 1.5 mM $MgCl_2$, 10 $\mu M$ each deoxynucleoside triphosphate, 20 pmol each primer, 2.5 U of Taq polymerase, and 1 $\mu L$ of the genomic extraction (or between 1 and 5 μL of 1:10 dilution of the genomic extraction) in a final reaction volume of 50 μL. Alternatively, a direct detection protocol used 1 μL of the microcosm culture directly added to the PCR as described previously. The PCR conditions were as follows: 2 min of denaturation at 95° C., followed by 30 cycles of 30 sec at 94° C., 30 sec at 55° C., and 30 sec at 72° C. 8 μL of the PCR product were visualized on a 2% agarose gel (SeaKem GTG, FMC BioProducts, Rockland, Me.) stained with ethidium bromide.

After the *Dehalococcoides ethenogenes*-like sequences were detected in the microcosm developed from contaminated soil, FP DHE 1 (SEQ ID NO:20) and RP DHE 1212 (SEQ ID NO:12) were used to amplify a 1212 bp fragment, which was cloned (using the PCR dA/T-Cloning System, Invitrogen, Inc., CA) and sequenced (using Model 377 DNA Sequencer kit and system, Applied Biosystems, Perkin-Elmer, Foster City, Calif.). The sequence was assembled using the Seqman II program (DNAstar, Inc., Madison, Wis.). The 16S rDNA sequence contig formed was compared to 16S rDNA sequences obtained from microcosms developed from contaminated soils from other sites and the comparison is shown in FIG. 4.

Figure 4:
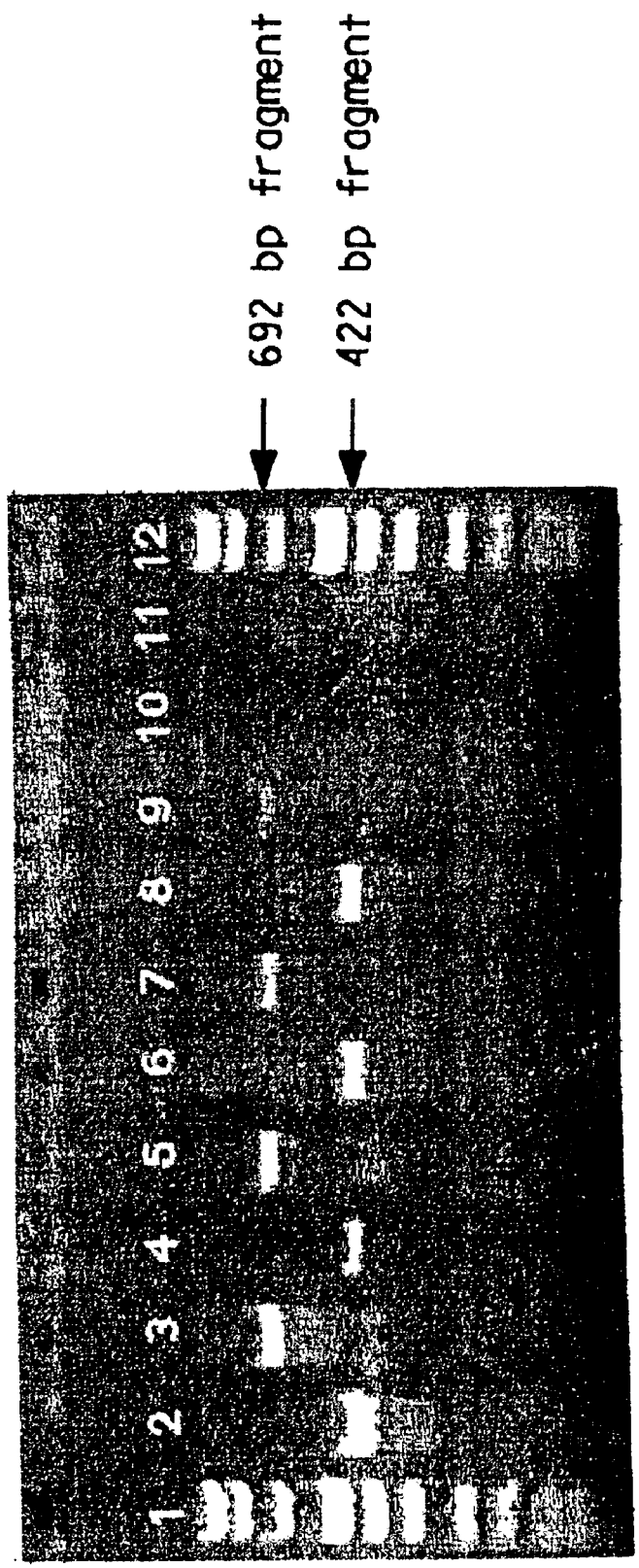
FIG. 4 is an image of an electrophoresis gel used to detect PCR products in a test of soils contaminated with chloroethenes using two sets of the primers described herein.

FIG. 4 shows a gel of amplification products generated from PCR amplification of various *Dehalococcoides ethenogenes*-like organisms isolated from a number of industrial sites contaminated with either PCE or TCE. All amplifications were carried out using primers SEQ ID NOs:17 paired with 19, and SEQ ID NOs:18 paired with 20. Lanes 1 and 12 carry the molecular weight markers. Lanes 2 and 3 are the PCR products generated from organisms isolated from soil containing PCE. Lanes 4, 5, 6, 7, 8 and 9 are the PCR products from organisms isolated from soil containing TCE. Lanes 10 and 11 contain negative PCR controls. As can be seen by the data, all samples were detectable by the primers used.

The contiguous sequences from each site were unique, having 96 to 99% similarity to each other. The differences in the sequences are annotated in Table 2. A major difference exists in the consensus sequence (CS) that was obtained from all organisms detected at contaminated sites and the reference sequence represented by the published sequence from strain DHE-195 (Table 2). At DHE (CS) positions 1088–1096 (*E. coli* coordinates E1146–E1156) there exists a nine base deletion. The sequence in CS organisms reads ATTTTCTAGCGAGACTG (SEQ ID NO:31); in the DHE-195 strain it reads ATTTTCTAGCGAGACTAGCGAGACTG (SEQ ID NO:32) (the double underlined sequence is the sequence deleted in the CS organism sequences. Differences in sequence were found at six other base positions as shown below in Table 2.

TABLE 2

| E. coli | DHE No. | DHE-195 | | DHE-Pl | | DHE-V/SFD | | DHE DII | | DHE Pln | | Sig. Grp |
|---|---|---|---|---|---|---|---|---|---|---|---|---|
| 28 | 1 | | 1 | | 1 | | 1 | | 1 | | 1 | |
| 107 | 66 | A | 66 | A | 66 | A | 66 | A | 66 | G | 66 | 6A |
| 184 | 144 | A | 144 | A | 144 | G | 144 | G | 144 | G | 144 | 2A |
| 190 | 150 | T | 150 | T | 150 | C | 150 | C | 150 | C | 150 | 2B |
| 198 | 157 | A | 157 | A | 157 | A | 157 | A | 157 | T | 157 | 6B |
| 201 | 160 | C | 160 | C | 160 | T | 160 | T | 160 | T | 160 | 2C |
| 208 | 167 | T | 167 | T | 167 | C | 167 | C | 167 | C | 167 | 2D |
| 217 | 176 | C | 176 | C | 176 | T | 176 | T | 176 | T | 176 | 2E |
| 222 | 181 | T | 181 | T | 181 | T | 181 | T | 181 | C | 181 | 6C |
| 264 | 226 | T | 226 | T | 226 | C | 226 | C | 226 | T | 226 | 3A |
| 267 | *229 | T | 229 | C | 229 | C | 229 | C | 229 | C | 229 | 1A |
| 291+ | 254 | d | 253+ | d | 253+ | T | 254 | d | 253+ | d | 253+ | 5A |
| 333 | *296 | G | 295 | C | 295 | C | 296 | C | 295 | C | 295 | 1B |
| 420 | 383 | T | 382 | T | 382 | C | 382 | C | 382 | T | 382 | 3B |
| 444 | 407 | C | 406 | C | 406 | C | 407 | C | 406 | T | 406 | 6D |
| 542 | *481 | G | 480 | d | 479+ | d | 480+ | d | 479+ | d | 179+ | 1C |
| 631 | 571 | T | 570 | T | 596 | T | 570 | T | 569 | A | 569 | 6E |
| 829 | 769 | G | 768 | G | 767 | A | 768 | G | 767 | G | 767 | 5B |
| 933 | 874 | G | 873 | T | 872 | G | 873 | G | 872 | G | 872 | 4A |
| 934 | 875 | C | 874 | T | 873 | C | 874 | C | 873 | C | 873 | 4B |
| 980 | *921 | d | 919+ | C | 919 | C | 920 | C | 919 | C | 919 | 1D |

TABLE 2-continued

| E. coli | DHE No. | DHE-195 | | DHE-Pl | | DHE-V/SFD | | DHE DII | | DHE Pln | | Sig. Grp |
|---|---|---|---|---|---|---|---|---|---|---|---|---|
| 1003 | 944 | A | 942 | A | 942 | A | 943 | A | 942 | T | 943 | 6F |
| 1012 | 955 | C | 953 | C | 953 | C | 954 | C | 953 | T | 953 | 6H |
| 1020 | 963 | A | 961 | A | 961 | A | 962 | A | 961 | G | 961 | 6I |
| 1039 | 984 | G | 982 | G | 982 | G | 983 | G | 982 | A | 982 | 6J |
| 1040 | 985 | T | 983 | T | 983 | T | 984 | T | 983 | C | 983 | 6I |
| 1087 | *1033 | G | 1031 | T | 1031 | T | 1032 | T | 1031 | T | 1031 | 1E |
| 1114 | *1060 | d | 1057+ | C | 1058 | C | 1059 | C | 1058 | C | 1058 | 1F |
| 1144–56 | *1088–96 | 1086–94 ACTAGCGAG | | d | 1085+ | d | 1086+ | d | 1085+ | d | 1085+ | 1G |
| 1284 | 1225 | C | 1220 | C | 1213 | T | 1214 | T | 1213 | C | 1213 | 3C |
| 1364 | 1304 | A | 1300 | A | 1292 | A | 1293 | A | 1292 | T | 1292 | 6K |
| 1427 | 1357 | N | 1353 | A | 1345 | A | 1346 | A | 1346 | A | 1346 | 1H |

"DHE No." represents Consensus sequence number;
Sequence number with (+) represents last base coordinate before a base a deletion;
Bold bases are indicative of base sequences different from DHE 195;
Bold bases and blockscells (base and coordinate) imply sequence of all 16S sequences isolates that are different from DHE strain 195
"Sig Grp" indicates which set of Signature Sequences Set a bases belongs to.
"1(Letter)" Signature group: sequences in entire DHE group 16S rDNA sequence are different from Cornell strain 195 at designated positions
"2(Letter)" Signature group: sequences are unique to DHE (V/SFD), DHE (DII) and DHE (Pnl/Dab) at designated intervals
"3(Letter)" Signature group: sequences are unique to DHE (V/SFD), and DHE (DII) at designated positions
"4(Letter)" Signature group: sequences are unique to DHE (PI) at designated positions
"5(Letter)" Signature group: sequences are unique to DHE (V/SFD) at designated positions
"6(Letter)" Signature group: sequences are unique to DHE (Pnl/Dab) at designated positions All sequences generated using species-specific primers for *Dehalococcoides ethenogenes* were found to have identity with *Dehalococcoides ethenogenes* Strain 195. Sequence identities ranged from 98.5 to 99.6% and were defined as "*Dehalococcoides ethenogenes*-like" sequences since the 16 S rDNA sequences did not completely match the 16S rDNA sequence of Strain 195. The PCR products produced by either FP DHE 1 (SEQ ID NO:20) and RP DHE 1212 (SEQ ID NO:12) or FP DHE 1 (SEQ ID NO:1) and RP DHE 1387 (SEQ ID NO:28) were the longer amplified products (1212 or 1387 bp in length, respectively). The differences between each sequence and the sequence of *D. ethenogenes* Strain 195 (GenBank AF004928), are shown in Table 2. The *Dehalococcoides ethenogenes*-like 16S rDNA sequences from any one contaminated site were different than those *Dehalococcoides ethenogenes*-like 16S rDNA sequences obtained from microcosm samples from the other sites. PCR products, which were taken at different time points from the same microcosms, also yielded the same 16S rDNA sequence. It appears that the *D. ethenogenes*-like 16S rDNA sequences are unique to the specific site of origin. All four 16S rDNA sequences were found to be different from Strain 195 sequence at seven sequence positions (designated by 1A to 1G signature positions, Table 2 in the "Sig. Grp" column). There are three single base substitutions (1A, 1B and 1E), one single-base deletion (1C) and two single-base insertions (1D and 1F). All sequences also shared a nine base deletion located at Strain 195 base number 1085 (Table 2).

The DHE-PI 16S rDNA sequences were the closest to the 16S rDNA sequence of Strain 195 (99.6% identity). It has nine base changes (signature groups 1 and 4, Table 2): 6 base substitutions, one deletion (excluding the 9 base deletion error) and 2 insertions). The DHE-Pin 16S rDNA sequence was the most distant from Strain 195 with 24 base changes (98.5% identity, signature groups 1, 2, 6 in Table 2). The DHE-V/SFD (99.1% identity) and the DHE-DII (99.2% identity) 16S rDNA sequences were found to share 15 differences (signature group 1, 2 and 3 in Table 2) from the sequence of Strain 195. In addition, the DHE-V/SFD sequence differed from the DHE-DII sequence with a single base insertion (5A) and a single base substitution (5B).

Signature sequences 2 and 6 have unique base substitutions that distinguish the 16S rDNA sequences that are found in the DHE V/SFD culture, the DHE-DII and the DHE-Pin from the Strain 195 16S rDNA sequence. The DHE-V/SFD and DHE-Pin 16S rDNA sequences have base substitutions at base positions: 144 (A→G), 150 (T→C), 160(C→T), 167 (T→C) and 176 (C→T). Further, the DHE-Pin 16S rDNA sequence has base substitutions in region 2 at base positions: 157 (A→T) and 181(T→C) that makes its sequence different from those of Strain 195, DHE-PI, DHE-DII and DHE-V/SFD. These base substitutions in region 2 are conserved (Table 2, Signature groups 2A to 2E and 6A to 6B) and are being used in the signature sequence definitions of these 16S rDNA sequences. The DHE-PI 16S rDNA sequence in signature sequence 2 is identical to Strain 195. The DHE-DII 16S rDNA sequence in signature sequence 2 is identical to the DHE-V/SFD sequence.

In signature sequence 6, the DHE-Pin 16S sequence is different from the sequences of all the other *Dehalococcoides ethenogenes*-like 16S rDNA sequences, including that of Strain 195. Its sequence has base substitutions at base positions: 942 (A→T), 952 (C→T), 961 (A→G), 982 (G→A) and 983 (T→C) (Table 2, 6 F to 6 K). In conjunction with signature sequence 2, signature sequence 6 is used to define of the DHE-Pin 16S rDNA sequence.

Example 4

Using the *Dehalococcoides ethenogenes*-like Specific Primers and Probe to Detect *Dehalococcoides* in a Test-Kit This Example demonstrates the detection of *Dehalococcoides ethenogenes*-like organisms in a test kit using the 16S rRNA gene sequences for test primers and probe reagents.

Materials

The following reagents and materials for assembly of the test kit were purchased commercially. Nitrocellulose membrane (5.0 µm porosity) was purchased from Schleicher & Schuell (Keene, N.H. 03431) as 15 cm×15 cm sheets. Alkaline phosphatase NBT/BCIP substrate (0.12 mM) was purchased from Moss, Inc., (Pasadena, Md. 21123-0189), and Streptavidin from ZYMED Lab., Inc. (CA). Anti-Digoxigenin Alkaline Phosphatase Conjugate Fab fragments (1093-274) and Digoxigenin-11-dUTP (1558706) were purchased from the Boehringer Mannheim Corp. Adsorptive pads (0.33 mm thickness) were purchased from VWR Scientific (28303) and pad #50970 from Schleicher & Schuell (Keene, N.H. 03431).

Preparation of Test Kit Reagents

Lateral Flow buffer for the test kit was prepared containing 10 mM Tris Base (pH 8.0), (J. T. Baker Inc., Phillipsburg, N.J.), 150 mM NaCl, 1 mM $MgCl_2$, 0.1 mM $ZnCl_2$, 0.5% bovine serum albumen, and 0.1% Triton X100 in purified water.

Wash Buffer for the test kit was prepared containing 100 mM Tris Base (pH 9.5; J. T. Baker Inc., Phillipsburg, N.J.), 100 mM NaCl, and 50 mM $MgCl_2$, in purified water.

Detection probes and primers for the test kit were based on the *Dehalococcoide* sequences in Table 1. The primers and probes were synthesized using standard cyanoethyl phosphoramidite chemistry on a Perkin Elmer Biosystems model 392. The probe labels (N) were substituted for nucleotides during synthesis using commercially labeled phosphoramidite reagents that possess either a 2 aminobutyl-1,3-propanediol backbone or a 1-(1,2 diaminoethane) 3-deoxyfructonic acid. In the sequence, cordycepin 5' triphosphate (3'deoxyadenosine) is indicated by "dA" and biotin Label-ON Phosphoramidite® (Clontech, Palo Alto, Calif.) by "B". Specifically, the following primers and probes were used in detection:

*Dehalococcoides ethenogenes* Target-specific Primers

Forward Primer DHE 385: (SEQ ID NO:17)

Reverse Primer DHE 807(806): (SEQ ID NO:18)

Detection Probe (Biotin labeled) dD-B DHE 555 B2:

5'BGGCTTAACCGGGACGTGTCATTCAATACBdA 3' (SEQ ID NO:53).

A test strip capture reagent was prepared for the test kit assay by printing Streptavidin (0.1 µL of 5 mg/ml) either as a transverse line across a nitrocellulose membrane or as a alpha numeric letter (Schleicher &Schull, Keene, N.H., >5µ porosity). The Streptavidin was printed near the efferent end (capture zone) of the membrane. Prior to use, the printed membrane was then stored in a desiccator at room temperature for 3 days. The test strip membrane was then supported horizontally in a plastic holder. An adsorbent pad 0.33 mm in thickness (VWR Scientific, #28303) was then placed on the test strip ca. 1 cm above the capture zone to adsorb and collect test fluids.

Sample DNA Extraction and Detection

DNA for detection in the test kit was prepared as follows. The nucleic acids were extracted from dechlorinating microcosm cultures by a bead mill homogenization procedure, FastDNA Spin Kit for Soil (Bio 101, Vista, Calif.), that was designed to isolate genomic DNA from all cell types. Procedures for the kit followed the manufacturer's recommendations. Approximately 1 to 10 mL of the microcosm culture was pelleted and resuspended in 500 µl of the culture media. The resuspended pellet was added to a 2.2 mL conical screw-cap tube containing 1.5 g of three differently sized glass and zirconia/silica beads (106 microns, 710–1180 microns). To the sample tubes, 978 µl of sodium phosphate buffer and 122 µl of MT buffer were added. The tubes were homogenized for 30 sec at speed 5.5 on a Fast Prep bead mill homogenizer. A clear supernatant was obtained by centrifuging the samples at 14,000×g for 30 sec. The supernatant was transferred to a clean microcentrifuge tube and 250 µl of PPS reagent was added and mixed. The resulting precipitate was pelleted through centrifugation at 14,000×g for 5 min. The supernatant was transferred to a new microcentrifuge tube and 1 mL of binding matrix was added. The samples were placed on a rotator for 2 min and then sat on the benchtop for 3 min to allow the settling of the silica matrix. Between 500–700 µl of the supernatant was removed and discarded. The remaining supernatant was used to resuspend the silica matrix and transferred to a spin filter. The spin filter was centrifuged for 1 min at 14,000×g and the flow-through decanted. The silica matrix was washed with 500 ul of SEWS-M buffer and centrifuged for 1 min at 16,000×g. The flow through was discarded and any residual buffer in the matrix was removed by a 2 min centrifugation at 14,000×g. The spin filter was placed in a catch tube and air dried for 5 min in a biological hood. The genomic DNA was eluted by adding 60 ul of sterile, deionized water, mixing the matrix and the water together with a pipette tip, and centrifuging for 1 min at 14,000×g.

Following extraction, the 16S rRNA gene for *Dehalococcoides ethenogenes* was amplified by PCR and the *Dehalococcoides ethenogenes* specific DNA products detected in the test kit. In this process, the PCR amplifications were performed by using the GeneAmp PCR kit with AmpliTaq® DNA polymerase (PE Applied Biosystems, Branchburg, N.J.) in a Perkin Elmer 9600 thermal cycler. Amplification reactions contained 10 mM Tris-HCl (pH 8.3), 50 mM KCl, 1.5 mM $MgCl_2$, 100 µM each deoxynucleotide triphosphate, 20 pmol each primer, 0.5 U of AmpliTaq® polymerase, 20 pmoles detection probe, 1 nmole of Digoxigenin-11-dUTP 1 µL of the genomic extraction (or between 1 and 5 µL of 1:10 dilution of the genomic extraction) in a final reaction volume of 50 µL. The PCR conditions were as follows: 2 min of denaturation at 95° C., followed by 30 cycles of 30 sec at 94° C., 30 sec at 55° C., and 30 sec at 72° C.

The *Dehalococcoides* 16S rRNA gene products could be detected using one of two detection methods: agarose gel electrophoresis and lateral flow membrane. In the Lateral flow method, the PCR test reaction mixture (10 µL) was diluted with 70 µL of lateral flow buffer. The membrane holder was placed horizontally on a bench top. The diluted PCR products (70 µL) were then applied to the sample end of the test strip and allowed to wick through the membrane reagent. This is accomplished in ca. 5 min. Diluted conjugate reagent (80 µl), prepared as a 1:25 fold dilution of the anti-digoxigenin alkaline phosphatase conjugate (Boehringer Mannheim Corp. (#1093-274) in lateral flow buffer, was then added to the sample end of the membrane and allowed to wick through the membrane and equilibrate for 10 min. This was followed by addition of 80 µL of a wash buffer to the sample end of the membrane. After 10 min, 90 L of BCIP/NBT alkaline phosphatase substrate reagent (Moss Inc., Pasadena, Md. 21123-0189; product NBTM- 1000) was added at the sample end and allowed to wick through the membrane. Test results were then read after 10 min by visually inspecting the membrane DNA capture zone. The presence of 16S RNA gene products are evident by the formation of blue color in the form of the Streptavidin capture reagent printed on the membrane (line or alpha numeric test symbol). A visual color response exceeding background color of the membrane is indicative of the presence of the *Dehalococcoides* organisms DNA in the test sample.

In the gel electrophoresis method, 8 μL of the PCR product was visualized on a 2% agarose gel (SeaKem GTG, FMC BioProducts, Rockland, Me.) in 1×TBE buffer at 50 V for 30 min and stained with ethidium bromide (0.5 μg/mL). The HinfI fragments MW marker from Gibco BRL (Gaithersburg, Md.), the 1-kb ladder from Gibco-BRL, or the Boehringer Mannheim MW Marker VIII (Boehringer GmbH, Mannheim, Germany) were used as molecular size markers. To measure product yield in a PCR reaction for a dose-response assay or semi-quantification of 16S rDNA PCR product bands, the ethidium bromide stained gels were imaged using the Eagle Eye II Still Video System (Stratagene, La Jolla, Calif.). The electronic images were analyzed for DNA band intensities using NIH Image 1.62 (Rasband et al., *Microbeam Anal.* (Deerfield Beach, Fla.) (1995), 4(3), 137–49).

Example 5

Generation of PCR Primers and Probes for the Amplification and Detection of the *Dehalococcoides* 16S rRNA Using a More Stringent Amplification Assay The detection and sequencing of the *Dehalococcoides* organisms in this example used a set of PCR primers that permitted greater stringency in amplification as compared to previous work described in Example 2.

New PCR primers were designed using signature sequence regions. The locations of these signature sequences were determined using the same methods as those outlined in Example 2. Once signature sequences were identified, either a forward or reverse primer was designed according to the primer's position in the sequence. To develop primers with higher annealing temperatures and specificity of detection for amplification, the primers had to meet the following specifications.

(1) For greater specificity, the most unique sequence of the signature sequence region was designed into the 3' end in either type of primer (i.e., forward or reverse primer);

(2) For increased binding stability, the length of the primer at the 5' end was increased until the desired annealing temperatures were obtained (between 55° C. and 65° C.);

(3) The sequences should not form hairpin structures that develop at temperatures greater than 55° C. or become stabilized during the PCR reaction so that they do not interfere in the efficiency of the assay; and (4) Primer pairs should be matched for PCR so that they do not form stable 3' dimer structures that can be used for priming polymerase extension at temperatures greater than 50° C.

The difference in these primer sets are that their optimal annealing temperatures are at least (on average) 10° C. higher than those primers found in Table 1. These high annealing temperatures allow the PCR temperature cycling programs to have higher annealing temperatures, thereby resulting in the elimination of non-specific PCR products. The result is a more robust PCR assay with lower probability for the formation of non-specific fragments and for interpretation of false positives in the assay.

The selected primers are shown in Table 3, as SEQ ID NOs: 61–75. The primers were synthesized using standard β-cyanoethyl phosphoramidite coupling chemistry on controlled pore glass (CPG) supports on an automated DNA oligonucleotide synthesizer (Applied Biosystems Model 392, Perkin-Elmer, Foster City, Calif.). The primers were tested after they were synthesized using PCR on dechlorinating samples taken from microcosms known to have *Dehalococcoides* organisms. These dechlorinating samples were similar to those used to test previous primers (Table 1 primers, in Example 3) and therefore included samples from DHE-PL, DHE-V/SFD, DHE-DAB, DHE-PIN, and DHE-DLL.

All PCR amplifications were performed using a Perkin-Elmer GeneAmp® 9600 thermal cycler and the GeneAmp PCR kit (P-E, Applied Biosystems, Norwalk, Conn.). The PCR reactions contained 1×PCR Buffer (10 mM Tris-HCl, pH 8.3; 50 mM KCl), 1.5 mM $MgCl_2$, 10 μM of each deoxynucleoside triphosphate, 20 pmol of each primer (a forward primer and a reverse primer from Table 3), 2.5 U of Taq polymerase, and 1 μL of the genomic extraction (or between 1 and 5 μL of 1:10 dilution of the genomic extraction) in a final reaction volume of 50 μL. The following PCR thermocycling program was used: 2 min of denaturation at 95° C., followed by using either 30 or 40 cycles of 1 min at 94° C., 1 min at 60° C., 1 min at 72° C. and finally cooled to 4° C. The PCR products are detected using the same methods as discussed in Example 3. The PCR products from the positive assays were then cloned and sequenced to verify their origin and identity.

All sequences generated using the *Dehalococcoides* species-specific primers were found to have identity with *Dehalococcoides ethenogenes* Strain 195 and the sequences generated with primers in Table 1. Sequence identities ranged from 97.5 to 99.7% and were defined as "*Dehalococcoides ethenogenes*-like" sequences since the 16 S rDNA sequences did not completely match the 16S rDNA sequence of Strain 195. As obtained with the primers in Table 1, sequences obtained with primers from Table 3 are unique to the specific site of origin. All 16S rDNA sequences were found to be different from Strain 195 sequence at seven sequence positions (designated by 1A to 1G signature positions, Table 2 in the "Sig. Grp" column). There are three single base substitutions (1A, 1B and 1E), one single-base deletion (1C) and two single-base insertions (1D and 1F). All sequences also shared a nine base deletion located at Strain 195 base number 1085 (Table 2).

Again the same signature sequences were found in regions 2 and 6. They shared the same unique base substitutions that distinguish the 16S rDNA sequences that are found in the DHE V/SFD, the DHE-DII and the DHE-Pin cultures from the Strain 195 16S rDNA sequence as described in Example 3.

The consistency in specific base substitutions among the sequences analyzed in both Examples 3 and 5 suggested that the base positions were signature in nature. To test this premise, the *Dehalococcoides* sequences were phylogenetically analyzed resulting in a 16S rDNA phylogenetic dendrogram or tree. Analysis of the tree data indicated that the specific base substitutions contributed to the formation of three phylogenetic sub-branches in the *Dehalococcoides* branch of the phylogenetic tree. Those rDNA with base substitutions in regions 2 and 6 that are identical to the *D. ethenogenes* Strain 195 sequence formed a phylogenetic sub-branch designated as the "Cornell group". Those rDNA that shared the same base substitutions and are affiliated on the same phylogenetic sub-branch with the DHE-V/SFD sequence or the DHE-pin sequence were designated as members of the "DHE V/SFD group" or the "DHE-Pin group", respectively. Each sequence sub-group was named for the site of origin of the rDNA that was first rDNA sequenced in the group. The Cornell group's name was derived from where Strain 195 was first isolated and described.

volumes were selected for convenience, although it is obvious to one skilled in the art that smaller or larger volumes of groundwater could be used. Upon arrival, the samples were either stored overnight at 4° C. or immediately centrifuged at 9,000×g using a GSA or a G-3 rotor in a RC5B Sorvall Superspeed centrifuge. The resulting cell/soil pellets were resuspended in 2 mL of 1×PBS (10-mM sodium phosphate; 150-mM sodium chloride, pH 7.6) and either stored at −20° C. or immediately extracted for community DNA.

Nucleic acids were extracted from groundwater samples by a bead-mill homogenization procedure, FastDNA™ SPIN Kit for Soil (Q-biogene, Carlsbad, Calif.) and FastPrep

TABLE 3

Dehalococcoides 16S rDNA Primers for a more stringent PCR assay

| | | | |
|---|---|---|---|
| Fp DHE-7 | 5' GGCTCAGGATGAACGCTAGCGGCG 3' | (SEQ ID NO:61) |
| Fp DHE 212 | 5' AGTTGGTGGGGTAATGGCCTACCAAGGCTTC 3' | (SEQ ID NO:62) |
| Rp DHE 247 | 5' CCTCTCAGACCAGCTACCGATCGAAG 3' | (SEQ ID NO:63) |
| Rp DHE 259 | 5' CAGACCAGCTACCGATCGAA 3' | (SEQ ID NO:64) |
| Fp DHE 403 | 5' CACAGGGAAGAATAATGACGGTACCTGT 3' | (SEQ ID NO:65) |
| Rp DHE 429 | 5' CAGGTACCGTCATTATTCTTCCCTGTG 3' | (SEQ ID NO:66) |
| Fp DHE 581 | 5' CTGTTGGACTAGAGTACAGCAGGAGAAAAC 3' | (SEQ ID NO:67) |
| Fp DHE 665 | 5' CGAAGGCGGTTTTCTAGGTT 3' | (SEQ ID NO:68) |
| Fp DHE 669 | 5' GGCGGTTTTCTAGGTTGTC 3' | (SEQ ID NO:69) |
| Rp DHE 705 | 5' GAGCCTCAGTGTCAGTGACAACCTAGAAA 3' | (SEQ ID NO:70) |
| Rp DHE 805 | 5' GTTAGCTTCGGCACAGAGAGGGTCGATACT 3' | (SEQ ID NO:71) |
| FP DHE 1082 | 5' CGAGACTGCCCCGCGAAACG 3' | (SEQ ID NO:72) |
| Rp DHE 1093 | 5' CGGGGCAGTCTCGCTAGAAAAT 3' | (SEQ ID NO:73) |
| Fp DHE 1178 | 5' GGACAGAACAATAGGTTGCAACAGTGTGAACT 3' | (SEQ ID NO:74) |
| Rp DHE 1378 | 5' GCGGTTGGCACATCGACTTCAAGTGTTAC 3' | (SEQ ID NO:75) |

Example 6

Using the *Dehalococcoides ethenogenes*-Like Specific Primers and PCR Assay to Detect Dechlorinating Organisms in Groundwater Samples Soil sample collection and microcosm culture studies are expensive projects and take time to execute. Test samples of groundwater would be easier, less expensive, and more practical to collect if they proved to be useful as a source of *Dehalococcoides* rDNA sequences that could be correlated with site dechlorination activity.

To test if groundwater is useful for testing for *Dehalococcoides*, ten groundwater samples were collected from widely diverse chloroethene-contaminated sites. Those sites, exhibiting full dechlorination of chloroethenes, were shown to have the dechlorination daughter products, VC and ethene. Stewards provided chemical analysis verification of site dechlorination.

Community DNA extracted from groundwater samples was tested for *Dehalococcoides* 16S rDNA sequences. Plastic sampling bottles filled to the top with 250 to 1000 milliliters of groundwater from monitoring wells were double bagged and shipped to the lab on ice. These particular FP120 (Savant/Bio 101 Holbrook, N.Y.), that was designed to isolate genomic DNA from all cell types. Other DNA isolation kits or procedures that produce DNA having sufficient quality as required for this assay may also be used. The groundwater community DNA was isolated from resuspended cell/debris pellets in 1×PBS (1 mL), using the silica matrix system of FastDNA™ SPIN Kit and following the manufacturer's protocol and recommendations. The community DNA was eluted by adding 80 μL of sterile, deionized water, then mixing the matrix and the water together with a pipette tip, and centrifuging for 1 min at 14,000×g. The flow through product was transferred to a screw capped 1.5 mL tube and stored at −20° C. until it was needed for the PCR assay.

The samples were tested in the PCR assay (Examples 3 and 5) using primer sets selected from Tables 1 and 3. Groundwater samples from ten sites yielded the anticipated amplification products of the correct size in the DHE PCR assay. Following PCR, the identities of the amplified products were verified by sequencing. The rDNA sequences found in the ten groundwater sites ranged from 97.7% to 99.7% in identity with Strain 195 and the microcosm *Dehalococcoides* 16S rDNA sequences of this application.

The *Dehalococcoides* PCR assay results from groundwater testing were similar to assay results from the dechlorinating microcosm testing (data not shown). *Dehalococcoides* rDNA sequences were detected only in samples that were linked to full dechlorination of chloroethenes. Linking the detection of *Dehalococcoides* 16S rDNA sequences to full dechlorination of chloroethenes supported by documentation provides a key indicator for the existence of favorable dechlorination conditions that support growth and maintenance of dehalorespiring/dechlorinating bacteria.

Example 7

Using the *Dehalococcoides ethenogenes*-Like Specific Primers and PCR Assay to Detect Dechlorinating Organisms in Soil or Sediment Samples Two procedures were used to obtain soil samples from test sites. Some soil core samples were obtained by split spoon sampling at depths ranging from 3 to 25 m, depending on the depth of the aquifer to be tested. The cores were shipped on ice in stainless steel cylinders or in sterile glass jars to the laboratory. Other soil core samples were obtained using a Geoprobe system (Geoprobe Systems, Salina, Kans.). A coring tube was pounded to depths of 3 to 15 m and retrieved. A sterile acrylic sleeve was then placed in the tube. It was reinserted into the ground and driven an additional 0.7 m. The acrylic sleeve was then removed, capped, sealed with duct tape, and stored on ice for transport to the laboratory. Sediments were collected with a drill rig or hand auger, placed in mason jars, and shipped to the lab on ice. Upon arrival, all samples were stored in an anaerobic glove bag (chamber) (Coy Laboratory Products Inc., Ann Arbor, Mich.), whose atmosphere was 5% $H_2$, 10% $CO_2$ and 85% $N_2$.

Community DNAs extracted from soil and sediment samples were tested for *Dehalococcoides* 16S rDNA sequences. Nucleic acids were extracted from 5 to 10 g of each soil or sediment sample using kits designed to isolate DNA from all types of cells in soil samples. These kits included the FastDNA Spin Kit for Soil (Bio 101, Vista, Calif., used as described in Example 3) and a bead homogenization procedure from Mo Bio (Solana Beach, Calif.). Using the Mo Bio Kit, the community DNA from the soil and sediment samples was eluted from the center of a spin filter, following procedures recommended by the manufacturer. The final volume was 8 mL, to which 0.32 mL of 5M NaCl was added and mixed. Then 16.6 mL of 100% cold ethanol was add to the samples and mixed. The samples were then centrifuged at 9,000×g for 15 min, the supernatant was decanted, and the pellets were dried in either a desiccator or ambient air. The dried DNA pellets were dissolved in 1 mL of water.

Each sample was tested in the PCR assay (Examples 3 and 5) using primer sets selected from the primers in Table 1 and 3. Soil and sediment samples yielded the anticipated amplification products of the correct size in the *Dehalococcoides* PCR assay. Following PCR, the identities of the amplified products were verified by sequencing. The rDNA sequences ranged from 97.7% to 99.7% in identity with Strain 195 and the microcosm *Dehalococcoides* 16S rDNA sequences of this application.

The *Dehalococcoides* PCR assay results from soil testing and sediments were similar to assay results from the dechlorinating microcosm testing. *Dehalococcoides* rDNA sequences were detected only in samples that were linked to full dechlorination of chloroethenes. Linking the detection of *Dehalococcoides* 16S rDNA sequences to full dechlorination of chloroethenes supported by documentation provides a key indicator for the existence of favorable dechlorination conditions that support growth and maintenance of dehalorespiring/dechlorinating bacteria.

Example 8

Differentiation and Identification of *Dehalococcoides* Sequences Using DGGE Based on Differences in Signature Sequences in Variable Regions 2 and 6

This Example explores the utility of DGGE as a technique for the separation of DHE sub-families. Variable sequence regions 2 and 6 of the DHE 16s rDNA molecule are particularly well suited for this type of analysis, as PCR fragments containing each of these regions are identical in size, but variable in sequence.

To apply DGGE in the instant application specialized GC "clamps" are used for fragment segregation. This clamp sequence modification, consisting of a sequence of approximately 40 G and C nucleotides, is incorporated at the 5' end of one of the PCR primers. This modification effectively modifies the melting behavior of the PCR fragment of interest to the extent that 100% of all sequence variations can be detected (Myer et al., *Nucleic Acids Res.* 13:399 (1985); Sheffield et al., *Proc. Natl. Acad. Sci. USA* 86:2742 (1989)). Complete strand separation of both strands can be retarded and even prevented by the incorporation of the GC "clamp" creating an artificially high melting domain at one end of the molecule during PCR amplification of the fragment. The use of the clamp is a powerful tool useful for separating DNA fragments that are the same size, when studying the diversity in the sequence of a particular gene in a given population or gene pool.

Denaturing gel methods have been used to analyze 16S rRNA genes from environmental samples and allow the separation of PCR-amplified genes on polyacrylamide gels to give a profile that is an indication of the composition and diversity of the microbial community (Muyzer et al., *Appl. Environ. Microbiol.* 59:695 (1993)). This method can be applied to detect and separate multiple *Dehalococcoides* members in a population or at least separate the different sequence signature groups as defined by region 2 and 6 (FIGS. 5A and B).

For practice in this particular application, one primer used in the PCR reaction will have a GC clamp sequence at its 5' end. SEQ ID NO: 76 is an example of such a sequence that can be used in the design of the 5' clamp sequence (Sheffield et al., *Proc. Natl. Acad. Sci. USA* 86:2742 (1989)).

5' CGCCCGCCGCGCCCCGCGCCCGTCCCGC-CGCCCCGCCCGCC 3' (SEQ ID NO: 76)

It is important to note that this GC clamp sequence can be incorporated at the 5' end of either the forward or reverse primer, for any given primer pair.

One example of a primer set that can be used to distinguish the Cornell group (strain 195), the DHE V/SFD group, and the DHE-pin group sequences, based on differences in signature bases in variable region 2, are:

```
Fp DG DHE 1 5'CGCCCGCCGCGCCCCGCGCCCGTCCCGCCGCC     (SEQ ID NO:77)
CCCGCCCGCC GATGAACGCTAGCGGCG 3'
``` and

```
Rp DHE 259 5'CAGACCAGCTACCGATCGAA3'                (SEQ ID NO:64)
```

The resulting product separates into at least three separate bands representing each of the sequence groups, e.g., Cornell, DHE V/SFD, and DHE-pin. Other signature bases present in the resulting PCR product that define a different sequence or sequences within the same sequence group will allow for additional separation of those molecules as well.

An example of primers that can be used to separate the DHE-pin group from the Cornell and the DHE V/SFD sequence groups, by targeting the differences in signature bases in variable region 6, are:

```
Fp DG DHE 665                                      (SEQ ID NO:78)
5' CGCCCGCCGCGCCCCGCGCCCGTCCCGCCGCCCCCGCCCGCCCGAAGG
CGGTTTTCTAGGTT 3'
``` and

```
Rp DHE 1093                                        (SEQ ID NO:73)
5' CGGGGCAGTCTCGCTAGAAAAT 3'
```

Again the GC clamp sequence can be on either primer. Nonetheless, the resulting product is at least two separate bands, one representing the DHE-pin sequence group and the other product representing the Cornell and DHE V/SFD sequence groups. Again as in region 2, signature bases in the resulting PCR product, which can define a different sequence or sequences within the same sequence group, will allow for separation of those fragments as well.

The 16S rRNA genes are amplified from community DNA isolated from microcosm DNA using a Perkin-Elmer 9600 thermocycler. Of course, soil or groundwater samples would also be appropriate. The PCR reactions are performed using Taq polymerase (Perkin-Elmer, Norwalk, Conn.) and using the following conditions: 95° C., 2 min initial denaturation followed by 40 cycles at 94° C. for 30 s, 57° C. for 45 s, and 72° C. for 1 min followed by an extension at 72° C. for 7 min. DGGE electrophoresis of *Dehalococcoides*-like PCR amplified 16S rDNA fragments is performed using the Bio-Rad D-gene system (Bio-Rad, Hercules, Calif.). The PCR amplified samples are loaded on a 35–60% denaturing gradient 8% acrylamide gel and run at 200 V for 300 min at 60° C. with 1×TAE buffer. The gels are then stained with ethidium bromide to visualize the DNA fragments. The gel image is digitized using a Kodak DS Image Station 440 system (NEN Life Sciences, Inc, Boston, Mass.), cropped, labeled, and the contrast adjusted with NIH Image 1.62 and Canvas 7 (Deneba Software, Miami, Fla.).

Example 9

Using Species-Specific 16S rRNA Primers for the Detection of Other Known Dechlorinating Bacteria The detection and sequencing of other dechlorinating organisms was accomplished by designing a third set of unique PCR primers (Table 4). The target organisms were *Dehalobacter restrictus, Dehalospirillum multivorans, Desulfitobacterium dehalogens,* and *Desulfuromonas chloroethenica,* which have all been shown to partially dechlorinate chlorinated ethenes by dehalorespiration (Kochian et al., *Plant Mol. Biol.* 46:237 (1995); Delhaize et al., *Plant Physiol.* 107:315 (1995); Gerritse et al. *Arch. Microbiol.* 165:132 (1996); Damborsky, *Folia Microbiol. (Praha)* 44:247 (1999)).

The PCR primers were designed using variable sequence regions. To determine the location of these variable sequences, dechlorinating 16S rRNA sequences were aligned using MegAlign (DNAstar, Madison, Wis.) or Pileup (Genetics Computer Group, Madison, Wis.) with the same 16S rRNA sequences from 100 organisms used in Example 2 to select the *Dehalococcoides*-specific primers. Specific dechlorinating 16s rRNA sequences used were GenBank NO's. AF218076, U84497, L28946, and U49748 and two sequences closely related to *Dehalococcoides* (identified as *Dehalococcoides* Family A organisms: DHE-DHFA (SEQ ID NO:94) and DHE-FAOK (SEQ ID NO:95)). Primer candidate sequences specific for the 16S rRNA gene from each dechlorinating bacterium were manually picked using the same procedure as outlined in Example 2. Their uniqueness was determined using the "on-line" Probe Match Program from the Ribosomal Database Project II (RDPII, Michigan State University, East Lansing, Mich.) or by comparing the sequences to the GenBank database using Blast. Both analyses returned an overview of the matches between the putative primer sequence and potential target sequences. The program results showed the sequences that match the query sequence and also showed sequences that had mismatches, deletions and insertions, citing the number and positions of the aberrations.

The sequences that were unique and passed this test as signature sequences were then designed as either a forward or reverse primer, usually dependent on their position in the sequence. The most unique sequence of the signature sequence was designed into the 3' end in either type of primer for increased specificity. The selected species-specific primers are shown in Table 4, corresponding to *Dehalobacter restrictus, Dehalospirillum multivorans, Desulfitobacterium dehalogenans, Desulfuromonas chloroethnica* and *Dehalococcoides* Family A Group.

The primers were synthesized using standard cyanoethyl phosphoramidite coupling chemistry on controlled pore glass (CPG) supports on automated DNA oligonucleotide synthesizer (Applied Biosystems Model 392, Perkin-Elmer, Foster City, Calif.).

The primers were tested after they were synthesized using PCR on samples taken from microcosms known to have dechlorinating bacteria. The PCR products were sized on agarose electrophoresis and then cloned and sequenced to verify that the identity of the amplified sequences was the targeted dechlorinating bacteria 16S rRNA sequence.

TABLE 4

Primers for Other Dehalorespirating Bacteria

*Dehalobacter restrictus*
Fp DeR 4215' AGGGAAGAACGGCATCTGTGT 3' (SEQ ID NO:79)

Rp DeR 9985' CATATCTCTACGGGATTAGTT 3' (SEQ ID NO:80)

*Dehalospirillum multivorans*
Rp DHSPM 1210 5' GTATCGCGTCTCTTTGTCCTA 3' (SEQ ID NO:81)

Fp DHSPM 576 5' GCTCTCGAAACTGGTTACCTA 3' (SEQ ID NO:82)

*Desulfitobacterium dehalogenans*
Fp DFD 1022 5' AGAATCCCGTGGAAACATGG 3' (SEQ ID NO:83)

Fp DFD 6475' GGACTGCATCGGAAACTGGT 3' (SEQ ID NO:84)

Rp DFD 1041 5' CCATGTTTCCACGGGATTC 3' (SEQ ID NO:85)

Rp DFD 1308 5' TCGGATTTGCTCCACCTCA 3' (SEQ ID NO:86)

*Desulfuromonas chloroethnica*
Fp DSM 1265' GGGATAACACTTCGAAAGGGGTG 3' (SEQ ID NO:87)

Rp DSM 4885' GGTACCGTCAGGCCCAAGTGTT 3' (SEQ ID NO:88)

Dehalococcoides Family A Group
Fp Dhc AO 95 5' TAACCTGCCTTTAAGTGGGG-GATAACA 3' (SEQ ID NO:89)

Rp Dhc AO 278 5' TCCTCTCAGACCAGCTAC-CGATCA TC 3' (SEQ ID NO:90)

Fp Dhc AO 581 5' GTCATCCGATACTGTTGGACTTG 3' (SEQ ID NO:91)

Rp Dhc AO 1213 5' GCTCCCGGTCACCCGGTG 3' (SEQ ID NO:92)

Rp Dhc AO 603 5' AAGTCCAACAGTATCGGAT-GACCC 3' (SEQ ID NO:93)

Example 10

Detection of Dechlorinating Bacteria by Targeting Community rRNA Instead of Community DNA In examples 2 through 9 community DNA was isolated to detect the target gene (i.e., the 16S rRNA gene, known as the 16S rDNA) from dechlorinating bacteria in the community population. The approach in those examples targets at least one gene per chromosome with some bacteria possessing up to ten copies of rRNA on their chromosome.

Bacteria, on average, have been shown to have 1,000 to 10,000 ribosomes per cell. Each ribosome is made up of a 30S subunit and a 50S subunit. The 16S rRNA is a component of the 30S subunit. Therefore each cell has the potential to have between 1,000 to 10,000 copies of the 16S rRNA. The assays described in this application could be more sensitive if they were targeted for the rRNA itself, instead of the rRNA gene. By targeting the rRNA, assay sensitivity for detection of dechlorinating bacteria cells can be potentially increased by factors of $10^3$ to $10^4$.

Total cellular RNA can be isolated from the bacteria by using commercial kits. One example is the Qiagen RNeasy Kit (Valencia, Calif.), which contains all of the necessary reagents and binding columns to isolate RNA from $10^{10}$ cells. According to the manufacturer, a DNase digestion is not required since the RNeasy silica-membrane is efficient in the removal of most of the DNA without DNase treatment. The sample RNA is in a final volume of 150 μL (1–5 μg/μL).

The target rRNA sequences can be amplified using an RT-PCR procedure, where one strand is copied from the rRNA template using the reverse primer and reverse transcriptase ('RT', an RNA-directed DNA polymerase) to make one strand of a DNA target sequence. In turn, the ssDNA RT product is amplified by PCR. This two step procedure can be accomplished in one tube, adding all reagents to the reaction mixture prior to starting the RT reaction. The necessary reagents are added in a buffer that will support both polymerases. The PCR Taq I DNA polymerase is inhibited while the RT DNA PCR template is being synthesized. This is accomplished by use of a "hot start" Taq I DNA polymerase. The "hot start" Taq I DNA polymerase is a precomplexed mixture of the Taq I DNA polymerase and an anti-Taq I DNA polymerase (monoclonal antibody). The antibody forms complexes with Taq DNA polymerase, thereby inactivating the polymerase and preventing its interaction with the primers during the RT Reaction and the newly formed templates before the PCR cycling starts. The Taq DNA polymerase becomes active by denaturing the anti-Taq antibody by incubating the complex at 95° C. for 5 to 10 min. The polymerase is then active and can amplify the newly RT-generated templates.

The PCR reactions contain 1×PCR Buffer (10 mM Tris-HCl, pH 8.3; 50 mM KCl), 1.5 mM $MgCl_2$, 10 µM of each deoxynucleoside triphosphate, 20 pmol of each primer (a forward primer and a reverse primer from Tables 1, 3 or 4), 2.5 U of the hot start Gold® Taq polymerase (Applied Biosystems, Norwich, Conn.), 5.0 units of AMV RT polymerase (Promega, Madison, Wis.) and 1 µL of the community RNA. The samples are heated to 65° C. and incubated for 30 min to synthesize the DNA copy of the rRNA with AMV RT. The samples are then heated to 95° C. for 15 min to activate the Taq I Polymerase. The PCR is performed using 40 cycles at 94° C. for 1 min, 55° C. for 1 min and 72° C. for 1 min. The PCR is followed by incubating the reaction at 72° C. for 7 min to complete strand extension on the products. The assay products are cooled to 4° C. An aliquot of the final PCR reaction can be visualized on a 2% agarose gel (SeaKem GTG, FMC BioProducts, Rockland, Me.) in 1×TBE buffer at 50 volts for 30 min and stained with ethidium bromide (0.5 µg/mL). Analysis of the gel can be performed as described in Example 3, 4 and 5.

What is claimed is:

1. An isolated 16S rDNA sequence indicative of a dechlorinating bacterial organism as set forth in SEQ ID NO:94 or an isolated nucleic acid molecule that is completely complementary to the isolated 16S rDNA sequence as set forth in SEQ ID NO:94.

* * * * *

SEQUENCE LISTING

<160> NUMBER OF SEQ ID NOS: 103

<210> SEQ ID NO 1
<211> LENGTH: 24
<212> TYPE: DNA
<213> ORGANISM: Dehalococcoides ethenogenes

<400> SEQUENCE: 1
attttctagc gagactgccc cgcg                                        24

<210> SEQ ID NO 2
<211> LENGTH: 1377
<212> TYPE: DNA
<213> ORGANISM: Dehalococcoides ethenogenes strain PL

<400> SEQUENCE: 2
gatgaacgct agcggcgtgc cttatgcatg caagtcgaac ggtcttaagc aattaagata      60
gtggcaaacg ggtgagtaac gcgtaagtaa cctacctcta agtgggggat agcttcggga     120
aactgaaggt aataccgcat gtgatgggct gacataagtc ggttcattaa agccgcaagg     180
tgcttggtga ggggcttgcg tccgattagc tagttggtgg ggtaatggcc taccaaggct     240
tcgatcggta gctggtctga gaggatgatc agccacactg ggactgagac acggcccaga     300
ctcctacggg aggcagcagc aaggaatctt gggcaatggg cgaaagcctg acccagcaac     360
gccgcgtgag ggatgaaggc tttcgggttg taaacctctt tcacaggga agaataatga     420 cggtacctgt ggaataagct tcggctaact acgtgccagc agccgcggta atacgtagga     480
agcaagcgtt atccggattt attgggcgta aagtgagcgt aggtggtctt tcaagttgga     540
tgtgaaattt cccggcttaa ccgggacgtg tcattcaata ctgttggact agagtacagc     600
aggagaaaac ggaattcccg gtgtagtggt aaaatgcgta gatatcggga ggaacaccag     660
aggcgaaggc ggttttctag gttgtcactg acactgaggc tcgaaagcgt ggggagcgaa     720
cagaattaga tactctggta gtccacgcct taaactatgg acactaggta tagggagtat     780
cgaccctctc tgtgccgaag ctaacgctyt aagtgtcccg cctggggagt acggtcgcaa     840
ggctaaaact caaaggaatt gacggggggcc cttacaagca gcggagcgtg tggtttaatt     900
cgatgctaca cgaagaacct taccaagatt tgacatgcat gaagtagtga accgaaaggg     960
aaacgacctg ttaagtcagg agtttgcaca ggtgctgcat ggctgtcgtc agctcgtgcc    1020
gtgaggtgtt tggttaagtc ctgcaacgag cgcaacccctt gttgctagtt aaattttcta    1080
gcgagactgc cccgcgaaac ggggaggaag gtggggatga cgtcaagtca gcatggcctt    1140
tatatcttgg gctacacaca cgctacaatg gacagaacaa taggttgcaa cagtgtgaac    1200
tggagctaat ccccaaagct gtcctcagtt cggattgcag gctgaaaccc gcctgcatga    1260
agttggagtt gctagtaacc gcatatcagc aaggtgcggt gaatacgttc tcgggccttg    1320
tacacaccgc ccgtcacgtc atgaaagccg gtaacacttg aagtcgatgt gccaacc    1377

<210> SEQ ID NO 3
<211> LENGTH: 1378
<212> TYPE: DNA
<213> ORGANISM: Dehalococcoides ethenogenes strain V/SFD

<400> SEQUENCE: 3
gatgaacgct agcggcgtgc cttatgcatg caagtcgaac ggtcttaagc aattaagata      60
gtggcaaacg ggtgagtaac gcgtaagtaa cctacctcta agtgggggat agcttcggga     120
aactgaaggt aataccgcat gtggtgggcc gacataagtt ggttcactaa agccgtaagg     180
tgcttggtga ggggcttgcg tccgattagc tagttggtgg ggtaacggcc taccaaggct     240
tcgatcggta gcttggtctg agaggatgat cagccacact gggactgaga cacggcccag     300
actcctacgg gaggcagcag caaggaatct tgggcaatgg gcgaaagcct gacccagcaa     360
cgccgcgtga gggatgaagg ctctcgggtt gtaaacctct tttcacaggg aagaataatg     420
acggtacctg tggaataagc ttcggctaac tacgtgccag cagccgcggt aatacgtagg     480
aagcaagcgt tatccggatt tattgggcgt aaagtgagcg taggtggtct ttcaagttgg     540
atgtgaaatt tcccggctta accgggacgt gtcattcaat actgttggac tagagtacag     600
caggagaaaa cggaattccc ggtgtagtgg taaaatgcgt agatatcggg aggaacacca     660
gaggcgaagg cggttttcta ggttgtcact gacactgagg ctcgaaagcg tgggagcga     720
acagaattag atactctggt agtccacgcc ttaaactatg gacactaagt atagggagta     780
tcgaccctct ctgtgccgaa gctaacgctt aagtgtccc gcctggggag tacggtcgca     840
aggctaaaac tcaaaggaat tgacgggggc ccgcacaagc agcggagcgt gtggtttaat     900
tcgatgctac acgaagaacc ttaccaagat ttgacatgca tgaagtagtg aaccgaaagg     960
gaaacgacct gttaagtcag gagtttgcac aggtgctgca tggctgtcgt cagctcgtgc    1020
cgtgaggtgt ttggttaagt cctgcaacga gcgcaaccct tgttgctagt taaattttct    1080
agcgagactg ccccgcgaaa cggggaggaa ggtggggatg acgtcaagtc agcatggcct    1140
ttatatcttg ggctacacac acgctacaat ggacagaaca ataggttgca acagtgtgaa    1200
ctggagctaa tcctcaaagc tgtcctcagt tcggattgca ggctgaaacc cgcctgcatg    1260
aagttggagt tgctagtaac cgcatatcag caaggtgcgg tgaatacgtt ctcgggcctt    1320
gtacaccgc ccgtcacgt catgaaagcc ggtaacactt gaagtcgatg tgccaacc       1378

<210> SEQ ID NO 4
<211> LENGTH: 1377
<212> TYPE: DNA
<213> ORGANISM: Dehalococcoides ethenogenes strain DAB

<400> SEQUENCE: 4
gatgaacgct agcggcgtgc cttatgcatg caagtcgaac ggtcttaagc aattaagata      60
gtggcgaacg ggtgagtaac gcgtaagtaa cctacctcta agtgggggat agcttcggga     120
aactgaaggt aataccgcat gtggtgggcc gacatatgtt ggttcactaa agccgtaagg     180
cgcttggtga ggggcttgcg tccgattagc tagttggtgg ggtaatggcc taccaaggct     240
tcgatcggta gcttggtctg aggatgatc agccacactg gactgagac acggcccaga     300
ctcctacggg aggcagcagc aaggaatctt gggcaatggg cgaaagcctg acccagcaac     360
gccgcgtgag ggatgaaggc tttcgggttg taaacctctt tcatagggga agaataatga     420

-continued

```
cggtacctgt ggaataagct tcggctaact acgtgccagc agccgcggta atacgtagga      480
agcaagcgtt atccggattt attgggcgta aagtgagcgt aggtggtctt tcaagttgga      540
tgtgaaattt cccggcttaa ccgggacgag tcattcaata ctgttggact agagtacagc      600
aggagaaaac ggaattcccg gtgtagtggt aaaatgcgta gatatcggga ggaacaccag      660
aggcgaaggc ggttttctag gttgtcactg acactgaggc tcgaaagcgt ggggagcgaa      720
cagaattaga tactctggta gtccacgcct taaactatgg acactaggta tagggagtat      780
cgaccctctc tgtgccgaag ctaacgcttt aagtgtcccg cctggggagt acggtcgcaa      840
ggctaaaact caaaggaatt gacggggggcc cgcacaagca gcggagcgtg tggtttaatt      900
cgatgctaca cgaagaacct taccaagatt tgacatgcat gtagtagtga actgaaaggg      960
gaacgacctg ttaagtcagg aacttgcaca ggtgctgcat ggctgtcgtc agctcgtgcc     1020
gtgaggtgtt tggttaagtc ctgcaacgag cgcaacccct tgttgctagtt aaattttcta     1080
gcgagactgc cccgcgaaac ggggaggaag gtggggatga cgtcaagtca gcatggcctt     1140
tatatcttgg gctacacaca cgctacaatg gacagaacaa taggttgcaa cagtgtgaac     1200
tggagctaat ccccaaagct gtcctcagtt cggattgcag gctgaaaccc gcctgcatga     1260
agttggagtt gctagtaacc gcatatcagc atggtgcggt gaatacgttc tcgggccttg     1320
tacacaccgc ccgtcacgtc atgaaagccg gtaacacttg aagtcgatgt gccaacc       1377
```

<210> SEQ ID NO 5
<211> LENGTH: 1377
<212> TYPE: DNA
<213> ORGANISM: Dehalococcoides ethenogenes strain PIN

<400> SEQUENCE: 5

```
gatgaacgct agcggcgtgc cttatgcatg caagtcgaac ggtcttaagc aattaagata       60
gtggcgaacg ggtgagtaac gcgtaagtaa cctacctcta agtgggggat agcttcggga      120
aactgaaggt aataccgcat gtggtgggcc gacatatgtt ggttcactaa agccgtaagg      180
cgcttggtga ggggcttgcg tccgattagc tagttggtgg ggtaatggcc taccaaggct      240
tcgatcggta gctggtctga gaggatgatc agccacactg gactgagaca cggcccaga      300
ctcctacggg aggcagcagc aaggaatctt gggcaatggg cgaaagcctg acccagcaac      360
gccgcgtgag ggatgaaggc tttcggggttg taaacctctt ttcataggga agaataatga      420
cggtacctgt ggaataagct tcggctaact acgtgccagc agccgcggta atacgtagga      480
agcaagcgtt atccggattt attgggcgta aagtgagcgt aggtggtctt tcaagttgga      540
tgtgaaattt cccggcttaa ccgggacgag tcattcaata ctgttggact agagtacagc      600
aggagaaaac ggaattcccg gtgtagtggt aaaatgcgta gatatcggga ggaacaccag      660
aggcgaaggc ggttttctag gttgtcactg acactgaggc tcgaaagcgt ggggagcgaa      720
cagaattaga tactctggta gtccacgcct taaactatgg acactaggta tagggagtat      780
cgaccctctc tgtgccgaag ctaacgcttt aagtgtcccg cctggggagt acggtcgcaa      840
ggctaaaact caaaggaatt gacggggggcc cgcacaagca gcggagcgtg tggtttaatt      900
cgatgctaca cgaagaacct taccaagatt tgacatgcat gtagtagtga actgaaaggg      960
gaacgacctg ttaagtcagg aacttgcaca ggtgctgcat ggctgtcgtc agctcgtgcc     1020
gtgaggtgtt tggttaagtc ctgcaacgag cgcaacccct tgttgctagtt aaattttcta     1080
gcgagactgc cccgcgaaac ggggaggaag gtggggatga cgtcaagtca gcatggcctt     1140
tatatcttgg gctacacaca cgctacaatg gacagaacaa taggttgcaa cagtgtgaac     1200
```

```
tggagctaat ccccaaagct gtcctcagtt cggattgcag gctgaaaccc gcctgcatga   1260
agttggagtt gctagtaacc gcatatcagc atggtgcggt gaatacgttc tcgggccttg   1320
tacacaccgc ccgtcacgtc atgaaagccg gtaacacttg aagtcgatgt gccaacc      1377
```

<210> SEQ ID NO 6
<211> LENGTH: 1377
<212> TYPE: DNA
<213> ORGANISM: Dehalococcoides ethenogenes strain DLL

<400> SEQUENCE: 6

```
gatgaacgct agcggcgtgc cttatgcatg caagtcgaac ggtcttaagc aattaagata   60
gtggcaaacg ggtgagtaac gcgtaagtaa cctacctcta agtgggggat agcttcggga   120
aactgaaggt aataccgcat gtggtgggcc gacataagtt ggttcactaa agccgtaagg   180
tgcttggtga ggggcttgcg tccgattagc tagttggtgg ggtaacggcc taccaaggct   240
tcgatcggta gctggtctga gaggatgatc agccacactg ggactgagac acggcccaga   300
ctcctacggg aggcagcagc aaggaatctt gggcaatggg cgaaagcctg acccagcaac   360
gccgcgtgag ggatgaaggc tctcggttg taaacctctt ttcacaggga agaataatga    420
cggtacctgt ggaataagct tcggctaact acgtgccagc agccgcggta atacgtagga   480
agcaagcgtt atccggattt attgggcgta aagtgagcgt aggtggtctt tcaagttgga   540
tgtgaaattt cccggcttaa ccgggacgtg tcattcaata ctgttggact agagtacagc   600
aggagaaaac ggaattcccg gtgtagtggt aaaatgcgta gatatcggga ggaacaccag   660
aggcgaaggc ggttttctag gttgtcactg acactgaggc tcgaaagcgt ggggagcgaa   720
cagaattaga tactctggta gtccacgcct taaactatgg acactaggta tagggagtat   780
cgaccctctc tgtgccgaag ctaacgcttt aagtgtcccg cctggggagt acggtcgcaa   840
ggctaaaact caaaggaatt gacgggggcc cgcacaagca gcggagcgtg tggtttaatt   900
cgatgctaca cgaagaacct accaagatt tgacatgcat gaagtagtga accgaaaggg    960
aaacgacctt ttaagtcagg agtttgcaca ggtgctgcat ggctgtcgtc agctcgtgcc   1020
gtgaggtgtt tggttaagtc ctgcaacgag cgcaacccctt gttgctagtt aaatttctta   1080
gcgagactgc cccgcgaaac ggggaggaag gtggggatga cgtcaagtca gcatggcctt   1140
tatatcttgg gctacacaca cgctacaatg gacagaacaa taggttgcaa cagtgtgaac   1200
tggagctaat cctcaaagct gtcctcagtt cggattgcag gctgaaaccc gcctgcatga   1260
agttggagtt gctagtaacc gcatatcagc aaggtgcggt gaatacgttc tcgggccttg   1320
tacacaccgc ccgtcacgtc atgaaagccg gtaacacttg aagtcgatgt gccaacc      1377
```

<210> SEQ ID NO 7
<211> LENGTH: 1443
<212> TYPE: DNA
<213> ORGANISM: Dehalococcoides ethenogenes strain 195
<220> FEATURE:
<221> NAME/KEY: misc_feature
<222> LOCATION: (1353)..(1353)
<223> OTHER INFORMATION: N= unknown

<400> SEQUENCE: 7

```
gatgaacgct agcggcgtgc cttatgcatg caagtcgaac ggtcttaagc aattaagata   60
gtggcaaacg ggtgagtaac gcgtaagtaa cctacctcta agtgggggat agcttcggga   120
aactgaaggt aataccgcat gtgatgggct gacataagtc ggttcattaa agccgcaagg   180
```

```
tgcttggtga ggggcttgcg tccgattagc tagttggtgg ggtaatggtc taccaaggct      240
tcgatcggta gctggtctga gaggatgatc agccacactg ggactgagac acgggccaga      300
ctcctacggg aggcagcagc aaggaatctt gggcaatggg cgaaagcctg acccagcaac      360
gccgcgtgag ggatgaaggc tttcggtttg taaacctctt ttcacaggga agaataatga      420
cggtacctgt ggaataagct tcggctaact acgtgccagc agccgcggta atacgtaggg      480
aagcaagcgt tatccggatt tattgggcgt aaagtgagcg taggtggtct ttcaagttgg      540
atgtgaaatt tcccggctta accgggacgt gtcattcaat actgttggac tagagtacag      600
caggagaaaa cggaattccc ggtgtagtgg taaaatgcgt agatatcggg aggaacacca      660
gaggcgaagg cggttttcta ggttgtcact gacactgagg ctcgaaagcg tggggagcga      720
acagaattag atactctggt agtccacgcc ttaaactatg gacactaggt atagggagta      780
tcgaccctct ctgtgccgaa gctaacgctt taagtgtccc gcctggggag tacggtcgca      840
aggctaaaac tcaaaggaat tgacggggc ccgcacaagc agcggagcgt gtggtttaat      900
tcgatgctac acgaagaact taccaagatt tgacatgcat gaagtagtga accgaaaggg      960
aaacgacctg ttaagtcagg agtttgcaca ggtgctgcat ggctgtcgtc agctcgtgcc     1020
gtgaggtgtt gggttaagtc ctgcaacgag cgcaaccttg ttgctagtta aattttctag     1080
cgagactagc gagactgccc cgcgaaacgg ggaggaaggt ggggatgacg tcaagtcagc     1140 atggcccttta tatcttgggc tacacacacg ctacaatgga cagaacaata ggttgcaaca     1200
gtgtgaactg gagctaatcc ccaaagctgt cctcagttcg gattgcaggc tgaaacccgc     1260
ctgcatgaag ttggagttgc tagtaaccgc atatcagcaa ggtgcggtga atacgttctc     1320
gggccttgta cacaccgccc gtcacgtcat ganagccggt aacacttgaa gtcgatgtgc     1380
caaccgcaag gaggcagtcg ccgagggtgg gactggtaat tgggacgaag tcgtaacaag     1440
gta                                                                  1443
```

<210> SEQ ID NO 8
<211> LENGTH: 47
<212> TYPE: DNA
<213> ORGANISM: Dehalococcoides ethenogenes

<400> SEQUENCE: 8

```
tgtgrtgggc ygacatawgt yggttcayta aagccgyaag gygcttg                    47
```

<210> SEQ ID NO 9
<211> LENGTH: 20
<212> TYPE: DNA
<213> ORGANISM: Dehalococcoides ethenogenes

<400> SEQUENCE: 9

```
aagtcgaacg gtcttaagca                                                  20
```

<210> SEQ ID NO 10
<211> LENGTH: 20
<212> TYPE: DNA
<213> ORGANISM: Dehalococcoides ethenogenes

<400> SEQUENCE: 10

```
cgtcattatt cttccctgtg                                                  20
```

<210> SEQ ID NO 11
<211> LENGTH: 21
<212> TYPE: DNA
<213> ORGANISM: Dehalococcoides ethenogenes -continued

```
<400> SEQUENCE: 11
gggaaacgac ctgttaagtc a                                         21

<210> SEQ ID NO 12
<211> LENGTH: 22
<212> TYPE: DNA
<213> ORGANISM: Dehalococcoides ethenogenes

<400> SEQUENCE: 12
ggattagctc cagttcacac tg                                        22

<210> SEQ ID NO 13
<211> LENGTH: 20
<212> TYPE: DNA
<213> ORGANISM: Dehalococcoides ethenogenes

<400> SEQUENCE: 13
aaatttaact agcaacaagg                                           20

<210> SEQ ID NO 14
<211> LENGTH: 19
<212> TYPE: DNA
<213> ORGANISM: Dehalococcoides ethenogenes

<400> SEQUENCE: 14
ggagtatcga ccctctctg                                            19

<210> SEQ ID NO 15
<211> LENGTH: 18
<212> TYPE: DNA
<213> ORGANISM: Dehalococcoides ethenogenes

<400> SEQUENCE: 15
gggagtatcg accctctc                                             18

<210> SEQ ID NO 16
<211> LENGTH: 18
<212> TYPE: DNA
<213> ORGANISM: Dehalococcoides ethenogenes

<400> SEQUENCE: 16
agtgaaccga aagggaaa                                             18

<210> SEQ ID NO 17
<211> LENGTH: 21
<212> TYPE: DNA
<213> ORGANISM: Dehalococcoides ethenogenes

<400> SEQUENCE: 17
gggttgtaaa cctcttttca c                                         21

<210> SEQ ID NO 18
<211> LENGTH: 20
<212> TYPE: DNA
<213> ORGANISM: Dehalococcoides ethenogenes

<400> SEQUENCE: 18
gttagcttcg gcacagagag                                           20

<210> SEQ ID NO 19
<211> LENGTH: 20
<212> TYPE: DNA
```

<213> ORGANISM: Dehalococcoides ethenogenes

<400> SEQUENCE: 19
tcagtgacaa cctagaaaac                                              20

<210> SEQ ID NO 20
<211> LENGTH: 17
<212> TYPE: DNA
<213> ORGANISM: Dehalococcoides ethenogenes

<400> SEQUENCE: 20
gatgaacgct agcggcg                                                 17

<210> SEQ ID NO 21
<211> LENGTH: 18
<212> TYPE: DNA
<213> ORGANISM: Dehalococcoides ethenogenes

<400> SEQUENCE: 21
gtgccttatg catgcaag                                                18

<210> SEQ ID NO 22
<211> LENGTH: 21
<212> TYPE: DNA
<213> ORGANISM: Dehalococcoides ethenogenes

<400> SEQUENCE: 22
aataggttgc aacagtgtga a                                            21

<210> SEQ ID NO 23
<211> LENGTH: 22
<212> TYPE: DNA
<213> ORGANISM: Dehalococcoides ethenogenes

<400> SEQUENCE: 23
aatggacaga acaataggtt gc                                           22

<210> SEQ ID NO 24
<211> LENGTH: 21
<212> TYPE: DNA
<213> ORGANISM: Dehalococcoides ethenogenes

<400> SEQUENCE: 24
ggcacatcga cttcaagtgt t                                            21

<210> SEQ ID NO 25
<211> LENGTH: 20
<212> TYPE: DNA
<213> ORGANISM: Dehalococcoides ethenogenes

<400> SEQUENCE: 25
gggttgtaaa cctctttca                                               20

<210> SEQ ID NO 26
<211> LENGTH: 20
<212> TYPE: DNA
<213> ORGANISM: Dehalococcoides ethenogenes

<400> SEQUENCE: 26
taaccgggac gwgtcattca                                              20

<210> SEQ ID NO 27
<211> LENGTH: 19

```
<212> TYPE: DNA
<213> ORGANISM: Dehalococcoides ethenogenes

<400> SEQUENCE: 27
gagtacagca ggagaaaac                                                 19

<210> SEQ ID NO 28
<211> LENGTH: 21
<212> TYPE: DNA
<213> ORGANISM: Dehalococcoides ethenogenes

<400> SEQUENCE: 28
cctccttgcg gttggcacat c                                              21

<210> SEQ ID NO 29
<211> LENGTH: 19
<212> TYPE: DNA
<213> ORGANISM: Dehalococcoides ethenogenes

<400> SEQUENCE: 29
ggcagtctcg ctagaaaat                                                 19

<210> SEQ ID NO 30
<211> LENGTH: 51
<212> TYPE: DNA
<213> ORGANISM: Dehalococcoides ethenogenes

<400> SEQUENCE: 30
tgwagtagtg aacmgaaagg graacgacct gttaagtcag garmttgcac a             51

<210> SEQ ID NO 31
<211> LENGTH: 18
<212> TYPE: DNA
<213> ORGANISM: Dehalococcoides ethenogenes

<400> SEQUENCE: 31
attttctacg cgagactg                                                  18

<210> SEQ ID NO 32
<211> LENGTH: 27
<212> TYPE: DNA
<213> ORGANISM: Dehalococcoides ethenogenes

<400> SEQUENCE: 32
attttctacg cgagactagc gagactg                                        27

<210> SEQ ID NO 33
<211> LENGTH: 1542
<212> TYPE: DNA
<213> ORGANISM: Escherichia coli

<400> SEQUENCE: 33
aaattgaaga gtttgatcat ggctcagatt gaacgctggc ggcaggccta acacatgcaa    60
gtcgaacggt aacaggaaga agcttgcttc tttgctgacg agtggcggac gggtgagtaa   120
tgtctgggaa actgcctgat ggagggggat aactactgga aacggtagct aataccgcat   180
aacgtcgcaa gaccaaagag ggggaccttc gggcctcttg ccatcggatg tgcccagatg   240
ggattagcta gtaggtgggg taacggctca cctaggcgac gatccctagc tggtctgaga   300
ggatgaccag ccacactgga actgagacac ggtccagact cctacgggag gcagcagtgg   360
ggaatattgc acaatgggcg caagcctgat gcagccatgc cgcgtgtatg aagaaggcct   420
```

-continued

```
tcgggttgta aagtactttc agcggggagg aagggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctgggaa ctgcatctga tactggcaag cttgagtctc    660
gtagaggggg gtagaattcc aggtgtagcg gtgaaatgcg tagagatctg gaggaatacc    720
ggtggcgaag gcggccccct ggacgaagac tgacgctcag gtgcgaaagc gtggggagca    780
aacaggatta gataccctgg tagtccacgc cgtaaacgat gtcgacttgg aggttgtgcc    840
cttgaggcgt ggcttccgga gctaacgcgt taagtcgacc gcctggggag tacggccgca    900
aggttaaaac tcaaatgaat tgacgggggc ccgcacaagc ggtggagcat gtggtttaat    960
tcgatgcaac gcgaagaacc ttacctggtc ttgacatcca cggaagtttt cagagatgag   1020
aatgtgcctt cgggaaccgt gagacaggtg ctgcatggct gtcgtcagct cgtgttgtga   1080
aatgttgggt taagtcccgc aacgagcgca acccttatcc tttgttgcca gcggtccggc   1140
cgggaactca aaggagactg ccagtgataa actggaggaa ggtggggatg acgtcaagtc   1200
atcatggccc ttacgaccag ggctacacac gtgctacaat ggcgcataca aagagaagcg   1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct tgtacacacc gcccgtcaca ccatgggagt gggttgcaaa agaagtaggt   1440
agcttaacct tcgggagggc gcttaccact ttgtgattca tgactggggt gaagtcgtaa   1500
caaggtaacc gtaggggaac ctgcggttgg atcacctcct ta                      1542

<210> SEQ ID NO 34
<211> LENGTH: 49
<212> TYPE: DNA
<213> ORGANISM: Dehalococcoides ethenogenes

<400> SEQUENCE: 34
aacccttgtt gctagttaaa ttttctagcg agactgcccc gcgaaacgg                 49

<210> SEQ ID NO 35
<211> LENGTH: 43
<212> TYPE: DNA
<213> ORGANISM: Dehalococcoides ethenogenes

<400> SEQUENCE: 35
tgtgatgggc tgacataagt cggttcatta aagccgcaag gtg                       43

<210> SEQ ID NO 36
<211> LENGTH: 43
<212> TYPE: DNA
<213> ORGANISM: Dehalococcoides ethenogenes

<400> SEQUENCE: 36
caccttgcgg ctttaatgaa ccgacttatg tcagcccatc aca                       43

<210> SEQ ID NO 37
<211> LENGTH: 43
<212> TYPE: DNA
<213> ORGANISM: Dehalococcoides ethenogenes

<400> SEQUENCE: 37
tgtggtgggc cgacataagt tggttcacta aagccgtaag gtg                       43
```

<210> SEQ ID NO 38
<211> LENGTH: 43
<212> TYPE: DNA
<213> ORGANISM: Dehalococcoides ethenogenes

<400> SEQUENCE: 38
caccttacgg ctttagtgaa ccaacttatg tcggcccacc aca                43

<210> SEQ ID NO 39
<211> LENGTH: 43
<212> TYPE: DNA
<213> ORGANISM: Dehalococcoides ethenogenes

<400> SEQUENCE: 39
tgtggtgggc cgacatatgt tggttcacta aagccgtaag gcg                43

<210> SEQ ID NO 40
<211> LENGTH: 43
<212> TYPE: DNA
<213> ORGANISM: Dehalococcoides ethenogenes

<400> SEQUENCE: 40
cgccttacgg ctttagtgaa ccaacatatg tcggcccacc aca                43

<210> SEQ ID NO 41
<211> LENGTH: 36
<212> TYPE: DNA
<213> ORGANISM: Dehalococcoides ethenogenes

<400> SEQUENCE: 41
agttaaattt tctagcgaga ctgccccgcg aaacgg                        36

<210> SEQ ID NO 42
<211> LENGTH: 36
<212> TYPE: DNA
<213> ORGANISM: Dehalococcoides ethenogenes

<400> SEQUENCE: 42
ccgtttcgcg gggcagtctc gctagaaaat ttaact                        36

<210> SEQ ID NO 43
<211> LENGTH: 29
<212> TYPE: DNA
<213> ORGANISM: Dehalococcoides ethenogenes

<400> SEQUENCE: 43
agttaaattt tctagcgaga ctgccccgc                                29

<210> SEQ ID NO 44
<211> LENGTH: 29
<212> TYPE: DNA
<213> ORGANISM: Dehalococcoides ethenogenes

<400> SEQUENCE: 44
gcggggcagt ctcgctagaa aatttaact                                29

<210> SEQ ID NO 45
<211> LENGTH: 30
<212> TYPE: DNA
<213> ORGANISM: Dehalococcoides ethenogenes

<400> SEQUENCE: 45
ccttgttgct agttaaattt tctagcgaga                               30

```
<210> SEQ ID NO 46
<211> LENGTH: 30
<212> TYPE: DNA
<213> ORGANISM: Dehalococcoides ethenogenes

<400> SEQUENCE: 46
tctcgctaga aaatttaact agcaacaagg                                    30

<210> SEQ ID NO 47
<211> LENGTH: 32
<212> TYPE: DNA
<213> ORGANISM: Dehalococcoides ethenogenes

<400> SEQUENCE: 47
gacatgcatg aagtagtgaa ccgaaaggga aa                                 32

<210> SEQ ID NO 48
<211> LENGTH: 32
<212> TYPE: DNA
<213> ORGANISM: Dehalococcoides ethenogenes

<400> SEQUENCE: 48
tttccctttc ggttcactac ttcatgcatg tc                                 32

<210> SEQ ID NO 49
<211> LENGTH: 30
<212> TYPE: DNA
<213> ORGANISM: Dehalococcoides ethenogenes

<400> SEQUENCE: 49
ggacgtgtca ttcaatactg ttggactaga                                    30

<210> SEQ ID NO 50
<211> LENGTH: 30
<212> TYPE: DNA
<213> ORGANISM: Dehalococcoides ethenogenes

<400> SEQUENCE: 50
tctagtccaa cagtattgaa tgacacgtcc                                    30

<210> SEQ ID NO 51
<211> LENGTH: 32
<212> TYPE: DNA
<213> ORGANISM: Dehalococcoides ethenogenes

<400> SEQUENCE: 51
tgttggacta gagtacagca ggagaaaacg ga                                 32

<210> SEQ ID NO 52
<211> LENGTH: 32
<212> TYPE: DNA
<213> ORGANISM: Dehalococcoides ethenogenes

<400> SEQUENCE: 52
tccgttttct cctgctgtac tctagtccaa ca                                 32

<210> SEQ ID NO 53
<211> LENGTH: 29
<212> TYPE: DNA
<213> ORGANISM: Dehalococcoides ethenogenes

<400> SEQUENCE: 53
ggcttaaccg ggacgtgtca ttcaatact                                     29
```

```
<210> SEQ ID NO 54
<211> LENGTH: 29
<212> TYPE: DNA
<213> ORGANISM: Dehalococcoides ethenogenes

<400> SEQUENCE: 54
agtattgaat gacacgtccc ggttaagcc                              29

<210> SEQ ID NO 55
<211> LENGTH: 37
<212> TYPE: DNA
<213> ORGANISM: Dehalococcoides ethenogenes

<400> SEQUENCE: 55
aatttcccgg cttaaccggg acgtgtcatt caatact                     37

<210> SEQ ID NO 56
<211> LENGTH: 37
<212> TYPE: DNA
<213> ORGANISM: Dehalococcoides ethenogenes

<400> SEQUENCE: 56
agtattgaat gacacgtccc ggttaagccg ggaaatt                     37

<210> SEQ ID NO 57
<211> LENGTH: 31
<212> TYPE: DNA
<213> ORGANISM: Dehalococcoides ethenogenes

<400> SEQUENCE: 57
tgttaagtca ggagtttgca caggtgctgc a                           31

<210> SEQ ID NO 58
<211> LENGTH: 31
<212> TYPE: DNA
<213> ORGANISM: Dehalococcoides ethenogenes

<400> SEQUENCE: 58
tgcagcacct gtgcaaactc ctgacttaac a                           31

<210> SEQ ID NO 59
<211> LENGTH: 31
<212> TYPE: DNA
<213> ORGANISM: Dehalococcoides ethenogenes

<400> SEQUENCE: 59
cgcgtaagta acctacctct aagtggggga t                           31

<210> SEQ ID NO 60
<211> LENGTH: 31
<212> TYPE: DNA
<213> ORGANISM: Dehalococcoides ethenogenes

<400> SEQUENCE: 60
atcccccact tagaggtagg ttacttacgc g                           31

<210> SEQ ID NO 61
<211> LENGTH: 24
<212> TYPE: DNA
<213> ORGANISM: Dehalococcoides ethenogenes

<400> SEQUENCE: 61
```

-continued

```
ggctcaggat gaacgctagc ggcg                                      24

<210> SEQ ID NO 62
<211> LENGTH: 31
<212> TYPE: DNA
<213> ORGANISM: Dehalococcoides ethenogenes

<400> SEQUENCE: 62
agttggtggg gtaatggcct accaaggctt c                              31

<210> SEQ ID NO 63
<211> LENGTH: 26
<212> TYPE: DNA
<213> ORGANISM: Dehalococcoides ethenogenes

<400> SEQUENCE: 63
cctctcagac cagctaccga tcgaag                                    26

<210> SEQ ID NO 64
<211> LENGTH: 20
<212> TYPE: DNA
<213> ORGANISM: Dehalococcoides ethenogenes

<400> SEQUENCE: 64
cagaccagct accgatcgaa                                           20

<210> SEQ ID NO 65
<211> LENGTH: 28
<212> TYPE: DNA
<213> ORGANISM: Dehalococcoides ethenogenes

<400> SEQUENCE: 65
cacagggaag aataatgacg gtacctgt                                  28

<210> SEQ ID NO 66
<211> LENGTH: 27
<212> TYPE: DNA
<213> ORGANISM: Dehalococcoides ethenogenes

<400> SEQUENCE: 66
caggtaccgt cattattctt ccctgtg                                   27

<210> SEQ ID NO 67
<211> LENGTH: 30
<212> TYPE: DNA
<213> ORGANISM: Dehalococcoides ethenogenes

<400> SEQUENCE: 67
ctgttggact agagtacagc aggagaaaac                                30

<210> SEQ ID NO 68
<211> LENGTH: 20
<212> TYPE: DNA
<213> ORGANISM: Dehalococcoides ethenogenes

<400> SEQUENCE: 68
cgaaggcggt tttctaggtt                                           20

<210> SEQ ID NO 69
<211> LENGTH: 19
<212> TYPE: DNA
<213> ORGANISM: Dehalococcoides ethenogenes

<400> SEQUENCE: 69
```
ggcggttttc taggttgtc                                              19

<210> SEQ ID NO 70
<211> LENGTH: 29
<212> TYPE: DNA
<213> ORGANISM: Dehalococcoides ethenogenes

<400> SEQUENCE: 70
gagcctcagt gtcagtgaca acctagaaa                                    29

<210> SEQ ID NO 71
<211> LENGTH: 30
<212> TYPE: DNA
<213> ORGANISM: Dehalococcoides ethenogenes

<400> SEQUENCE: 71
gttagcttcg gcacagagag ggtcgatact                                   30

<210> SEQ ID NO 72
<211> LENGTH: 20
<212> TYPE: DNA
<213> ORGANISM: Dehalococcoides ethenogenes

<400> SEQUENCE: 72
cgagactgcc ccgcgaaacg                                              20

<210> SEQ ID NO 73
<211> LENGTH: 22
<212> TYPE: DNA
<213> ORGANISM: Dehalococcoides ethenogenes

<400> SEQUENCE: 73
cggggcagtc tcgctagaaa at                                           22

<210> SEQ ID NO 74
<211> LENGTH: 32
<212> TYPE: DNA
<213> ORGANISM: Dehalococcoides ethenogenes

<400> SEQUENCE: 74
ggacagaaca ataggttgca acagtgtgaa ct                                32

<210> SEQ ID NO 75
<211> LENGTH: 29
<212> TYPE: DNA
<213> ORGANISM: Dehalococcoides ethenogenes

<400> SEQUENCE: 75
gcggttggca catcgacttc aagtgttac                                    29

<210> SEQ ID NO 76
<211> LENGTH: 42
<212> TYPE: DNA
<213> ORGANISM: Artificial sequence
<220> FEATURE:
<223> OTHER INFORMATION: "GC clamp" for DGGE

<400> SEQUENCE: 76
cgcccgccgc gccccgcgcc cgtcccgccg ccccgcccg cc                      42

<210> SEQ ID NO 77
<211> LENGTH: 59
<212> TYPE: DNA

```
<213> ORGANISM: Artificial sequence
<220> FEATURE:
<223> OTHER INFORMATION: "GC clamp" sequence attached to Dehalococcoides
      ethenogenes primer sequence

<400> SEQUENCE: 77
cgcccgccgc gccccgcgcc cgtcccgccg ccccccgcccg ccgatgaacg ctagcggcg        59

<210> SEQ ID NO 78
<211> LENGTH: 62
<212> TYPE: DNA
<213> ORGANISM: Artificial sequence
<220> FEATURE:
<223> OTHER INFORMATION: "GC clamp" sequence attached to Dehalococcoides
      ethenogenes primer sequence

<400> SEQUENCE: 78
cgcccgccgc gccccgcgcc cgtcccgccg ccccccgcccg cccgaaggcg gttttctagg        60
tt                                                                       62

<210> SEQ ID NO 79
<211> LENGTH: 21
<212> TYPE: DNA
<213> ORGANISM: Dehalobacter restrictus

<400> SEQUENCE: 79
agggaagaac ggcatctgtg t                                                  21

<210> SEQ ID NO 80
<211> LENGTH: 21
<212> TYPE: DNA
<213> ORGANISM: Dehalobacter restrictus

<400> SEQUENCE: 80
catatctcta cgggattagt t                                                  21

<210> SEQ ID NO 81
<211> LENGTH: 21
<212> TYPE: DNA
<213> ORGANISM: Dehalospirillum multivorans

<400> SEQUENCE: 81
gtatcgcgtc tctttgtcct a                                                  21

<210> SEQ ID NO 82
<211> LENGTH: 21
<212> TYPE: DNA
<213> ORGANISM: Dehalospirillum multivorans

<400> SEQUENCE: 82
gctctcgaaa ctggttacct a                                                  21

<210> SEQ ID NO 83
<211> LENGTH: 20
<212> TYPE: DNA
<213> ORGANISM: Desulfitobacterium dehalogenans

<400> SEQUENCE: 83
agaatcccgt ggaaacatgg                                                    20

<210> SEQ ID NO 84
<211> LENGTH: 20
<212> TYPE: DNA
<213> ORGANISM: Desulfitobacterium dehalogenans
```

```
<400> SEQUENCE: 84
ggactgcatc ggaaactggt                                              20

<210> SEQ ID NO 85
<211> LENGTH: 19
<212> TYPE: DNA
<213> ORGANISM: Desulfitobacterium dehalogenans

<400> SEQUENCE: 85
ccatgtttcc acgggattc                                               19

<210> SEQ ID NO 86
<211> LENGTH: 19
<212> TYPE: DNA
<213> ORGANISM: Desulfitobacterium dehalogenans

<400> SEQUENCE: 86
tcggatttgc tccacctca                                               19

<210> SEQ ID NO 87
<211> LENGTH: 23
<212> TYPE: DNA
<213> ORGANISM: Desulfuromonas chloroethnica

<400> SEQUENCE: 87
gggataacac ttcgaaaggg gtg                                          23

<210> SEQ ID NO 88
<211> LENGTH: 22
<212> TYPE: DNA
<213> ORGANISM: Desulfuromonas chloroethnica

<400> SEQUENCE: 88
ggtaccgtca ggcccaagtg tt                                           22

<210> SEQ ID NO 89
<211> LENGTH: 27
<212> TYPE: DNA
<213> ORGANISM: Dehalococcoides Family A Group

<400> SEQUENCE: 89
taacctgcct ttaagtgggg gataaca                                      27

<210> SEQ ID NO 90
<211> LENGTH: 26
<212> TYPE: DNA
<213> ORGANISM: Dehalococcoides Family A Group

<400> SEQUENCE: 90
tcctctcaga ccagctaccg atcatc                                       26

<210> SEQ ID NO 91
<211> LENGTH: 23
<212> TYPE: DNA
<213> ORGANISM: Dehalococcoides Family A Group

<400> SEQUENCE: 91
gtcatccgat actgttggac ttg                                          23

<210> SEQ ID NO 92
<211> LENGTH: 18
<212> TYPE: DNA
```

<213> ORGANISM: Dehalococcoides Family A Group

<400> SEQUENCE: 92

```
gctcccggtc acccggtg                                                    18
```

<210> SEQ ID NO 93
<211> LENGTH: 24
<212> TYPE: DNA
<213> ORGANISM: Dehalococcoides related Family A Group

<400> SEQUENCE: 93

```
aagtccaaca gtatcggatg accc                                             24
```

<210> SEQ ID NO 94
<211> LENGTH: 1014
<212> TYPE: DNA
<213> ORGANISM: Dehalococcoides related Family A Group

<400> SEQUENCE: 94

```
ggaatattgg gcaatgggcg aaagcctgac ccagcgacgc cgcgtgaggg atgacggcct       60
tcgggttgta aacctctttt ctcagggaag aataatgacg gtacctgagg aataagtctc     120
ggctaactac gtgccagcag ccgcggtaat acgtaggagg cgagcgttat ccggatttat     180
tgggcgtaaa gtgggcgtag gtggtctttc aagtcggatg tgaaatctcc cggctcaact     240
gggaggggtc atccgatact gttggacttg agtacagcag gggaaaatgg aattcccggt     300
gtagtggtga aatgcgtaga tatcgggagg aacaccagag gcgaaggcga ttttccaggc     360
tgaaactgac actgaggccc gaaaagcgtg gggagcgaaa caggattaga taccctggta     420
gtccacgcct taaactatgg gtactaggta tagggagtat cgaccctctc ttgtgcccga     480
agctaacgct ttaagtaccc cgcctgggga gtacggtcgc aagactaaaa ctcaaaggaa     540
ttgacggggg cccgcacaag cagcggagcg tgtggtttaa ttcgatgcta cacgaagaac     600
ctcaccaagg cttgacatgt tagaagtagt gaaccgaaag ggaaacgacc tgtcaaatca     660
ggagctatca caggtgctgc atggctgtcg tcagctcgtg ccgtgaggtg tatggttaag     720
tcctgcaacg agcgcaaccc ttattgccag ttatattctc tggcgatact gcctcgcaaa     780
acggggagga aggtggggat gacgtcaagt cagcatggcc tttatgcctt gggctacaca     840
cacgctacaa tgggcggcac aatgggttgc caccggtga ccgggagcta atccccaaaa      900
ccgccctcag ttcggatcgc aggctgaaac ccgcctgcgt gaagtcggag ttgctagtaa     960
acgcgtgtca gcataagcgc gttgaatacg ttctcgggcc ttgtacacac cgcc          1014
```

<210> SEQ ID NO 95
<211> LENGTH: 1385
<212> TYPE: DNA
<213> ORGANISM: Dehalococcoides related Family A Group

<400> SEQUENCE: 95

```
ggctcaggat gaacgctagc ggcgcgcctt atgcatgcaa gtcgaacggt ctctcgcaag      60
agagatagtg gcaaacgggt gagtaataga taaataacct gcctttaagt gggggataac    120
acttcgaaag aagtgctaat accgcatgtg gtgctctttc ataagaagga tcactaaaac    180
cgcaaggtgc ttgaagaggg gtttgtctcc gattagctag ttggtgggt aacggcctac     240
caaggcgatg atcggtagct ggtctgagag gatggtcagc cacactggaa ctgagacacg    300
gtccagactc ctacgggagg cagcagcaag gaatcttggg caatgggcga aagcctgacc    360
cagcgacgcc gcgtgaggga tgacggcctt cgggttgtaa acctcttttc tcagggaaga    420
```

```
ataatgacgg tacctgagga ataagtctcg gctaactacg tgccagcagc cgcggtaata      480
cgtaggaggc gagcgttatc cggatttatt gggcgtaaag tgggcgtagg tggtctttca      540
agtcagatgt gaaatctccc ggctcaactg gaggggtca tctgatactg ttggacttga       600
gtatggcagg agaaaacgga attcccggtg tagtggtgaa atgcgtagat atcgggagga      660
acaccagagg cgaaggcggt tttctaggcc aaaactgaca ctgaggcccg aaagcgtggg      720
gagcgaacag gattagatac cctggtagtc cacgccctaa acactgggta ccaggtatag      780
ggagtatcga ccctctctgt gccgaagcta acgctttaag tacccgcct ggggagtacg       840 gtcgcaagac taaaactcaa aggaattgac gggggcccgc acaagcagcg agcgtgtgg       900 tttaattcga tgctacacga gaacctcac cagggcttga catgttagaa gtagtgaacc       960 gaaagggga cgacctgtta agtcaggagc tatcacaggt gctgcatggc tgtcgtcagc      1020
tcgtgccgtg aggtgtatgg ttaagtcctg caacgagcgc aacccttatt gctagttata     1080
ttctctagcg atactgcctc gcaaaacggg gaggaaggtg gggatgacgt caagtcagta     1140
tggcccttat accctgggct acacacacgc tacaatgggc ggtacaatgg gttgccaccg     1200
ggtgaccggg agctaatcct taaagccatc ctcagttcgg attgcaggct gaaactcgcc     1260
tgcatgaagg tggagttgct agtaaccgcg tgtcagcaca gcgcggtgaa tacgttctcg     1320
gggattgtac acaccgcccg tcacgtcatg aaagttggta acactgaagt cgatgtgcca     1380
accgc                                                                1385
```

<210> SEQ ID NO 96
<211> LENGTH: 51
<212> TYPE: DNA
<213> ORGANISM: Dehalococcoides ethenogenes

<400> SEQUENCE: 96

```
tgtgrtgggc ygacatawgt yggttcayta aagccgyaag gygcttggtg a              51
```

<210> SEQ ID NO 97
<211> LENGTH: 51
<212> TYPE: DNA
<213> ORGANISM: Dehalococcoides ethenogenes

<400> SEQUENCE: 97

```
tgtgatgggc tgacataagt cggttcatta aagccgcaag gtgcttggtg a              51
```

<210> SEQ ID NO 98
<211> LENGTH: 51
<212> TYPE: DNA
<213> ORGANISM: Dehalococcoides ethenogenes

<400> SEQUENCE: 98

```
tgtggtgggc cgacataagt tggttcacta aagccgtaag gtgcttggtg a              51
```

<210> SEQ ID NO 99
<211> LENGTH: 51
<212> TYPE: DNA
<213> ORGANISM: Dehalococcoides ethenogenes

<400> SEQUENCE: 99

```
tgtggtgggc cgacatatgt tggttcacta aagccgtaag gcgcttggtg a              51
```

<210> SEQ ID NO 100
<211> LENGTH: 51
<212> TYPE: DNA

```
<213> ORGANISM: Dehalococcoides ethenogenes

<400> SEQUENCE: 100
tgwagtagtg aacygaaagg graacgacct gttaagtcag garyttgcac a          51

<210> SEQ ID NO 101
<211> LENGTH: 51
<212> TYPE: DNA
<213> ORGANISM: Dehalococcoides ethenogenes

<400> SEQUENCE: 101
tgaagtagtg aaccgaaagg gaaacgacct gttaagtcag gagtttgcac a          51

<210> SEQ ID NO 102
<211> LENGTH: 51
<212> TYPE: DNA
<213> ORGANISM: Dehalococcoides ethenogenes

<400> SEQUENCE: 102
tgaagtagtg aaccgaaagg gaaacgacct gttaagtcag gagtttgcac a          51

<210> SEQ ID NO 103
<211> LENGTH: 51
<212> TYPE: DNA
<213> ORGANISM: Dehalococcoides ethenogenes

<400> SEQUENCE: 103
tgtagtagtg aactgaaagg ggaacgacct gttaagtcag gaacttgcac a          51
```